US007557079B2

(12) United States Patent
Fagan et al.

(10) Patent No.: US 7,557,079 B2

(45) Date of Patent: Jul. 7, 2009

(54) METALLOPROTEASE PROTEINS

(75) Inventors: Richard Joseph Fagan, London (GB); Christopher Benjamin Phelps, London (GB); Christine Power, Thoiry (FR); Richard James Mitter, London (GB); Ursula Boschert, Vaumarcus (CH); Yolande Chvatchko, Vaumarcus (CH)

(73) Assignee: Ares Trading, S.A., Aubonne (CH)

( * ) Notice: Subject to any disclaimer, the term of this patent is extended or adjusted under 35 U.S.C. 154(b) by 293 days.

(21) Appl. No.: 10/539,847

(22) PCT Filed: Dec. 23, 2003

(86) PCT No.: PCT/GB03/05664

§ 371 (c)(1), (2), (4) Date: Dec. 9, 2005

(87) PCT Pub. No.: WO2004/056983

PCT Pub. Date: Jul. 8, 2004

(65) Prior Publication Data

US 2006/0252117 A1 Nov. 9, 2006

(30) Foreign Application Priority Data

Dec. 23, 2002 (GB) ................................ 0230006.9

(51) Int. Cl.

| | |
|---|---|
| *C07K 14/00* | (2006.01) |
| *A61K 38/00* | (2006.01) |
| *C07H 21/04* | (2006.01) |

(52) U.S. Cl. ............................ 514/2; 514/12; 530/350; 435/69.1; 435/226; 435/320.1; 536/23.2

(58) Field of Classification Search .................... 514/2, 514/12; 530/350; 435/59.1, 226, 320.1, 435/325, 69.1; 536/23.2

See application file for complete search history.

(56) References Cited

FOREIGN PATENT DOCUMENTS

| | | | |
|---|---|---|---|
| WO | WO 02/16566 | A2 | 2/2002 |
| WO | WO 02/066624 | A2 | 8/2002 |
| WO | WO 03/025131 | A2 | 3/2003 |

OTHER PUBLICATIONS

Quesada, V. et al. "Identification and characterization of human and mouse ovastacin: a novel metalloproteinase similar to hatching enzymes from arthropods, birds, amphibians, and fish" *J. Biol. Chem.*, 2004, 279:26627-26634.

Yasumasu, S. et al. "Isolation of cDNAs for LCE and HCE, two constituent proteases of the hatching enzyme of *Oryzias latipes*, and concurrent expression of their mRNAs during development" *Develop. Biol.*, 1992, 153:250-258.

*Primary Examiner*—Chih-Min Kam

(74) *Attorney, Agent, or Firm*—Saliwanchik, Lloyd & Saliwanchik

(57) ABSTRACT

This invention relates to proteins termed INSP005*a* and INSP005*b*, herein identified as secreted proteins, in particular members of the metalloprotease family and to the use of these proteins and nucleic acid sequences from the encoding genes in the diagnosis, prevention, and treatment of disease.

45 Claims, 18 Drawing Sheets

FIGURE 1

Blastp vs. NCBI-nr

```
>dbj|BAB68513.1| hatching enzyme EHE4 [Anguilla japonica]
          Length = 271

 Score =  197 bits (502), Expect = 1e-49
 Identities = 103/233 (44%), Positives = 141/233 (60%), Gaps = 5/233 (2%)

Query: 52  DKDIPAINQGLILEETPESSFLIEGDIIRPSPFRLLSATSNK--WPMGGSGVVEVPFLLS 109
            D D   I   ++      S  L+EGD+I  +    +   +N+  W     G+VEVP+ +S
Sbjct: 41  DPDDVDITTSILQSNNGSSEILMEGDLIVSNTRNAMKCWNNQCLWRKSSDGLVEVPYTVS 100

Query: 110 SKYDEPSHQVILEALAEFERSTCIRFVTYQDQRDFISIIPMYGCFSSVGRSGGMQVVSLA 169
           +++     + I  A+  F   TCIRFV    QRDFISI    GC+S +GR+GG QVVSLA
Sbjct: 101 NEFSYYHKKRIENAMKTFNTETCIRFVPRSSQRDFISIESRDGCYSYLGRTGGKQVVSLA 160

Query: 170 PT-CLQKGRGIVLHELMHVLGFWHEHTRADRDRYIRVNWNEILPGFEINFIKSQSSNMLT 228
              C+    GI+ HEL H LGF+HEHTR+DRD Y+++NW  + P    NF    ++N+ T
Sbjct: 161 RYGCVY--HGIIQHELNHALGFYHEHTRSDRDEYVKINWENVAPHTIYNFQTQDTNNLNT 218

Query: 229 PYDYSSVMHYGRLAFSRRGLPTITPLWAPSVHIGQRWNLSASDITRVLKLYGC 281
           PYDY+S+MHYGR AFS  G+ TITP+  P+  IGQR ++S  DI R+ KLY C
Sbjct: 219 PYDYTSIMHYGRTAFSTNGMDTITPVPNPNQSIGQRRSMSRGDILRIKKLYSC 271
```

Tblastn vs. NCBI-est

```
Tissue - Uterus tumour

>gb|BI061462.1|BI061462 IL3-UT0117-070301-494-H12 UT0117 Homo sapiens cDNA.
          Length = 652

 Score =  175 bits (443), Expect = 2e-42
 Identities = 85/86 (98%), Positives = 85/86 (98%)
 Frame = -2

Query: 29  SCAGACGTSFPDGLTPEGTQASGDKDIPAINQGLILEETPESSFLIEGDIIRPSPFRLLS 88
            SCAGACGTSFPDGLTPEGTQASGDKDIPAINQGLILEETPESSFLIEGDIIRPSPFRLLS
Sbjct: 546 SCAGACGTSFPDGLTPEGTQASGDKDIPAINQGLILEETPESSFLIEGDIIRPSPFRLLS 367

Query: 89  ATSNKWPMGGSGVVEVPFLLSSKYDE 114
            ATSNKWPMGGSGVVEVPFLLSSKY E
Sbjct: 366 ATSNKWPMGGSGVVEVPFLLSSKYGE 289
```

FIGURE 2

| Library | Tissue/cell source | Vector | Host strain | Supplier | Cat. no. |
|---|---|---|---|---|---|
| 1 | human fetal brain | Zap II | XL1-Blue MRF' | Stratagene | 936206 |
| 2 | human ovary | GT10 | LE392 | Clontech | HL1098a |
| 3 | human pituitary | GT10 | LE392 | Clontech | HL1097a |
| 4 | human placenta | GT11 | LE392 | Clontech | HL1075b |
| 5 | human testis | GT11 | LE392 | Clontech | HL1010b |
| 6 | human substantia nigra | GT10 | LE392 | in house | |
| 7 | human fetal brain | GT10 | LE392 | in house | |
| 8 | human cortex brain | GT10 | LE392 | in house | |
| 9 | human colon | GT10 | LE392 | Clontech | HL1034a |
| 10 | human fetal brain | GT10 | LE392 | Clontech | HL1065a |
| 11 | human fetal lung | GT10 | LE392 | Clontech | HL1072a |
| 12 | human fetal kidney | GT10 | LE392 | Clontech | HL1071a |
| 13 | human fetal liver | GT10 | LE392 | Clontech | HL1064a |
| 14 | human bone marrow | GT10 | LE392 | Clontech | HL1058a |
| 15 | human peripheral blood monocytes | GT10 | LE392 | Clontech | HL1050a |
| 16 | human placenta | GT10 | LE392 | in house | |
| 17 | human SHSYSY | GT10 | LE392 | in house | |
| 18 | human U373 cell line | GT10 | LE392 | in house | |
| 19 | human CFPoc-1 cell line | Uni Zap | XL1-Blue MRF' | Stratagene | 936206 |
| 20 | human retina | GT10 | LE392 | Clontech | HL1132a |
| 21 | human urinary bladder | GT10 | LE392 | in house | |
| 22 | human platelets | Uni Zap | XL1-Blue MRF' | in house | |
| 23 | human neuroblastoma Kan + TS | GT10 | LE392 | in house | |
| 24 | human bronchial smooth muscle | GT10 | LE392 | in house | |
| 25 | human bronchial smooth muscle | GT10 | LE392 | in house | |
| 26 | human Thymus | GT10 | LE392 | Clontech | HL1127a |
| 27 | human spleen 5' stretch | GT11 | LE392 | Clontech | HL1134b |
| 28 | human peripheral blood monocytes | GT10 | LE392 | Clontech | HL1050a |
| 29 | human testis | GT10 | LE392 | Clontech | HL1065a |
| 30 | human fetal brain | GT10 | LE392 | Clontech | HL1065a |
| 31 | human substantia nigra | GT10 | LE392 | Clontech | HL1093a |
| 32 | human placenta#11 | GT11 | LE392 | Clontech | HL1075b |
| 33 | human Fetal brain | GT10 | LE392 | Clontech | custom |
| 34 | human placenta #59 | GT10 | LE392 | Clontech | HL5014a |
| 35 | human pituitary | GT10 | LE392 | Clontech | HL1097a |
| 36 | human pancreas #63 | Uni Zap XR | XL1-Blue MRF' | Stratagene | 937208 |
| 37 | human placenta #19 | GT11 | LE392 | Clontech | HL1008 |
| 38 | human liver 5'stretch | GT11 | LE392 | Clontech | HL1115b |
| 39 | human uterus | Zap-CMV XR | XL1-Blue MRF' | Stratagene | 980207 |
| 40 | human kidney large-insert cDNA library | TriplEx2 | XL1-Blue | Clontech | HL5507u |

FIGURE 3

```
   1  AGGTCCTTGT GGACAATAGC TATTCTTCTT GGCTCTGTCG CTTCCCTTCA CTGGGTGCAG
  61  GTGACTGTGG GGGTGTCCCC AAATGCTGCC CAGCGCTGAC ATGCTCCGCC TCTGGGATTT
                                                 m  l  r   l  w  d

 121  CAATCCAGGT GGGGCCCTGA GTGACCTGGC TCTGGGGCTC AGGGGTATGG AGGAGGGGGG
      f  n  p   g  a  l   s  d  l   a  l  g  l  r  g  m   e  e  g

 181  ATATAGCTGC GCAGGAGCCT GTGGTACCAG CTTCCCAGAT GGCCTCACCC CTGAGGGAAC
      g  y  s  c  a  g  a   c  g  t   s  f  p  d  g  l  t   p  e  g

 241  CCAGGCCTCC GGGGACAAGG ACATTCCTGC AATTAACCAA GGGCTCATCC TGGAAGAAAC
      t  q  a  s  g  d  k   d  i  p   a  i  n  q  g  l  i   l  e  e

 301  CCCAGAGAGC AGCTTCCTCA TCGAGGGGGA CATCATCCGG CCGAGTCCCT TCCGACTGCT
      t  p  e  s  s  f  l   i  e  g   d  i  i  r  p  s  p   f  r  l

 361  GTCAGCAACC AGCAACAAAT GGCCCATGGG TGGTAGTGGT GTCGTGGAGG TCCCCTTCCT
      l  s  a  t  s  n  k   w  p  m   g  g  s  g  v  v  e   v  p  f

 421  GCTCTCCAGC AAGTACGATG AGCCCAGCCA TCAGGTCATC CTGGAGGCTC TTGCGGAGTT
      l  l  s  s  k  y  d   e  p  s   h  q  v  i  l  e  a   l  a  e

 481  TGAACGTTCC ACGTGCATCA GGTTTGTCAC CTATCAGGAC CAGAGAGACT TCATTTCCAT
      f  e  r  s  t  c  i   r  f  v   t  y  q  d  q  r  d   f  i  s

 541  CATCCCCATG TATGGGTGCT TCTCGAGTGT GGGGCGCAGT GGAGGGATGC AGGTGGTCTC
      i  i  p  m  y  g  c   f  s  s   v  g  r  s  g  g  m   q  v  v

 601  CCTGGCGCCC ACGTGTCTCC AGAAGGGCCG GGGCATTGTC CTTCATGAGC TCATGCATGT
      s  l  a  p  t  c  l   q  k  g   r  g  i  v  l  h  e   l  m  h
                                                      CP1
 661  GCTGGGCTTC TGGCACGAGC ACACGCGGGC CGACCGGGAC CGCTATATCC GTGTCAACTG
      v  l  g  f  w  h  e   h  t  r   a  d  r  d  r  y  i   r  v  n

 721  GAACGAGATC CTGCCAGGCT TTGAAATCAA CTTCATCAAG TCTCAGAGCA GCAACATGCT
      w  n  e  i  l  p  g   f  e  i   n  f  i  k  s  q  s   s  n  m

 781  GACGCCCTAT GACTACTCCT CTGTGATGCA CTATGGGAGG CTCGCCTTCA GCCGGCGTGG
      l  t  p  y  d  y  s   s  v  m   h  y  g  r  l  a  f   s  r  r
                                                 78836-GR1-3'
 841  GCTGCCCACC ATCACACCAC TTTGGGCCCC CAGTGTCCAC ATCGGCCAGC GATGGAACCT
      g  l  p  t  i  t  p   l  w  a   p  s  v  h  i  g  q   r  w  n

 901  GAGTGCCTCG GACATCACCC GGGTCCTCAA ACTCTACGGC TGCAGCCCAA GTGGCCCCAG
      l  s  a  s  d  i  t   r  v  l   k  l  y  g  c  s  p   s  g  p
       78836-GR1nest- 3'                      CP2
 961  GCCCCGTGGG AGAGGTGAGT GGCATGGCAG GAAGGTGACT TGAACCTGGA GAAGGCGCCT
      r  p  r  g  r  g  e   w  h  g   r  k  v  t  -

1021  GTGCTCTAAT GGTGTCAGGG AGGGTGACAA GGAGGGAGAT GAGGTTGCAG GGGGAGCAGG
1081  GTGAGATCAC GGGGGCTTGC CAC
```

Position and sense of PCR primers ——▶ - - - - -▶

FIGURE 4

| Primer | Name | Sequence (5'-3') |
|---|---|---|
| CP1 | 4C5 | ACC GCT ATA TCC GTG TCA A (SEQ ID NO:40) |
| CP2 | 4C6 | GCT GCA GCC GTA GAG TTT (SEQ ID NO:41) |
| GeneRacer 3' | | GCT GTC AAC GAT ACG CTA CGT AAC G (SEQ ID NO:42) |
| 78836-GR1-3' | | AGT GTC CAC ATC GGC CAG CGA TGG AA (SEQ ID NO:43) |
| GeneRacer 3' nested | | CGC TAC GTA ACG GCA TGA CAG TG (SEQ ID NO:44) |
| 78836-GR1nest-3' | | ATG GAA CCT GAG TGC CTC GGA CAT C (SEQ ID NO:45) |
| 78836-FL-F | 4C7 | CTG TCA GCA ACC AGC AAC AA (SEQ ID NO:46) |
| 78836-FL-R | 9B2 | AGC CAC AGG CTT AAT CTT CG (SEQ ID NO:47) |
| 78836-FL2-F | 9E6 | TCT ACC ATG GAG GGT GTA GG (SEQ ID NO:48) |

FIGURE 5

1 ATGGAACCTG AGTGCCTCGG ACATCACCCG GGTCCTCAAA CTCTACGGCT GCAGCCCAAG
w n l s a s d i t r v l k l y g c s p

61 TGGCCCCAGG CCCCGTGGGA GAGGGTCCCA TGCCCACAGC ACTGGTAGGA GCCCCGCTCC
s g p r p r g r g s h a h s t g r s p a

121 GGCCTCCCTA TCTCTGCAGC GGCTTTTGGA GGCACTGTCG GCGGAATCCA GGAGCCCCGA
p a s l s l q r l l e a l s a e s r s p

181 CCCCAGTGGT TCCAGTGCGG GAGGCCAGCC CGTTCCTGCA GGGCCTGGGG AGAGCCCACA
d p s g s s a g g q p v p a g p g e s p

241 TGGGTGGGAG TCCCCTGCCC TGAAAAAGCT CAGTGCAGAG GCCTCGGCAA GGCAGCCTCA
h g w e s p a l k k l s a e a s a r q p

301 GACCCTAGCT TCCTCCCCAA GATCAAGGCC TGGAGCAGGT GCCCCCGGTG TTGCTCAGGA
q t l a s s p r s r p g a g a p g v a q

361 GCAGTCCTGG CTGGCCGGAG TGTCCACCAA GCCCACAGTC CCATCTTCAG AAGCAGGAAT
e q s w l a g v s t k p t v p s s e a g

421 CCAGCCAGTC CCTGTCCAGG GAAGCCCAGC TCTGCCAGGG GGCTGTGTAC CTAGAAATCA
i q p v p v q g s p a l p g g c v p r n

481 TTTCAAGGGG ATGTCCGAAG ATTAAGCCTG TGGCTTCTGT CCCCAAGTAG GGAGGGCATC
h f k g m s e d

541 CTCTGCCCAG TGGAGCTGGG TCGTCTACCT CTTGGCTCCT TTGGGCCACA CCACTGTCTT
601 CCAGCCCCAA CCTACCACCC CATCTCAGAG GGCCAGGACT CTTCCCCTGT CTCTCTTCAC
661 TGTGTTCCCC TAAGGGCTCC TAGGGCCAGG GGTTCTTCTA GCTCTGCCAC AGGGGAAGGC
721 AGGCCTGGCT GTGCCTGCTC TTGACTTTTG CCCAGCCCTG GTGGATGCTG GGAATGGGAG
781 GTGACATTCT CCAGGGACAG GTCCTGGAAG GGGTGGGGAA GAGGTAGGTT CCAGCCCCGC
841 AGAACCCTGG AATCCCTCCT GTGCCTGAGG CCCTGCCCCC CAGCATGGAC TAATGGTGTC
901 CCTACCTCTC CCTCAGGGCA GCCCTGTGGC TGGGACCCTG GGAACAGCCT CCCATCCCAC
961 CCAACATGCC CAAGTGTGGG GGAATGTTCT ACAGCAGTGT AGCCTCCAGC CCTTCTCTCC
1021 AGGAGGCTTT GAGAGCCCAA CTTACTCCCC TGCAGAGCAG GAAGGTGGTA GGTCAAGTGT
1081 GGCCACCATT GGGGAGACGA GAAAGAAGTG GGGCCCCACC AGATTGCACA ATGGGAACCT
1141 CAGCTGGCCC CTGAACAGAG GACTCAGTTG TCTCCACCCT ACACCGCTAT TCCCTGGAGC
1201 TCAGCCAGGC GCAGCCTTGG AAGGAGAAAG GGCTGGGGTT ACCTGGCTTG TCCTCCTCCA
1261 GGAAAGCCCC CTTCCTCCTC TGCCCCAGCT CCCAGCCTGG CCTCCTCCAG GCAGGCCCTA
1321 CTCCTCTGCC CCAGCTCCGG CTTTCCCCAT GAGGTTTGTC CCAGGCATGA AGAAAGCATC
1381 CAGGGTGCCA ATGAGTGGGC CTAGGCCAGA GGCCCCTCAG TCCCCAAGGG TACTGTTTTG
1441 GTGGCCTTTC AGAGGGTCAA GGAAGCCCTG CTTGGGGTAG AAGGGGCAGG AGCCCCACAT
1501 GTTGGGGGAG GA<u>AATAAA</u>GT GGAGTGTGCT GTGCTGAAAA AAAAAAAAAA AAAA

TAA Stop codon

<u>AATAAA</u> Consensus polyadenylation site (underlined)

FIGURE 6

| Primer | Sequence (5'-3') |
|---|---|
| T3 | ATT AAC CCT CAC TAA AGG GA (SEQ ID NO:49) |
| T7 | TAA TAC GAC TCA CTA TAG GG (SEQ ID NO:50) |
| SP6 | ATT TAG GTG ACA CTA TAG (SEQ ID NO:51) |

FIGURE 7

```
   1 CTGTCAGCAA CCAGCAACAA ATGGCCCATG GGTGGTAGTG GTGTCGTGGA GGTCCCCTTC
                                   m   g   g   s   g   v   v   e   v   p   f
       78836-FL-F
  61 CTGCTCTCCA GCAAGTACGA TGAGCCCAGC CGCCAGGTCA TCCTGGAGGC TCTTGCGGAG
      l  l  s   s  k  y   d  e  p  s   r  q  v   i  l  e   a  l  a  e
 121 TTTGAACGTT CCACGTGCAT CAGGTTTGTC ACCTATCAGG ACCAGAGAGA CTTCATTTCC
      f  e  r   s  t  c   i  r  f  v   t  y  q   d  q  r   d  f  i  s
 181 ATCATCCCCA TGTATGGGTG CTTCTCGAGT GTGGGGCGCA GTGGAGGGAT GCAGGTGGTC
      i  i  p   m  y  g   c  f  s  s   v  g  r   s  g  g   m  q  v  v
 241 TCCCTGGCGC CCACGTGTCT CCAGAAGGGC CGGGGCATTG TCCTTCATGA GCTCATGCAT
      s  l  a   p  t  c   l  q  k  g   r  g  i   v  l  h   e  l  m  h
 301 GTGCTGGGCT TCTGGCACGA GCACACGCGG GCCGACCGGG ACCGCTATAT CCGTGTCAAC
      v  l  g   f  w  h   e  h  t  r   a  d  r   d  r  y   i  r  v  n
 361 TGGAACGAGA TCCTGCCAGG CTTTGAAATC AACTTCATCA AGTCTCAGAG CAGCAACATG
      w  n  e   i  l  p   g  f  e  i   n  f  i   k  s  q   s  s  n  m
 421 CTGACGCCCT ATGACTACTC CTCTGTGATG CACTATGGGA GGCTCGCCTT CAGCCGGCGT
      l  t  p   y  d  y   s  s  v  m   h  y  g   r  l  a   f  s  r  r
 481 GGGCTGCCCA CCATCACACC ACTTTGGGCC CCCAGTGTCC ACATCGGCCA GCGATGGAAC
      g  l  p   t  i  t   p  l  w  a   p  s  v   h  i  g   q  r  w  n
 541 CTGAGTGCCT CGGACATCAC CCGGGTCCTC AAACTCTACG GCTGCAGCCC AAGTGGCCCC
      l  s  a   s  d  i   t  r  v  l   k  l  y   g  c  s   p  s  g  p
 601 AGGCCCCGTG GGAGAGGGTC CCATGCCCAC AGCACTGGTA GGAGCCCCGC CCCGGCCTCC
      r  p  r   g  r  g   s  h  a  h   s  t  g   r  s  p   a  p  a  s
 661 CTATCTCTGC AGCGGCTTTT GGAGGCACTG TCGGCGGAAT CCAGGAGCCC CGACCCCAGT
      l  s  l   q  r  l   l  e  a  l   s  a  e   s  r  s   p  d  p  s
 721 GGTTCCAGTG CGGGAGGCCA GCCCGTTCCT GCAGGGCCTG GGGAGAGCCC ACATGGGTGG
      g  s  s   a  g  g   q  p  v  p   a  g  p   g  e  s   p  h  g  w
 781 GAGTCCCCTG CCCTGAAAAA GCTCAGTGCA GAGGCCTCGG CAAGGCAGCC TCAGACCCTA
      e  s  p   a  l  k   k  l  s  a   e  a  s   a  r  q   p  q  t  l
 841 GCTTCCTCCC CAAGATCAAG GCCTGGAGCA GGTGCCCCCG GTGTTGCTCA GGAGCAGTCC
      a  s  s   p  r  s   r  p  g  a   g  a  p   g  v  a   q  e  q  s
 901 TGGCTGGCCG GAGTGTCCAC CAAGCCCACA GTCCCATCTT CAGAAGCAGG AATCCAGCCA
      w  l  a   g  v  s   t  k  p  t   v  p  s   s  e  a   g  i  q  p
 961 GTCCCTGTCC AGGGAAGCCC AGCTCTGCCA GGGGGCTGTG TACCTAGAAA TCATTTCAAG
      v  p  v   q  g  s   p  a  l  p   g  g  c   v  p  r   n  h  f  k
1021 GGGATGTCCG AAGATTAAGC CTGTGGCT
      g  m  s   e  d
                         78836-FL-R
```

FIGURE 8

```
Query= INSP005a
        (336 letters)

Database: All non-redundant GenBank CDS
translations+PDB+SwissProt+PIR+PRF
           1,247,039 sequences; 397,579,747 total letters

Searching..................................................done

                                                                  Score    E
Sequences producing significant alignments:                      (bits)  Value

ref|XP_141346.1| similar to hatching enzyme EHE7 [Anguilla japon...   416   e-115
dbj|BAB68518.1| hatching enzyme EHE13 [Anguilla japonica]             187   2e-46
dbj|BAB68515.1| hatching enzyme EHE7 [Anguilla japonica]              186   4e-46
dbj|BAB68516.1| hatching enzyme EHE10 [Anguilla japonica]             186   4e-46
dbj|BAB68513.1| hatching enzyme EHE4 [Anguilla japonica]              186   5e-46
dbj|BAB68517.1| hatching enzyme EHE12 [Anguilla japonica]             183   3e-45
dbj|BAB68514.1| hatching enzyme EHE6 [Anguilla japonica]              183   3e-45
dbj|BAB68519.1| hatching enzyme EHE14 [Anguilla japonica]             182   7e-45
pir||C48826 high choriolytic hatching proteinase (EC 3.4.24.-) H...   171   1e-41
dbj|BAA12146.1| choriolysin H [Oryzias latipes]                       171   2e-41
```

Top alignment to known metalloproteinase:

```
>dbj|BAB68518.1| hatching enzyme EHE13 [Anguilla japonica]
          Length = 271

 Score =  187 bits (475), Expect = 2e-46
 Identities = 93/183 (50%), Positives = 124/183 (66%), Gaps = 3/183 (1%)

Query: 5    GVVEVPFLLSSKYDEPSRQVILEALAEFERSTCIRFVTYQDQRDFISIIPMYGCFSSVGR 64
            G+VEVP+ +SS++     ++ I  A+  F   TCIRFV     QRDFISI    GC+S +GR
Sbjct: 91   GLVEVPYTVSSEFSYYHKKRIENAMETFNTETCIRFVPRSSQRDFISIESRDGCYSYLGR 150

Query: 65   SGGMQVVSLAPT-CLQKGRGIVLHELMHVLGFWHEHTRADRDRYIRVNWNEILPGFEINF 123
            +GG QVVSLA    C+     GI+ HEL H LGF+HEHTR+DRD Y+++NW  + P    NF
Sbjct: 151  TGGKQVVSLARYGCVY--HGIIQHELNHALGFYHEHTRSDRDEYVKINWENVAPHTIYNF 208

Query: 124  IKSQSSNMLTPYDYSSVMHYGRLAFSRRGLPTITPLWAPSVHIGQRWNLSASDITRVLKL 183
             +  ++N+ TPYDY+S+MHYGR AFS  G+ TITP+  P+  IGQR ++S  DI R+ KL
Sbjct: 209  QEQDTNNLNTPYDYTSIMHYGRTAFSTNGMDTITPVPNPNQSIGQRRSMSKGDILRINKL 268

Query: 184  YGC 186
            Y C
Sbjct: 269  YSC 271
```

FIGURE 9

Molecule: pCR4 TOPO-IPAAA78836-1, 5005 bps DNA Circular
File Name: 13164.cm5, dated 24 Oct 2002

Description: Ligation of inverted 78836_F2/R8 PCR product into pCR4-TOPO linear vector*

Molecule Features:

| Type | Start | End | | Name | Description |
|---|---|---|---|---|---|
| REGION | 205 | 221 | | M13 | rev priming site |
| MARKER | 243 | | | T3 | |
| REGION | 262 | 294 | | | Polylinker' |
| REGION | 294 | 294 | | | TOPO cloning site' |
| GENE | 1315 | 308 | C | IPAAA78836-1 | |
| REGION | 1342 | 295 | C | | Inserted PCR product |
| REGION | 1343 | 1360 | | | 'Polylinker |
| REGION | 1343 | 1343 | | | 'TOPO cloning site |
| MARKER | 1395 | | C | T7 | |
| REGION | 1403 | 1418 | | M13 | |
| GENE | 2207 | 3001 | | KanR | |
| GENE | 3205 | 4065 | | AmpR | |
| REGION | 4210 | 4883 | | pUC ori | |

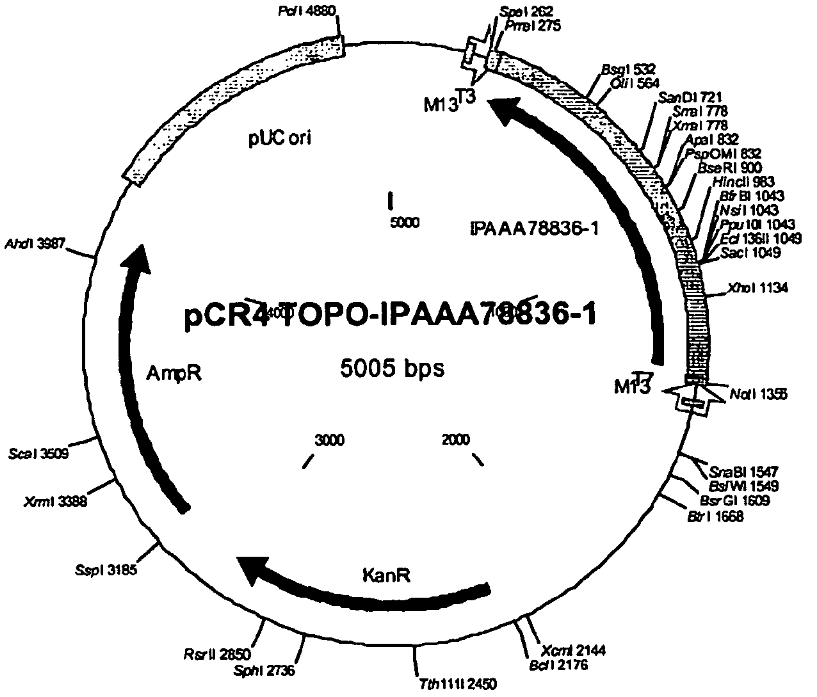

FIGURE 10

```
           78836-FL2-F
   1  TTCTACCATG GAGGGTGTAG GGGGTCTCTG GCCTTGGGTG CTGGGTCTGC TCTCCTTGCC
                m  e  g  v  g  g  l  w  p  w  v  l  g  l  l  s  l

  61  AGGTGTGATC CTAGGAGCGC CCCTGGCCTC CAGCTGCGCA GGAGCCTGTG GTACCAGCTT
      p  g  v  i  l  g  a  p  l  a  s  s  c  a  g  a  c  g  t  s

 121  CCCAGATGGC CTCACCCCTG AGGGAACCCA GGCCTCCGGG GACAAGGACA TTCCTGCAAT
      f  p  d  g  l  t  p  e  g  t  q  a  s  g  d  k  d  i  p  a

 181  TAACCAAGGG CTCATCCTGG AAGAAACCCC AGAGAGCAGC TTCCTCATCG AGGGGGACAT
      i  n  q  g  l  i  l  e  e  t  p  e  s  s  f  l  i  e  g  d

 241  CATCCGGCCG AGTCCCTTCC GACTGCTGTC AGCAACCAGC AACAAATGGC CCATGGGTGG
      i  i  r  p  s  p  f  r  l  l  s  a  t  s  n  k  w  p  m  g

 301  TAGTGGTGTC GTGGAGGTCC CCTTCCTGCT CTCCAGCAAG TACGATGAGC CCAGCCGCCA
      g  s  g  v  v  e  v  p  f  l  l  s  s  k  y  d  e  p  s  r

 361  GGTCATCCTG GAGGCTCTTG CGGAGTTTGA ACGTTCCACG TGCATCAGGT TTGTCACCTA
      q  v  i  l  e  a  l  a  e  f  e  r  s  t  c  i  r  f  v  t

 421  TCAGGACCAG AGAGACTTCA TTTCCATCAT CCCCATGTAT GGGTGCTTCT CGAGTGTGGG
      y  q  d  q  r  d  f  i  s  i  i  p  m  y  g  c  f  s  s  v

 481  GCGCAGTGGA GGGATGCAGG TGGTCTCCCT GGCGCCCACG TGTCTCCAGA AGGGCCGGGG
      g  r  s  g  g  m  q  v  v  s  l  a  p  t  c  l  q  k  g  r

 541  CATTGTCCTT CATGAGCTCA TGCATGTGCT GGGCTTCTGG CACGAGCACA CGCGGGCCGA
      g  i  v  l  h  e  l  m  h  v  l  g  f  w  h  e  h  t  r  a

 601  CCGGGACCGC TATATCCGTG TCAACTGGAA CGAGATCCTG CCAGGCTTTG AAATCAACTT
      d  r  d  r  y  i  r  v  n  w  n  e  i  l  p  g  f  e  i  n

 661  CATCAAGTCT CGGAGCAGCA ACATGCTGAC GCCCTATGAC TACTCCTCTG TGATGCACTA
      f  i  k  s  r  s  s  n  m  l  t  p  y  d  y  s  s  v  m  h

 721  TGGGAGGCTC GCCTTCAGCC GGCGTGGGCT GCCCACCATC ACACCACTTT GGGCCCCCAG
      y  g  r  l  a  f  s  r  r  g  l  p  t  i  t  p  l  w  a  p

 781  TGTCCACATC GGCCAGCGAT GGAACCTGAG TGCCTCGGAC ATCACCCGGG TCCTCAAACT
      s  v  h  i  g  q  r  w  n  l  s  a  s  d  i  t  r  v  l  k

 841  CTACGGCTGC AGCCCAAGTG GCCCCAGGCC CCGTGGGAGA GGGTCCCATG CCCACAGCAC
      l  y  g  c  s  p  s  g  p  r  p  r  g  r  g  s  h  a  h  s

 901  TGGTAGGAGC CCCGCTCCGG CCTCCCTATC TCTGCAGCGG CTTTTGGAGG CACTGTCGGC
      t  g  r  s  p  a  p  a  s  l  s  l  q  r  l  l  e  a  l  s

 961  GGAATCCAGG AGCCCCGACC CCAGTGGTTC CAGTGCGGGA GGCCAGCCCG TTCCTGCAGG
      a  e  s  r  s  p  d  p  s  g  s  s  a  g  g  q  p  v  p  a

1021  GCCTGGGGAG AGCCCACATG GGTGGGAGTC CCCTGCCCTG AAAAAGCTCA GTGCAGAGGC
      g  p  g  e  s  p  h  g  w  e  s  p  a  l  k  k  l  s  a  e
```

FIGURE 10 (continued)

```
1081  CTCGGCAAGG CAGCCTCAGA CCCTAGCTTC CTCCCCAAGA TCAAGGCCTG GAGCAGGTGC
       a  s  a  r   q  p  q   t  l  a   s  s  p  r   s  r  p   g  a  g

1141  CCCCGGTGTT GCTCAGGAGC AGTCCTGGCT GGCCGGAGTG TCCACCAAGC CCACAGTCCC
       a  p  g  v   a  q  e   q  s  w   l  a  g  v   s  t  k   p  t  v

1201  ATCTTCAGAA GCAGGAATCC AGCCAGTCCC TGTCCAGGGA AGCCCAGCTC TGCCAGGGGG
       p  s  s  e   a  g  i   q  p  v   p  v  q  g   s  p  a   l  p  g

1261  CTGTGTACCT AGAAATCATT TCAAGGGGAT GTCCGAAGAT TAAGCCTGTG GCT
       g  c  v  p   r  n  h   f  k  g   m  s  e  d
                                                    78836-FL-R
```

FIGURE 11

```
Query= INSP005b
        (431 letters)

Database: All non-redundant GenBank CDS
translations+PDB+SwissProt+PIR+PRF
          1,247,039 sequences; 397,579,747 total letters

Searching..................................................done

                                                                Score     E
Sequences producing significant alignments:                     (bits)  Value

ref|XP_141346.1| similar to hatching enzyme EHE7 [Anguilla japon...   540   e-152
dbj|BAB68513.1| hatching enzyme EHE4 [Anguilla japonica]             198   1e-49
dbj|BAB68518.1| hatching enzyme EHE13 [Anguilla japonica]            198   1e-49
dbj|BAB68516.1| hatching enzyme EHE10 [Anguilla japonica]            197   3e-49
dbj|BAB68515.1| hatching enzyme EHE7 [Anguilla japonica]             196   4e-49
dbj|BAB68514.1| hatching enzyme EHE6 [Anguilla japonica]             196   7e-49
dbj|BAB68517.1| hatching enzyme EHE12 [Anguilla japonica]            194   3e-48
dbj|BAB68519.1| hatching enzyme EHE14 [Anguilla japonica]            191   1e-47
pir||C48826 high choriolytic hatching proteinase (EC 3.4.24.-) H...   187   3e-46
dbj|BAA12146.1| choriolysin H [Oryzias latipes]                      186   4e-46
```

Top alignment to known metalloproteinase:

```
>dbj|BAB68518.1| hatching enzyme EHE13 [Anguilla japonica]
          Length = 271

 Score =  198 bits (503), Expect = 1e-49
 Identities = 103/233 (44%), Positives = 144/233 (61%), Gaps = 5/233 (2%)

Query: 52  DKDIPAINQGLILEETPESSFLIEGDIIRPSPFRLLSATSNK--WPMGGSGVVEVPFLLS 109
            D D   I   ++       S  L+EGD++  +    ++  +N+  W     G+VEVP+ +S
Sbjct: 41  DPDDLDITARILQSNNGSSEILMEGDMVVSNTRNAINCWNNQCLWRKSSDGLVEVPYTVS 100

Query: 110 SKYDEPSRQVILEALAEFERSTCIRFVTYQDQRDFISIIPMYGCFSSVGRSGGMQVVSLA 169
            S++     ++ I  A+  F   TCIRFV    QRDFISI    GC+S +GR+GG QVVSLA
Sbjct: 101 SEFSYYHKKRIENAMETFNTETCIRFVPRSSQRDFISIESRDGCYSYLGRTGGKQVVSLA 160

Query: 170 PT-CLQKGRGIVLHELMHVLGFWHEHTRADRDRYIRVNWNEILPGFEINFIKSRSSNMLT 228
               C+    GI+ HEL H LGF+HEHTR+DRD Y+++NW   + P    NF +  ++N+ T
Sbjct: 161 RYGCVY--HGIIQHELNHALGFYHEHTRSDRDEYVKINWENVAPHTIYNFQEQDTNNLNT 218

Query: 229 PYDYSSVMHYGRLAFSRRGLPTITPLWAPSVHIGQRWNLSASDITRVLKLYGC 281
            PYDY+S+MHYGR AFS  G+ TITP+  P+  IGQR ++S  DI R+ KLY C
Sbjct: 219 PYDYTSIMHYGRTAFSTNGMDTITPVPNPNQSIGQRRSMSKGDILRINKLYSC.
```

FIGURE 12

Molecule: pCR4 TOPO-IPAAA78836-2, 5269 bps DNA Circular
File Name: 13296.cm5, dated 24 Oct 2002

Description: Ligation of inverted IPAAA78836v2 into pCR4-TOPO linear vector*

Molecule Features:

| Type | Start | End | | Name | Description |
|---|---|---|---|---|---|
| REGION | 205 | 221 | | M13 | rev priming site |
| MARKER | 243 | | | T3 | |
| REGION | 262 | 294 | | | Polylinker' |
| REGION | 294 | 294 | | | TOPO cloning site' |
| GENE | 1600 | 307 | C | IPAAA78836-2 | |
| REGION | 1607 | 1624 | | | 'Polylinker |
| REGION | 1607 | 1607 | | | 'TOPO cloning site |
| MARKER | 1659 | | C | T7 | |
| REGION | 1667 | 1682 | | M13 | |
| GENE | 2471 | 3265 | | KanR | |
| GENE | 3469 | 4329 | | AmpR | |
| REGION | 4474 | 5147 | | pUC ori | |

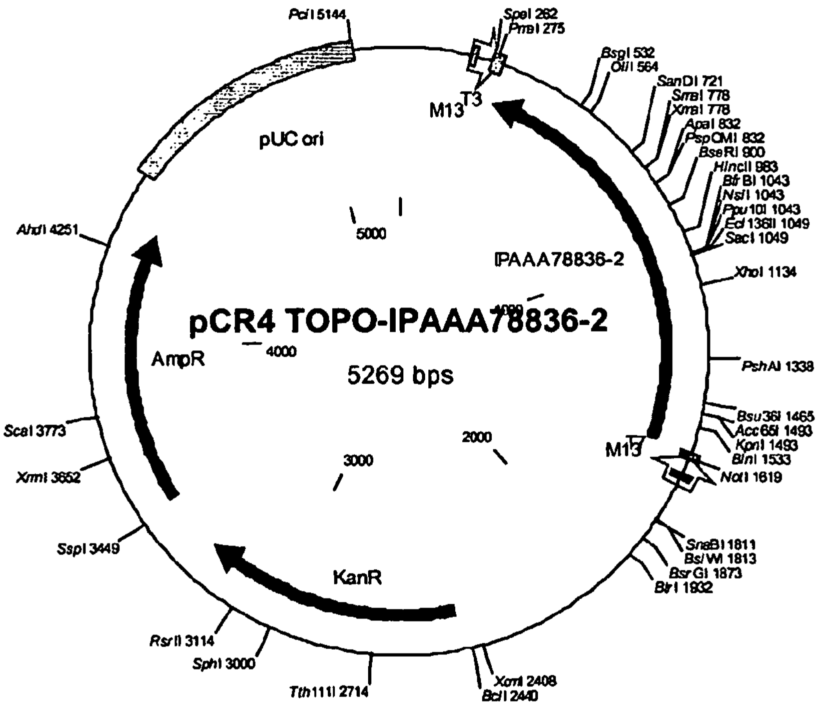

FIGURE 13

Active site residues are underlined below.

```
WO2002/16566-A2      -----MEGVGGLWPWVLGLLSLPGVILGAPLASSCAGACGTSFPDGLTPEGTQASGDKDI
AX526191             MSCCLVSPVGAPGICVCPCLSGPGVILGAPLASSCAGACGTSFPDGLTPEGTQASGDKDI
INSP005 PREDICTION   ------------------------------------------------------------
INSP005b             -----MEGVGGLWPWVLGLLSLPGVILGAPLASSCAGACGTSFPDGLTPEGTQASGDKDI
INSP005a             ------------------------------------------------------------


WO2002/16566-A2      PAINQGLILEETPESSFLIEGDIIRPSPFRLLSATSNKWPMGGSGVVEVPFLLSSKYDEP
AX526191             PAINQGLILEETPESSFLIEGDIIRPSPFRLLSATSNKWPMGGSGVVEVPFLLSSKYDEP
INSP005 PREDICTION   --------------------------------------WPMGGSGVVEVPFLLSSKYDEP
INSP005b             PAINQGLILEETPESSFLIEGDIIRPSPFRLLSATSNKWPMGGSGVVEVPFLLSSKYDEP
INSP005a             ----------------------------------------MGGSGVVEVPFLLSSKYDEP
                                                             ********************

WO2002/16566-A2      SRQVILEALAEFERSTCIRFVTYQDQRDFISIIPMYGCFSSVGRSGGMQVVSLAPTCLQK
AX526191             SRQVILEALAEFERSTCIRFVTYQDQRDFISIIPMYGCFSSVGRSGGMQVVSLAPTCLQK
INSP005 PREDICTION   SHQVILEALAEFERSTCIRFVTYQDQRDFISIIPMYGCFSSVGRSGGMQVVSLAPTCLQK
INSP005b             SRQVILEALAEFERSTCIRFVTYQDQRDFISIIPMYGCFSSVGRSGGMQVVSLAPTCLQK
INSP005a             SRQVILEALAEFERSTCIRFVTYQDQRDFISIIPMYGCFSSVGRSGGMQVVSLAPTCLQK
                     *:**********************************************************

WO2002/16566-A2      GRGIVLHELMHVLGFWHEHTRADRDRYIRVNWNEILPGFEINFIKSRSSNMLTPYDYSSV
AX526191             GRGIVLHELMHVLGFWHEHTRADRDRYIRVNWNEILPGFEINFIKSRSSNMLTPYDYSSV
INSP005 PREDICTION   GRGIVLHELMHVLGFWHEHTRADRDRYIRVNWNEILPGFEINFIKSQSSNMLTPYDYSSV
INSP005b             GRGIVLHELMHVLGFWHEHTRADRDRYIRVNWNEILPGFEINFIKSRSSNMLTPYDYSSV
INSP005a             GRGIVLHELMHVLGFWHEHTRADRDRYIRVNWNEILPGFEINFIKSQSSNMLTPYDYSSV
                     **********************************************:*************

WO2002/16566-A2      MHYGRLAFSRRGLPTITPLWAPSVHIGQRWNLSASDITRVLKLYGCSPSGPRPRGRG---
AX526191             MHYGRLAFSRRGLPTITPLWAPSVHIGQRWNLSASDITRVLKLYGCSPSGPRPRGRGSHA
INSP005 PREDICTION   MHYGRLAFSRRGLPTITPLWAPSVHIGQRWNLSASDITRVLKLYGC--------------
INSP005b             MHYGRLAFSRRGLPTITPLWAPSVHIGQRWNLSASDITRVLKLYGCSPSGPRPRGRGSHA
INSP005a             MHYGRLAFSRRGLPTITPLWAPSVHIGQRWNLSASDITRVLKLYGCSPSGPRPRGRGSHA
                     **********************************************:.:.. . . .: :
```

FIGURE 13 (continued)

```
WO2002/16566-A2       -------------------------------------------------EWHG---RKVT
AX526191              HSTGRSPAPASLSLQRLLEALSAESRSPDPSGSSAGGQPVPAGPGESPHGWESPALKKLS
INSP005 PREDICTION    ------------------------------------------------------------
INSP005b              HSTGRSPAPASLSLQRLLEALSAESRSPDPSGSSAGGQPVPAGPGESPHGWESPALKKLS
INSP005a              HSTGRSPAPASLSLQRLLEALSAESRSPDPSGSSAGGQPVPAGPGESPHGWESPALKKLS
                       ::. :.:.:: : .   .: ::.: :...:.:::.... .:....:.    ..:  . :

WO2002/16566-A2       ------------------------------------------------------------
AX526191              AEASARQPQTLASSPRSRPGAGAPGVAQEQSWLAGVSTKPTVPSSEAGIQPVPVQGSPAL
INSP005 PREDICTION    ------------------------------------------------------------
INSP005b              AEASARQPQTLASSPRSRPGAGAPGVAQEQSWLAGVSTKPTVPSSEAGIQPVPVQGSPAL
INSP005a              AEASARQPQTLASSPRSRPGAGAPGVAQEQSWLAGVSTKPTVPSSEAGIQPVPVQGSPAL
                      :.::: ...: :::. : ..:.:.. :...:  :. ::..: .::.:. .. . ..:.:

WO2002/16566-A2       ----------------
AX526191              PGGCVPRNHFKGMSED
INSP005 PREDICTION    ----------------
INSP005b              PGGCVPRNHFKGMSED
INSP005a              PGGCVPRNHFKGMSED
                      .... . .  .. :..
```

FIGURE 14
>INSP005b
SignalP-NN result:
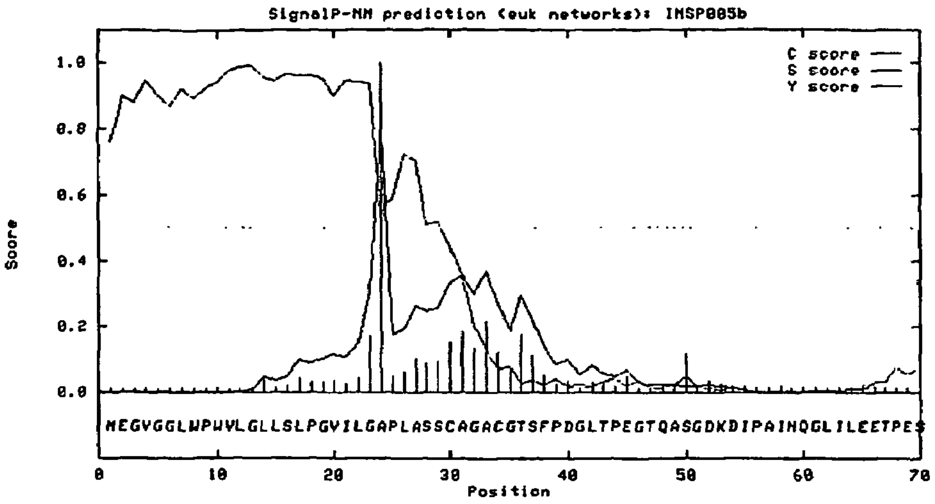
data
```
>INSP005b              length = 70
Measure  Position  Value  Cutoff  signal peptide?
  max. C    24       1.000   0.33   YES
  max. Y    24       0.789   0.32   YES
  max. S    13       0.991   0.82   YES
  mean S     1-23    0.929   0.47   YES
Most likely cleavage site between pos. 23 and 24: ILG-AP
```
SignalP-HMM result:
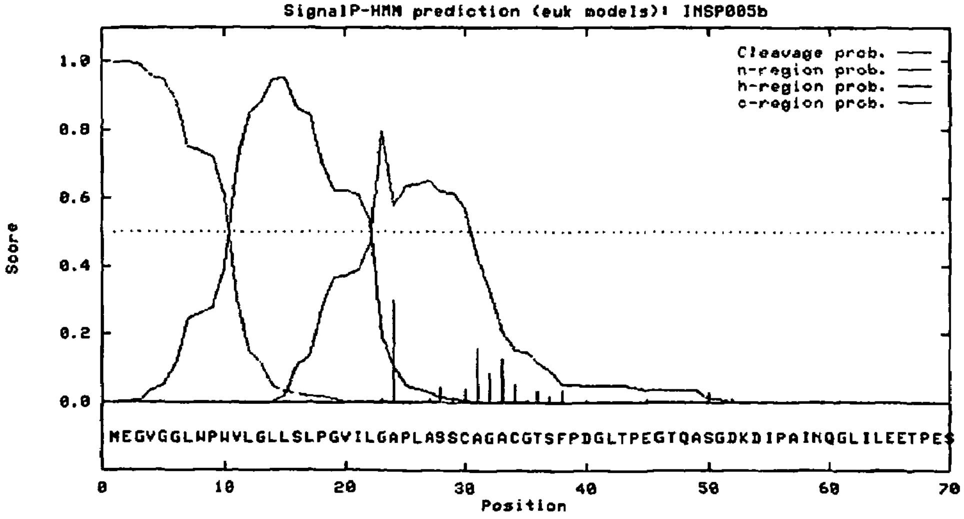
data
```
>INSP005b
Prediction: Signal peptide
Signal peptide probability: 0.996
Signal anchor probability: 0.003
Max cleavage site probability: 0.302 between pos. 23 and 24
```

METALLOPROTEASE PROTEINS

CROSS-REFERENCE TO RELATED APPLICATION

This application is the National Stage of International Application Number PCT/GB2003/005664, filed Dec. 23, 2003, which is hereby incorporated by reference herein in its entirety, including any figures, tables, nucleic acid sequences, amino acid sequences, or drawings.

This invention relates to novel proteins, termed INSP005a and INSP005b, herein identified as secreted proteins, in particular members of the metalloprotease family and to the use of these proteins and nucleic acid sequences from the encoding genes in the diagnosis, prevention and treatment of disease.

All publications, patents and patent applications cited herein are incorporated in full by reference.

BACKGROUND

The process of drug discovery is presently undergoing a fundamental revolution as the era of functional genomics comes of age. The term "functional genomics" applies to an approach utilising bioinformatics tools to ascribe function to protein sequences of interest. Such tools are becoming increasingly necessary as the speed of generation of sequence data is rapidly outpacing the ability of research laboratories to assign functions to these protein sequences.

As bioinformatics tools increase in potency and in accuracy, these tools are rapidly replacing the conventional techniques of biochemical characterisation. Indeed, the advanced bioinformatics tools used in identifying the present invention are now capable of outputting results in which a high degree of confidence can be placed.

Various institutions and commercial organisations are examining sequence data as they become available and significant discoveries are being made on an on-going basis. However, there remains a continuing need to identify and characterise further genes and the polypeptides that they encode, as targets for research and for drug discovery.

SECRETED PROTEIN BACKGROUND

The ability for cells to make and secrete extracellular proteins is central to many biological processes. Enzymes, growth factors, extracellular matrix proteins and signalling molecules are all secreted by cells. This is through fusion of a secretory vesicle with the plasma membrane. In most cases, but not all, proteins are directed to the endoplasmic reticulum and into secretory vesicles by a signal peptide. Signal peptides are cis-acting sequences that affect the transport of polypeptide chains from the cytoplasm to a membrane bound compartment such as a secretory vesicle. Polypeptides that are targeted to the secretory vesicles are either secreted into the extracellular matrix or are retained in the plasma membrane. The polypeptides that are retained in the plasma membrane will have one or more transmembrane domains. Examples of secreted proteins that play a central role in the functioning of a cell are cytokines, hormones, extracellular matrix proteins (adhesion molecules), proteases, and growth and differentiation factors. Description of some of the properties of these proteins follows.

Proteases are enzymes that irreversibly hydrolyse amide bonds in peptides and proteins. Proteases are widely distributed and are involved in many different biological processes, from activation of proteins and peptides to degradation of proteins. Despite the fact that proteases have been shown to be involved in many different diseases, drugs targeted to proteases are still rare in pharmacy, although inhibitors of angiotensin converting enzyme (ACE) have been among the most successful antihypertensive drugs for several years. Proteases have recently received substantial publicity as valuable therapeutic targets following the approval of HIV protease inhibitors.

Proteases can be divided in large Families. The term "Family" is used to describe a group of proteases in which each member shows an evolutionary relationship to at least one other member, either throughout the whole sequence or at least in the part of the sequence responsible for catalytic activity. The name of each Family reflects the catalytic activity type of the proteases in the Family. Thus, serine proteases belong to the S family, threonine proteases belong to the T family, aspartyl proteases belong to the A family, cysteine proteases belong to the C family and metalloproteinases belong to the M family. Metalloproteases and Serine proteases are commonly found in the extracellular matrix.

Metalloproteases (M Family):

Metalloproteases can be divided in 2 major groups depending on the presence or absence of a the Zinc binding motif (HEXXH).

1.1 Presence of HEXXH motif(22 families): Prosite number: PDOC00129

Families with Interesting Members:

M2: Peptidyl-dipeptidase A (Angiotensin I Converting Enzyme: ACE)

M13: Neprilysin (Enkephalinase A=neutral endopeptidase=NEP), Endothelial Converting Enzyme (ECE)

M10B: Matrixin (Matrix Metalloproteases=MMPs)

M12B: Reprolysin (ADAM-10; ADAM-17=TNF-alpha Converting Enzyme=TACE)/Desintegrin (other ADAM proteases). The ADAMs are a large, widely expressed and developmentally regulated family of proteins with multiple potential functions in cell-cell and cell-matrix interactions. Among them TACE represents a new emerging target for arthritis disease.

M41: This family contains ATP-dependent metalloproteases: FtsH, proteasome proteins.

One of the largest therapeutically interesting group of metalloproteinases is the Matrix Metalloproteinases family (MMPs). Matrix metalloproteinases are a family of Zinc containing enzymes that are responsible for the remodeling of extracellular matrix throughout the body. They have been shown to be involved in cancer (increase invasiveness, effects on new blood vessel), and in arthritis (involvement in cartilage degradation (Dahlberg, L., et al., Arthritis Rheum. 2000 43(3):673-82) and also TNF-alpha conversion (Hanemaaijer, R., et al., J Biol Chem. 1997 272(50):31504-9, Shlopov, B. V., et al., Arthritis Rheum. 1997 40(11):2065-74)). Indeed, different MMPs have been shown to be overexpressed in diseases such as arthritis (Seitz, M., et al., Rheumatology (Oxford). 2000 39(6):637-645, Yoshihara, Y., et al., Ann Rheum Dis. 2000 59(6):455-61, Yamanaka, H., et al., Lab Invest. 2000 80(5):677-87, Jovanovic, D. V., et al., Arthritis Rheum. 2000 May; 43(5):1134-44, Ribbens, C., et al., J Rheumatol.

2000 27(4):888-93) and cancer (Sakamoto, Y., et al., Int J Oncol. 2000 17(2):237-43, Kerkela, E., et al., J Invest Dermatol. 2000 114(6):1113-9, Fang, J., et al., Proc Natl Acad Sci USA. 2000 97(8):3884-9, Sun, Y., et al., J Biol Chem. 2000 275(15):11327-32, McCawley, L. J., et al., Mol Med Today. 2000 6(4):149-56, Ara, T., et al., J Pediatr Surg. 2000 35(3):432-7, Shigemasa, K., et al., Med Oncol. 2000 17(1):52-8, Nakanishi, K., et al., Hum Pathol. 2000 31(2):193-200, Dalberg, K., et al., World J Surg. 2000 24(3):334-40). Inhibitors of these enzymes have been suggested as potential therapeutic agents for the use in the treatment of both cancer and arthritis. More recently it has been shown that MMPs may also have a role in the release of soluble cytokine receptors, growth factors and other cell mediators, suggesting that selective MMPs inhibitors may have wider therapeutic applications than previously proposed.

MMPs have been divided in 4 families based on amino-acid sequence homologies of their domain structure, other than the catalytic region.

Minimal domain family: matrilysin (PUMP-1, MMP-7) cleaves proteoglycan, laminin and fibronectin Hemopexin domain family:
 Collagenases: unique ability to cleave fibrillar collagen. The role of collagenases in cartilage degradation, make them attractive targets for the treatment of rheumatoid and osteoarthritis.
  collagenases fibroblast collagenase (interstitial collagenase, MMP-1)
  neutrophil collagenase (MMP-8)
  collagenase-3 (MMP-13)
  Metalloelastase: MME (MMP-12)
 Stromelysin-1 (MMP-3), 2 (MMP-10) and 3 (MMP-11). MMP-11 is excreted as an active form and it's function could be to activate other MMPs.

Fibronectin domain family: degrades a large number of matrix substrates (gelatin, elastin, type IV collagen)
 Gelatinase A (MMP-2); beside it's involvement in cancer (tumor invasiveness), it is proposed as a potential target for the discovery of antiplatelet agent as it may play an important role in platelet activation.
 Gelatinase B (MMP-9)
Transmembrane domain family:
MT-1-MMP, MT-4-MMP, MMP-14, MMP-17
 A lot of studies concerning the different specificities of MMPs and their relative involvement in some diseases are on going.

1.2 Absence of HEXXH motifs (18 families):
Families with interesting members:
M24A: Methionyl aminopeptidase, type 1 (including procaryotic and eucaryotic MAP-1)/Prosite number: PDOC00575
M24C: Methionyl aminopeptidase, type 2 (including eucaryotic MAP-2)/Prosite number: PDOC00575

TABLE 1

Summary of metalloproteases and their function

| Protease name | EC number | Biological function | Disease associated | Regulation |
|---|---|---|---|---|
| MMP-12 | 3.4.24.65 | MMPs function; elastin degradation; process TNF-alpha; convert plasminogen to angiotensin | involvement in lung disorders, emphyscma, cystic fibrosis | enhanced expression in some skin diseases |
| MMP-2 | 3.4.24.24 | MMPs function | cancer | overexpression in colorectal cancer |
| ADAM-12 | 3.4.24 | cell-cell, cell-matrix interaction | | up-regulated in several human carcinomas |
| TACE | 3.4.24.? | Processing of the membrane bound TNF-alpha and other cell bound molecule | inflammation, rheumatoid arthritis, neuroimmunological diseases | up-regulated in arthritis affected cartilage |
| ACE | 3.4.15.1 | production of angiotensin II | hypertension | |
| ECE-1 | 3.4.24.71 | process the precursor of the vasoconstrictor endothelin | cardiovascular | |
| NEP | 3.4.24.11 | cleaves neuropeptides, hormones and immune mediator | cardiovascular, arthritis (?) | |
| FtsH | ? | protein secretion, assembly, degradation, cell cycle, stress response | bacterial infections | — |
| Deformylase | 3.5.1.31 | removes the formyl group from N-terminal from newly synthesized proteins | bacterial infections | — |
| Proteasome | 3.4.99.46 | protein degradation, antigen presentation | cancer | |

Metalloproteases are implicated across a wide variety of therapeutic areas. These include respiratory diseases (Segura-Valdez, L., et al., Chest. 2000 117(3):684-94, Tanaka, H., et al., J Allergy Clin Immunol. 2000 105(5):900-5, Hoshino, M., et al., J Allergy Clin Immunol. 1999 104(2 Pt 1):356-63, Mautino, G., et al., Am J Respir Crit Care Med. 1999 160(1):324-30, Dalal, S., et al., Chest. 2000 117(5 Suppl 1):227S-8S, Ohnishi, K., et al., Lab Invest. 1998 78(9):1077-87), cardiovascular disease (Taniyama, Y., et al., Circulation. 2000 102(2):246-52, Hong, B. K., et al., Yonsei Med J. 2000 41(1):82-8, Galis, Z. S., et al., Proc Natl Acad Sci USA. 1995 92(2):402-6), bacterial infections (Scozzafava, A., et al., J Med Chem. 2000 43(9):1858-65, Vencill, C. F., et al., Biochemistry. 1985 24(13):3149-57, Steinbrink, D. R, et al., J Biol Chem. 1985 260(5):2771-6, Lopez-Boado, Y. S., et al., J Cell Biol. 2000 148(6):1305-15, Chang, J. C., et al., Thorax. 1996

51(3):306-1 1, Dammann, T., et al., Mol. Microbiol. 6:2267-2278 (1992), Wassif, C., et al., J. Bacteriol. 177 (20), 5790-5798 (1995), oncology (Sakamoto, Y., et al., Int J Oncol. 2000 17(2):237-43, Kerkela, E., et al., J Invest Dermatol. 2000 114(6):1113-9, Fang, J., et al., Proc Natl Acad Sci USA. 2000 97(8):3884-9, Sun, Y., et al., J Biol Chem. 2000 275(15): 11327-32, McCawley, L. J., et al., Mol Med Today. 2000 6(4):149-56, Ara, T., et al., J Pediatr Surg. 2000 35(3):432-7, Shigemasa, K., et al., Med Oncol. 2000 17(1):52-8, Nakanishi, K., et al., Hum Pathol. 2000 31(2):193-200, Dalberg, K., et al., World J Surg. 2000 24(3):334-40), and inflammation (rheumatoid and osteo-arthritis (Ribbens, C., et al., J Rheumatol. 2000 27(4):888-93, Kageyama, Y., et al., Clin Rheumatol. 2000 19(1):14-20, Shlopov, B. V., et al., Arthritis Rheum. 2000 January; 43(1):195-205)).

Metalloproteases are also implicated in the physiology and pathology of sexual reproduction, and have been implicated in therapies associated with modulating chorion status, the zona reaction, the formation of fertilisation membranes, contraception and infertility (Shibata et al. (2000) J. Biol. Chem vol. 275, No. 12 p 8349)

Accordingly, identification of novel metalloproteases is of extreme importance in increasing understanding of the underlying pathways that lead to certain disease states in which these proteins are implicated, and in developing more effective gene or drug therapies to treat these disorders.

THE INVENTION

The invention is based on the discovery that the INSP005a and INSP005b proteins function as secreted protease molecules and moreover as secreted protease molecules of the metalloprotease family. Preferably, the INSP005a and INSP005b proteins are members of the choriolysin/astacin-like family of metalloproteases.

In one embodiment of the first aspect of the invention, there is provided a polypeptide which:

(i) comprises the amino acid sequence as recited in SEQ ID NO:14;

(ii) is a fragment thereof having function as a secreted protein of the metalloprotease class or having an antigenic determinant in common with the polypeptides of (i); or (iii) is a functional equivalent of (i) or (ii).

Preferably, a polypeptide according to this embodiment consists of the sequence recited in SEQ ID NO:14. The polypeptide having the sequence recited in SEQ ID NO:14 is referred to hereafter as "the INSP005a polypeptide".

In a second embodiment of the first aspect of the invention, there is provided a polypeptide which:

(i) comprises the amino acid sequence as recited in SEQ ID NO:34 or SEQ ID NO:36;

(ii) is a fragment thereof having function as a secreted protein of the metalloprotease class or having an antigenic determinant in common with the polypeptides of (i); or (iii) is a functional equivalent of (i) or (ii).

Preferably, a polypeptide according to this embodiment consists of the sequence recited in SEQ ID NO:34 or SEQ ID NO:36. The polypeptide having the sequence recited in SEQ ID NO:34 is referred to hereafter as "the INSP005b polypeptide".

Although the Applicant does not wish to be bound by this theory, it is postulated that the first 23 amino acids of the INSP005b polypeptide form a signal peptide. The nucleotide sequence encoding the postulated INSP005b mature polypeptide, and the amino acid sequence of the INSP005b mature polypeptide, are recited in SEQ ID NO:35 and SEQ ID NO:36, respectively. The polypeptide having the sequence recited in SEQ ID NO:36 is referred to hereafter as "the INSP005b mature polypeptide".

Preferably, a polypeptide according to the above-described aspects of the invention functions as a metalloprotease. The term "metalloprotease" is well understood in the art and the skilled worker will readily be able to ascertain metalloprotease activity using one of a variety of assays known in the art. For example, two commonly-applied assays are the quantitative [$^3$H] gelatin assay (Martin et al., Kidney Int. 36, 790-801) and the gelatin zymography assay (Herron G. S. et al., J. Biol. Chem. 1986, 261, 2814-2818).

More preferably, a polypeptide according to the above-described aspects of the invention is a member of the choriolysin/astacin-like family of metalloproteases.

Evidence is presented in the Examples section below that delivery of INSP005b cDNA (also referred to herein as IPAAA78836-2) in an in vivo model of fulminant hepatitis was found to decrease TNF-alpha and m-IL-6 levels in serum and had a significant effect on the reduction of transaminases measured in serum.

The decrease in aspartate aminotransferase (ASAT) and alanine aminotransferase (ALAT) levels noted might be due to decreased TNF-alpha and IL-6 levels. TNF-alpha is an important cytokine involved in liver damage after ConA injection. In this mouse model of liver hepatitis, TNF-alpha is mainly produced by hepatic macrophages, the so-called Kupfer cells. Anti TNF-alpha antibodies have been shown to confer protection against disease (Seino et al. 2001, Annals of surgery 234, 681). Accordingly, it is considered that INSP005b polypeptide and related functionally equivalent proteins will be useful in treating auto-immune, viral or acute liver diseases as well as alcoholic liver failures. They are likely also to be effective in treating other inflammatory diseases.

The INSP005a polypeptides, INSP005b polypeptides and the INSP005b mature polypeptides are referred to herein as "the INSP005 polypeptides".

In a second aspect, the invention provides a purified nucleic acid molecule which encodes a polypeptide of the first aspect of the invention. Preferably, the purified nucleic acid molecule has the nucleic acid sequence as recited in SEQ ID NO:13 (encoding the INSP005a polypeptide), SEQ ID NO:33 (encoding the INSP005b polypeptide) or SEQ ID NO:35 (encoding the INSP005b mature polypeptide), or is a redundant equivalent or fragment of either of these sequences.

In a third aspect, the invention provides a purified nucleic acid molecule which hydridizes under high stringency conditions with a nucleic acid molecule of the second aspect of the invention.

In a fourth aspect, the invention provides a vector, such as an expression vector, that contains a nucleic acid molecule of the second or third aspect of the invention. In a preferred embodiment of this aspect of the invention the vector is the PCR-TOPO-IPAAA78836-1 vector (see FIG. 9 and SEQ ID NO:38). In a further preferred embodiment of this aspect of the invention the vector is the PCR-TOPO-IPAAA78836-2 vector (see FIG. 12 and SEQ ID NO:39).

In a fifth aspect, the invention provides a host cell transformed with a vector of the fourth aspect of the invention.

In a sixth aspect, the invention provides a ligand which binds specifically to, and which preferably inhibits the metalloprotease activity of a polypeptide of the first aspect of the invention. Ligands to a polypeptide according to the invention may come in various forms, including natural or modified substrates, enzymes, receptors, small organic molecules such as small natural or synthetic organic molecules of up to 2000

Da, preferably 800 Da or less, peptidomimetics, inorganic molecules, peptides, polypeptides, antibodies, structural or functional mimetics of the aforementioned.

In a seventh aspect, the invention provides a compound that is effective to alter the expression of a natural gene which encodes a polypeptide of the first aspect of the invention or to regulate the activity of a polypeptide of the first aspect of the invention.

A compound of the seventh aspect of the invention may either increase (agonise) or decrease (antagonise) the level of expression of the gene or the activity of the polypeptide. Importantly, the identification of the function of the INSP005 polypeptides allows for the design of screening methods capable of identifying compounds that are effective in the treatment and/or diagnosis of disease. Ligands and compounds according to the sixth and seventh aspects of the invention may be identified using such methods. These methods are included as aspects of the present invention.

Evidence is presented in the Examples section below that the INSP005b polypeptide may be used to prevent or treat inflammatory diseases, auto-immune diseases, liver disease or liver failure. Accordingly, the provision of a compound according to the seventh aspect of the invention which mimics the INSP005b polypeptide conformationally, or is an agonist of the INSP005b polypeptide is particularly preferred since such a compound may find utility in the prevention or treatment of an inflammatory disease, an auto-immune disease, liver disease or liver failure as described above.

In an eighth aspect, the invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in therapy or diagnosis of diseases in which metalloproteases are implicated. These molecules may also be used in the manufacture of a medicament for the treatment of such diseases, particularly respiratory disorders, including emphysema and cystic fibrosis, metabolic disorders, cardiovascular disorders, bacterial infections, hypertension, proliferative disorders, including cancer, autoimmune/inflammatory disorders, including rheumatoid arthritis, neurological disorders, developmental disorders and reproductive disorders. These moieties of the first, second, third, fourth, fifth, sixth or seventh aspect of the invention may also be used in the manufacture of a medicament for the treatment of such diseases.

It is particularly preferred that the moieties of the first, second, third, fourth, fifth and sixth aspects of the invention are used in the manufacture of a medicament for the treatment of inflammatory diseases, autoimmune diseases, liver disease (including viral or acute liver disease) and liver failure (including alcoholic liver failure).

In a ninth aspect, the invention provides a method of diagnosing a disease in a patient, comprising assessing the level of expression of a natural gene encoding a polypeptide of the first aspect of the invention or the activity of a polypeptide of the first aspect of the invention in tissue from said patient and comparing said level of expression or activity to a control level, wherein a level that is different to said control level is indicative of disease. Such a method will preferably be carried out in vitro. Similar methods may be used for monitoring the therapeutic treatment of disease in a patient, wherein altering the level of expression or activity of a polypeptide or nucleic acid molecule over the period of time towards a control level is indicative of regression of disease.

A preferred disease diagnosed by a method of the ninth aspect of the invention is an inflammatory disease, autoimmune disease, liver disease (including viral or acute liver disease) or liver failure (including alcoholic liver failure).

A preferred method for detecting polypeptides of the first aspect of the invention comprises the steps of: (a) contacting a ligand, such as an antibody, of the sixth aspect of the invention with a biological sample under conditions suitable for the formation of a ligand-polypeptide complex; and (b) detecting said complex.

A number of different such methods according to the ninth aspect of the invention exist, as the skilled reader will be aware, such as methods of nucleic acid hybridization with short probes, point mutation analysis, polymerase chain reaction (PCR) amplification and methods using antibodies to detect aberrant protein levels. Similar methods may be used on a short or long term basis to allow therapeutic treatment of a disease to be monitored in a patient. The invention also provides kits that are useful in these methods for diagnosing disease.

In a tenth aspect, the invention provides for the use of a polypeptide of the first aspect of the invention as a secreted protein, preferably as a metalloprotease.

In an eleventh aspect, the invention provides a pharmaceutical composition comprising a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, in conjunction with a pharmaceutically-acceptable carrier.

In a twelfth aspect, the present invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in the manufacture of a medicament for the diagnosis or treatment of a disease, such as respiratory disorders, including emphysema and cystic fibrosis, metabolic disorders, cardiovascular disorders, bacterial infection, hypertension, proliferative disorders, including cancer, autoimmune/inflammatory disorders, including rheumatoid arthritis, neurological disorders, developmental disorders, reproductive disorders or other diseases in which metalloproteases are implicated.

It is particularly preferred that the moieties of the first, second, third, fourth, fifth and sixth aspects of the invention are used in the manufacture of a medicament for the treatment of an inflammatory disease, an auto-immune disease, liver disease or liver failure.

In a thirteenth aspect, the invention provides a method of treating a disease in a patient comprising administering to the patient a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention.

For diseases in which the expression of a natural gene encoding a polypeptide of the first aspect of the invention, or in which the activity of a polypeptide of the first aspect of the invention, is lower in a diseased patient when compared to the level of expression or activity in a healthy patient, the polypeptide, nucleic acid molecule, vector, host cell, ligand or compound administered to the patient should be an agonist. Conversely, for diseases in which the expression of the natural gene or activity of the polypeptide is higher in a diseased patient when compared to the level of expression or activity in a healthy patient, the polypeptide, nucleic acid molecule, vector, host cell, ligand or compound administered to the patient should be an antagonist. Examples of such antagonists include antisense nucleic acid molecules, ribozymes and ligands, such as antibodies.

It is particularly preferred that the disease is an inflammatory disease, an auto-immune disease, liver disease or liver failure.

In a fourteenth aspect, the invention provides transgenic or knockout non-human animals that have been transformed to express higher, lower or absent levels of a polypeptide of the first aspect of the invention. Such transgenic animals are very useful models for the study of disease and may also be used in screening regimes for the identification of compounds that are effective in the treatment or diagnosis of such a disease.

It is particularly preferred that the disease is an inflammatory disease, an auto-immune disease, liver disease or liver failure.

A summary of standard techniques and procedures which may be employed in order to utilise the invention is given below. It will be understood that this invention is not limited to the particular methodology, protocols, cell lines, vectors and reagents described. It is also to be understood that the terminology used herein is for the purpose of describing particular embodiments only and it is not intended that this terminology should limit the scope of the present invention. The extent of the invention is limited only by the terms of the appended claims.

Standard abbreviations for nucleotides and amino acids are used in this specification.

The practice of the present invention will employ, unless otherwise indicated, conventional techniques of molecular biology, microbiology, recombinant DNA technology and immunology, which are within the skill of those working in the art.

Such techniques are explained fully in the literature. Examples of particularly suitable texts for consultation include the following: Sambrook Molecular Cloning; A Laboratory Manual, Second Edition (1989); DNA Cloning, Volumes I and II (D. N Glover ed. 1985); Oligonucleotide Synthesis (M. J. Gait ed. 1984); Nucleic Acid Hybridization (B. D. Hames & S. J. Higgins eds. 1984); Transcription and Translation (B. D. Hames & S. J. Higgins eds. 1984); Animal Cell Culture (R. I. Freshney ed. 1986); Immobilized Cells and Enzymes (IRL Press, 1986); B. Perbal, A Practical Guide to Molecular Cloning (1984); the Methods in Enzymology series (Academic Press, Inc.), especially volumes 154 & 155; Gene Transfer Vectors for Mammalian Cells (J. H. Miller and M. P. Calos eds. 1987, Cold Spring Harbor Laboratory); Immunochemical Methods in Cell and Molecular Biology (Mayer and Walker, eds. 1987, Academic Press, London); Scopes, (1987) Protein Purification: Principles and Practice, Second Edition (Springer Verlag, N.Y.); and Handbook of Experimental Immunology, Volumes I-IV (D. M. Weir and C. C. Blackwell eds. 1986).

As used herein, the term "polypeptide" includes any peptide or protein comprising two or more amino acids joined to each other by peptide bonds or modified peptide bonds, i.e. peptide isosteres. This term refers both to short chains (peptides and oligopeptides) and to longer chains (proteins).

As described above, the polypeptides of the present invention may be in the form of a mature protein or may be a pre-, pro- or prepro-protein that can be activated by cleavage of the pre-, pro- or prepro-portion to produce an active mature polypeptide. In such polypeptides, the pre-, pro- or prepro-sequence may be a leader or secretory sequence or may be a sequence that is employed for purification of the mature polypeptide sequence.

The polypeptide of the first aspect of the invention may form part of a fusion protein. For example, it is often advantageous to include one or more additional amino acid sequences which may contain secretory or leader sequences, pro-sequences, sequences which aid in purification, or sequences that confer higher protein stability, for example during recombinant production. Alternatively or additionally, the mature polypeptide may be fused with another compound, such as a compound to increase the half-life of the polypeptide (for example, polyethylene glycol).

Polypeptides may contain amino acids other than the 20 gene-encoded amino acids, modified either by natural processes, such as by post-translational processing or by chemical modification techniques which are well known in the art. Among the known modifications which may commonly be present in polypeptides of the present invention are glycosylation, lipid attachment, sulphation, gamma-carboxylation, for instance of glutamic acid residues, hydroxylation and ADP-ribosylation. Other potential modifications include acetylation, acylation, amidation, covalent attachment of flavin, covalent attachment of a haeme moiety, covalent attachment of a nucleotide or nucleotide derivative, covalent attachment of a lipid derivative, covalent attachment of phosphatidylinositol, cross-linking, cyclization, disulphide bond formation, demethylation, formation of covalent cross-links, formation of cysteine, formation of pyroglutamate, formylation, GPI anchor formation, iodination, methylation, myristoylation, oxidation, proteolytic processing, phosphorylation, prenylation, racemization, selenoylation, transfer-RNA mediated addition of amino acids to proteins such as arginylation, and ubiquitination.

Modifications can occur anywhere in a polypeptide, including the peptide backbone, the amino acid side-chains and the amino or carboxyl termini. In fact, blockage of the amino or carboxyl terminus in a polypeptide, or both, by a covalent modification is common in naturally-occurring and synthetic polypeptides and such modifications may be present in polypeptides of the present invention.

The modifications that occur in a polypeptide often will be a function of how the polypeptide is made. For polypeptides that are made recombinantly, the nature and extent of the modifications in large part will be determined by the post-translational modification capacity of the particular host cell and the modification signals that are present in the amino acid sequence of the polypeptide in question. For instance, glycosylation patterns vary between different types of host cell.

The polypeptides of the present invention can be prepared in any suitable manner. Such polypeptides include, where the polypeptide is a naturally occurring polypeptide, isolated naturally-occurring polypeptides (for example purified from cell culture) and also recombinantly-produced polypeptides (including fusion proteins), synthetically-produced polypeptides or polypeptides that are produced by a combination of these methods. The term "isolated" does not denote the method by which the polypeptide is obtained or the level of purity of the preparation. Thus, such isolated species may be produced recombinantly, isolated directly from the cell or tissue of interest or produced synthetically based on the determined sequences.

The functionally-equivalent polypeptides of the first aspect of the invention may be polypeptides that are homologous to the INSP005 polypeptides. Two polypeptides are said to be "homologous", as the term is used herein, if the sequence of one of the polypeptides has a high enough degree of identity or similarity to the sequence of the other polypeptide. “Identity” indicates that at any particular position in the aligned sequences, the amino acid residue is identical between the sequences. “Similarity” indicates that, at any particular position in the aligned sequences, the amino acid residue is of a similar type between the sequences. Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Homologous polypeptides therefore include natural biological variants (for example, allelic variants or geographical variations within the species from which the polypeptides are derived) and mutants (such as mutants containing amino acid substitutions, insertions or deletions) of the INSP005 polypeptides. Such mutants may include polypeptides in which one or more of the amino acid residues are substituted with a conserved or non-conserved amino acid residue (preferably a conserved amino acid residue) and such substituted amino acid residue may or may not be one encoded by the genetic code. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr. Particularly preferred are variants in which several, i.e. between 5 and 10, 1 and 5, 1 and 3, 1 and 2 or just 1 amino acids are substituted, deleted or added in any combination. Especially preferred are silent substitutions, additions and deletions, which do not alter the properties and activities of the protein. Also especially preferred in this regard are conservative substitutions.

Such mutants also include polypeptides in which one or more of the amino acid residues includes a substituent group;

Typically, greater than 30% identity between two polypeptides is considered to be an indication of functional equivalence. Preferably, functionally equivalent polypeptides of the first aspect of the invention have a degree of sequence identity with the INSP005 polypeptides, or with active fragments thereof, of greater than 80%. More preferred polypeptides have degrees of identity of greater than 85%, 90%, 95%, 98%, 99% or more, respectively.

The functionally-equivalent polypeptides of the first aspect of the invention may also be polypeptides which have been identified using one or more techniques of structural alignment. For example, the Inpharmatica Genome Threader technology that forms one aspect of the search tools used to generate the Biopendium search database may be used (see PCT patent application WO 01/69507) to identify polypeptides of presently-unknown function which, while having low sequence identity as compared to the INSP005 polypeptides, are predicted to have secreted molecule activity, by virtue of sharing significant structural homology with the INSP005 polypeptide sequences. By “significant structural homology” is meant that the Inpharmatica Genome Threader predicts two proteins to share structural homology with a certainty of 10% and above.

The polypeptides of the first aspect of the invention also include fragments of the INSP005 polypeptides and fragments of the functional equivalents of the INSP005 polypeptides, provided that those fragments retain metalloprotease activity or have an antigenic determinant in common with the INSP005 polypeptides.

As used herein, the term “fragment” refers to a polypeptide having an amino acid sequence that is the same as part, but not all, of the amino acid sequence of the INSP005 polypeptides or one of its functional equivalents. The fragments should comprise at least n consecutive amino acids from the sequence and, depending on the particular sequence, n preferably is 7 or more (for example, 8, 10, 12, 14, 16, 18, 20 or more). Small fragments may form an antigenic determinant.

Such fragments may be “free-standing”, i.e. not part of or fused to other amino acids or polypeptides, or they may be comprised within a larger polypeptide of which they form a part or region. When comprised within a larger polypeptide, the fragment of the invention most preferably forms a single continuous region. For instance, certain preferred embodiments relate to a fragment having a pre- and/or pro-polypeptide region fused to the amino terminus of the fragment and/or an additional region fused to the carboxyl terminus of the fragment. However, several fragments may be comprised within a single larger polypeptide.

The polypeptides of the present invention or their immunogenic fragments (comprising at least one antigenic determinant) can be used to generate ligands, such as polyclonal or monoclonal antibodies, that are immunospecific for the polypeptides. Such antibodies may be employed to isolate or to identify clones expressing the polypeptides of the invention or to purify the polypeptides by affinity chromatography. The antibodies may also be employed as diagnostic or therapeutic aids, amongst other applications, as will be apparent to the skilled reader.

The term “immunospecific” means that the antibodies have substantially greater affinity for the polypeptides of the invention than their affinity for other related polypeptides in the prior art. As used herein, the term “antibody” refers to intact molecules as well as to fragments thereof, such as Fab, F(ab')2 and Fv, which are capable of binding to the antigenic determinant in question. Such antibodies thus bind to the polypeptides of the first aspect of the invention.

By “substantially greater affinity” we mean that there is a measurable increase in the affinity for a polypeptide of the invention as compared with the affinity for known secreted proteins.

Preferably, the affinity is at least 1.5-fold, 2-fold, 5-fold 10-fold, 100-fold, $10^3$-fold, $10^4$-fold, $10^5$-fold or $10^6$-fold greater for a polypeptide of the invention than for known secreted proteins.

If polyclonal antibodies are desired, a selected mammal, such as a mouse, rabbit, goat or horse, may be immunised with a polypeptide of the first aspect of the invention. The polypeptide used to immunise the animal can be derived by recombinant DNA technology or can be synthesized chemically. If desired, the polypeptide can be conjugated to a carrier protein. Commonly used carriers to which the polypeptides may be chemically coupled include bovine serum albumin, thyroglobulin and keyhole limpet haemocyanin. The coupled polypeptide is then used to immunise the animal. Serum from the immunised animal is collected and treated according to known procedures, for example by immunoaffinity chromatography.

Monoclonal antibodies to the polypeptides of the first aspect of the invention can also be readily produced by one skilled in the art. The general methodology for making monoclonal antibodies using hybridoma technology is well known (see, for example, Kohler, G. and Milstein, C., Nature 256: 495-497 (1975); Kozbor et al., Immunology Today 4: 72

(1983); Cole et al., 77-96 in Monoclonal Antibodies and Cancer Therapy, Alan R. Liss, Inc. (1985).

Panels of monoclonal antibodies produced against the polypeptides of the first aspect of the invention can be screened for various properties, i.e., for isotype, epitope, affinity, etc. Monoclonal antibodies are particularly useful in purification of the individual polypeptides against which they are directed. Alternatively, genes encoding the monoclonal antibodies of interest may be isolated from hybridomas, for instance by PCR techniques known in the art, and cloned and expressed in appropriate vectors.

Chimeric antibodies, in which non-human variable regions are joined or fused to human constant regions (see, for example, Liu et al., Proc. Natl. Acad. Sci. USA, 84, 3439 (1987)), may also be of use.

The antibody may be modified to make it less immunogenic in an individual, for example by humanisation (see Jones et al., Nature, 321, 522 (1986); Verhoeyen et al., Science, 239, 1534 (1988); Kabat et al., J. Immunol., 147, 1709 (1991); Queen et al., Proc. Natl Acad. Sci. USA, 86, 10029 (1989); Gorman et al., Proc. Natl Acad. Sci. USA, 88, 34181 (1991); and Hodgson et al., Bio/Technology, 9, 421 (1991)). The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody.

In a further alternative, the antibody may be a "bispecific" antibody, that is an antibody having two different antigen binding domains, each domain being directed against a different epitope.

Phage display technology may be utilised to select genes which encode antibodies with binding activities towards the polypeptides of the invention either from repertoires of PCR amplified V-genes of lymphocytes from humans screened for possessing the relevant antibodies, or from naive libraries (McCafferty, J. et al., (1990), Nature 348, 552-554; Marks, J. et al., (1992) Biotechnology 10, 779-783). The affinity of these antibodies can also be improved by chain shuffling (Clackson, T. et al., (1991) Nature 352, 624-628).

Antibodies generated by the above techniques, whether polyclonal or monoclonal, have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme.

Preferred nucleic acid molecules of the second and third aspects of the invention are those which encode the polypeptide sequences recited in SEQ ID NO:14, SEQ ID NO:34, or SEQ ID NO:36 and functionally equivalent polypeptides. These nucleic acid molecules may be used in the methods and applications described herein. The nucleic acid molecules of the invention preferably comprise at least n consecutive nucleotides from the sequences disclosed herein where, depending on the particular sequence, n is 10 or more (for example, 12, 14, 15, 18, 20, 25, 30, 35, 40 or more).

The nucleic acid molecules of the invention also include sequences that are complementary to nucleic acid molecules described above (for example, for antisense or probing purposes).

Nucleic acid molecules of the present invention may be in the form of RNA, such as mRNA, or in the form of DNA, including, for instance cDNA, synthetic DNA or genomic DNA. Such nucleic acid molecules may be obtained by cloning, by chemical synthetic techniques or by a combination thereof. The nucleic acid molecules can be prepared, for example, by chemical synthesis using techniques such as solid phase phosphoramidite chemical synthesis, from genomic or cDNA libraries or by separation from an organism. RNA molecules may generally be generated by the in vitro or in vivo transcription of DNA sequences.

The nucleic acid molecules may be double-stranded or single-stranded. Single-stranded DNA may be the coding strand, also known as the sense strand, or it may be the non-coding strand, also referred to as the anti-sense strand.

The term "nucleic acid molecule" also includes analogues of DNA and RNA, such as those containing modified backbones, and peptide nucleic acids (PNA). The term "PNA", as used herein, refers to an antisense molecule or an anti-gene agent which comprises an oligonucleotide of at least five nucleotides in length linked to a peptide backbone of amino acid residues, which preferably ends in lysine. The terminal lysine confers solubility to the composition. PNAs may be pegylated to extend their lifespan in a cell, where they preferentially bind complementary single stranded DNA and RNA and stop transcript elongation (Nielsen, P. E. et al. (1993) Anticancer Drug Des. 8:53-63).

A nucleic acid molecule which encodes the polypeptide of SEQ ID NO:14 may be identical to the coding sequence of the nucleic acid molecule shown in SEQ ID NO:13. A nucleic acid molecule which encodes the polypeptide of SEQ ID NO:34 may be identical to the coding sequence of the nucleic acid molecule shown in SEQ ID NO:33. A nucleic acid molecule which encodes the polypeptide of SEQ ID NO:36 may be identical to the coding sequence of the nucleic acid molecule shown in SEQ ID NO:35.

These molecules also may have a different sequence which, as a result of the degeneracy of the genetic code, encodes a polypeptide of SEQ ID NO:14, SEQ ID NO:34 or SEQ ID NO:36. Such nucleic acid molecules may include, but are not limited to, the coding sequence for the mature polypeptide by itself; the coding sequence for the mature polypeptide and additional coding sequences, such as those encoding a leader or secretory sequence, such as a pro-, pre- or prepro-polypeptide sequence; the coding sequence of the mature polypeptide, with or without the aforementioned additional coding sequences, together with further additional, non-coding sequences, including non-coding 5' and 3' sequences, such as the transcribed, non-translated sequences that play a role in transcription (including termination signals), ribosome binding and mRNA stability. The nucleic acid molecules may also include additional sequences which encode additional amino acids, such as those which provide additional functionalities.

The nucleic acid molecules of the second and third aspects of the invention may also encode the fragments or the functional equivalents of the polypeptides and fragments of the first aspect of the invention. Such a nucleic acid molecule may be a naturally-occurring variant such as a naturally-occurring allelic variant, or the molecule may be a variant that is not known to occur naturally. Such non-naturally occurring variants of the nucleic acid molecule may be made by mutagenesis techniques, including those applied to nucleic acid molecules, cells or organisms.

Among variants in this regard are variants that differ from the aforementioned nucleic acid molecules by nucleotide substitutions, deletions or insertions. The substitutions, deletions or insertions may involve one or more nucleotides. The variants may be altered in coding or non-coding regions or both. Alterations in the coding regions may produce conservative or non-conservative amino acid substitutions, deletions or insertions.

The nucleic acid molecules of the invention can also be engineered, using methods generally known in the art, for a variety of reasons, including modifying the cloning, processing, and/or expression of the gene product (the polypeptide). DNA shuffling by random fragmentation and PCR re-assembly of gene fragments and synthetic oligonucleotides are included as techniques which may be used to engineer the nucleotide sequences. Site-directed mutagenesis may be used to insert new restriction sites, alter glycosylation patterns, change codon preference, produce splice variants, introduce mutations and so forth.

Nucleic acid molecules which encode a polypeptide of the first aspect of the invention may be ligated to a heterologous sequence so that the combined nucleic acid molecule encodes a fusion protein. Such combined nucleic acid molecules are included within the second or third aspects of the invention. For example, to screen peptide libraries for inhibitors of the activity of the polypeptide, it may be useful to express, using such a combined nucleic acid molecule, a fusion protein that can be recognised by a commercially-available antibody. A fusion protein may also be engineered to contain a cleavage site located between the sequence of the polypeptide of the invention and the sequence of a heterologous protein so that the polypeptide may be cleaved and purified away from the heterologous protein.

The nucleic acid molecules of the invention also include antisense molecules that are partially complementary to nucleic acid molecules encoding polypeptides of the present invention and that therefore hybridize to the encoding nucleic acid molecules (hybridization). Such antisense molecules, such as oligonucleotides, can be designed to recognise, specifically bind to and prevent transcription of a target nucleic acid encoding a polypeptide of the invention, as will be known by those of ordinary skill in the art (see, for example, Cohen, J. S., Trends in Pharm. Sci., 10, 435 (1989), Okano, J. Neurochem. 56, 560 (1991); O'Connor, J. Neurochem 56, 560 (1991); Lee et al., Nucleic Acids Res 6, 3073 (1979); Cooney et al., Science 241, 456 (1988); Dervan et al., Science 251, 1360 (1991).

The term "hybridization" as used here refers to the association of two nucleic acid molecules with one another by hydrogen bonding. Typically, one molecule will be fixed to a solid support and the other will be free in solution. Then, the two molecules may be placed in contact with one another under conditions that favour hydrogen bonding. Factors that affect this bonding include: the type and volume of solvent; reaction temperature; time of hybridization; agitation; agents to block the non-specific attachment of the liquid phase molecule to the solid support (Denhardt's reagent or BLOTTO); the concentration of the molecules; use of compounds to increase the rate of association of molecules (dextran sulphate or polyethylene glycol); and the stringency of the washing conditions following hybridization (see Sambrook et al. [supra]).

The inhibition of hybridization of a completely complementary molecule to a target molecule may be examined using a hybridization assay, as known in the art (see, for example, Sambrook et al [supra]). A substantially homologous molecule will then compete for and inhibit the binding of a completely homologous molecule to the target molecule under various conditions of stringency, as taught in Wahl, G. M. and S. L. Berger (1987; Methods Enzymol. 152:399-407) and Kimmel, A. R. (1987; Methods Enzymol. 152:507-511).

"Stringency" refers to conditions in a hybridization reaction that favour the association of very similar molecules over association of molecules that differ. High stringency hybridisation conditions are defined as overnight incubation at 42° C in a solution comprising 50% formamide, 5×SSC (150 mM NaCl, 15 mM trisodium citrate), 50 mM sodium phosphate (pH 7.6), 5× Denhardts solution, 10% dextran sulphate, and 20 microgram/ml denatured, sheared salmon sperm DNA, followed by washing the filters in 0.1×SSC at approximately 65° C. Low stringency conditions involve the hybridisation reaction being carried out at 35° C (see Sambrook et al. [supra]). Preferably, the conditions used for hybridization are those of high stringency.

Preferred embodiments of this aspect of the invention are nucleic acid molecules that are at least 70% identical over their entire length to nucleic acid molecules encoding the INSP005 polypeptides (SEQ ID NO:13, SEQ ID NO:33 and SEQ ID NO:35), and nucleic acid molecules that are substantially complementary to such nucleic acid molecules. Preferably, a nucleic acid molecule according to this aspect of the invention comprises a region that is at least 80% identical over its entire length to the nucleic acid molecule having the sequence given in SEQ ID NO:13, SEQ ID NO:33 or SEQ ID NO:35 or a nucleic acid molecule that is complementary thereto. In this regard, nucleic acid molecules at least 90%, preferably at least 95%, more preferably at least 98% or 99% identical over their entire length to the same are particularly preferred. Preferred embodiments in this respect are nucleic acid molecules that encode polypeptides which retain substantially the same biological function or activity as the INSP005 polypeptides.

The invention also provides a process for detecting a nucleic acid molecule of the invention, comprising the steps of: (a) contacting a nucleic probe according to the invention with a biological sample under hybridizing conditions to form duplexes; and (b) detecting any such duplexes that are formed.

As discussed additionally below in connection with assays that may be utilised according to the invention, a nucleic acid molecule as described above may be used as a hybridization probe for RNA, cDNA or genomic DNA, in order to isolate full-length cDNAs and genomic clones encoding the INSP005 polypeptides and to isolate cDNA and genomic clones of homologous or orthologous genes that have a high sequence similarity to the gene encoding these polypeptides.

In this regard, the following techniques, among others known in the art, may be utilised and are discussed below for purposes of illustration. Methods for DNA sequencing and analysis are well known and are generally available in the art and may, indeed, be used to practice many of the embodiments of the invention discussed herein. Such methods may employ such enzymes as the Klenow fragment of DNA polymerase 1, Sequenase (US Biochemical Corp, Cleveland, Ohio), Taq polymerase (Perkin Elmer), thermostable T7 polymerase (Amersham, Chicago, Ill.), or combinations of polymerases and proof-reading exonucleases such as those found in the ELONGASE Amplification System marketed by Gibco/BRL (Gaithersburg, Md.). Preferably, the sequencing process may be automated using machines such as the Hamilton Micro Lab 2200 (Hamilton, Reno, Nev.), the Peltier Thermal Cycler (PTC200; MJ Research, Watertown, Mass.) and the ABI Catalyst and 373 and 377 DNA Sequencers (Perkin Elmer).

One method for isolating a nucleic acid molecule encoding a polypeptide with an equivalent function to that of the INSP005 polypeptides is to probe a genomic or cDNA library with a natural or artificially-designed probe using standard procedures that are recognised in the art (see, for example, "Current Protocols in Molecular Biology", Ausubel et al. (eds). Greene Publishing Association and John Wiley Interscience, New York, 1989, 1992). Probes comprising at least 15, preferably at least 30, and more preferably at least 50, contiguous bases that correspond to, or are complementary to, nucleic acid sequences from the appropriate encoding gene (SEQ ID NO:13, SEQ ID NO:33 or SEQ ID NO:35), are particularly useful probes. Such probes may be labelled with an analytically-detectable reagent to facilitate their identification. Useful reagents include, but are not limited to, radioisotopes, fluorescent dyes and enzymes that are capable of catalysing the formation of a detectable product. Using these probes, the ordinarily skilled artisan will be capable of isolating complementary copies of genomic DNA, cDNA or RNA polynucleotides encoding proteins of interest from human, mammalian or other animal sources and screening such sources for related sequences, for example, for additional members of the family, type and/or subtype.

In many cases, isolated cDNA sequences will be incomplete, in that the region encoding the polypeptide will be cut short, normally at the 5' end. Several methods are available to obtain full length cDNAs, or to extend short cDNAs. Such sequences may be extended utilising a partial nucleotide sequence and employing various methods known in the art to detect upstream sequences such as promoters and regulatory elements. For example, one method which may be employed is based on the method of Rapid Amplification of cDNA Ends (RACE; see, for example, Frohman et al., PNAS USA 85, 8998-9002, 1988). Recent modifications of this technique, exemplified by the Marathon™ technology (Clontech Laboratories Inc.), for example, have significantly simplified the search for longer cDNAs. A slightly different technique, termed "restriction-site" PCR, uses universal primers to retrieve unknown nucleic acid sequence adjacent a known locus (Sarkar, G. (1993) PCR Methods Applic. 2:318-322). Inverse PCR may also be used to amplify or to extend sequences using divergent primers based on a known region (Triglia, T. et al. (1988) Nucleic Acids Res. 16:8186). Another method which may be used is capture PCR which involves PCR amplification of DNA fragments adjacent a known sequence in human and yeast artificial chromosome DNA (Lagerstrom, M. et al. (1991) PCR Methods Applic., 1, 111-119). Another method which may be used to retrieve unknown sequences is that of Parker, J. D. et al. (1991); Nucleic Acids Res. 19:3055-3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

In one embodiment of the invention, the nucleic acid molecules of the present invention may be used for chromosome localisation. In this technique, a nucleic acid molecule is specifically targeted to, and can hybridize with, a particular location on an individual human chromosome. The mapping of relevant sequences to chromosomes according to the present invention is an important step in the confirmatory correlation of those sequences with the gene-associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationships between genes and diseases that have been mapped to the same chromosomal region are then identified through linkage analysis (coinheritance of physically adjacent genes). This provides valuable information to investigators searching for disease genes using positional cloning or other gene discovery techniques. Once the disease or syndrome has been crudely localised by genetic linkage to a particular genomic region, any sequences mapping to that area may represent associated or regulatory genes for further investigation. The nucleic acid molecule may also be used to detect differences in the chromosomal location due to translocation, inversion, etc. among normal, carrier, or affected individuals.

The nucleic acid molecules of the present invention are also valuable for tissue localisation. Such techniques allow the determination of expression patterns of the polypeptide in tissues by detection of the mRNAs that encode them. These techniques include in situ hybridization techniques and nucleotide amplification techniques, such as PCR. Results from these studies provide an indication of the normal functions of the polypeptide in the organism. In addition, comparative studies of the normal expression pattern of mRNAs with that of mRNAs encoded by a mutant gene provide valuable insights into the role of mutant polypeptides in disease. Such inappropriate expression may be of a temporal, spatial or quantitative nature.

Gene silencing approaches may also be undertaken to down-regulate endogenous expression of a gene encoding a polypeptide of the invention. RNA interference (RNAi) (Elbashir, S M et al., Nature 2001, 411, 494-498) is one method of sequence specific post-transcriptional gene silencing that may be employed. Short dsRNA oligonucleotides are synthesised in vitro and introduced into a cell. The sequence specific binding of these dsRNA oligonucleotides triggers the degradation of target mRNA, reducing or ablating target protein expression.

Efficacy of the gene silencing approaches assessed above may be assessed through the measurement of polypeptide expression (for example, by Western blotting), and at the RNA level using TaqMan-based methodologies.

The vectors of the present invention comprise nucleic acid molecules of the invention and may be cloning or expression vectors. The host cells of the invention, which may be transformed, transfected or transduced with the vectors of the invention may be prokaryotic or eukaryotic.

The polypeptides of the invention may be prepared in recombinant form by expression of their encoding nucleic acid molecules in vectors contained within a host cell. Such expression methods are well known to those of skill in the art and many are described in detail by Sambrook et al (supra) and Fernandez & Hoeffler (1998, eds. "Gene expression systems. Using nature for the art of expression". Academic Press, San Diego, London, Boston, New York, Sydney, Tokyo, Toronto).

Generally, any system or vector that is suitable to maintain, propagate or express nucleic acid molecules to produce a polypeptide in the required host may be used. The appropriate nucleotide sequence may be inserted into an expression system by any of a variety of well-known and routine techniques, such as, for example, those described in Sambrook et al., (supra). Generally, the encoding gene can be placed under the control of a control element such as a promoter, ribosome binding site (for bacterial expression) and, optionally, an operator, so that the DNA sequence encoding the desired polypeptide is transcribed into RNA in the transformed host cell.

Examples of suitable expression systems include, for example, chromosomal, episomal and virus-derived systems, including, for example, vectors derived from: bacterial plasmids, bacteriophage, transposons, yeast episomes, insertion elements, yeast chromosomal elements, viruses such as baculoviruses, papova viruses such as SV40, vaccinia viruses, adenoviruses, fowl pox viruses, pseudorabies viruses and retroviruses, or combinations thereof, such as those derived from plasmid and bacteriophage genetic elements, including cosmids and phagemids. Human artificial chromosomes (HACs) may also be employed to deliver larger fragments of DNA than can be contained and expressed in a plasmid.

Particularly suitable expression systems include microorganisms such as bacteria transformed with recombinant bacteriophage, plasmid or cosmid DNA expression vectors; yeast transformed with yeast expression vectors; insect cell systems infected with virus expression vectors (for example, baculovirus); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems. Cell-free translation systems can also be employed to produce the polypeptides of the invention.

Introduction of nucleic acid molecules encoding a polypeptide of the present invention into host cells can be effected by methods described in many standard laboratory manuals, such as Davis et al., Basic Methods in Molecular Biology (1986) and Sambrook et al., (supra). Particularly suitable methods include calcium phosphate transfection, DEAE-dextran mediated transfection, transvection, microinjection, cationic lipid-mediated transfection, electroporation, transduction, scrape loading, ballistic introduction or infection (see Sambrook et al., 1989 [supra]; Ausubel et al., 1991 [supra]; Spector, Goldman & Leinwald, 1998). In eukaryotic cells, expression systems may either be transient (for example, episomal) or permanent (chromosomal integration) according to the needs of the system.

The encoding nucleic acid molecule may or may not include a sequence encoding a control sequence, such as a signal peptide or leader sequence, as desired, for example, for secretion of the translated polypeptide into the lumen of the endoplasmic reticulum, into the periplasmic space or into the extracellular environment. These signals may be endogenous to the polypeptide or they may be heterologous signals. Leader sequences can be removed by the bacterial host in post-translational processing.

In addition to control sequences, it may be desirable to add regulatory sequences that allow for regulation of the expression of the polypeptide relative to the growth of the host cell. Examples of regulatory sequences are those which cause the expression of a gene to be increased or decreased in response to a chemical or physical stimulus, including the presence of a regulatory compound or to various temperature or metabolic conditions. Regulatory sequences are those non-translated regions of the vector, such as enhancers, promoters and 5' and 3' untranslated regions. These interact with host cellular proteins to carry out transcription and translation. Such regulatory sequences may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the Bluescript phagemid (Stratagene, La Jolla, Calif.) or pSport1™ plasmid (Gibco BRL) and the like may be used. The baculovirus polyhedrin promoter may be used in insect cells. Promoters or enhancers derived from the genomes of plant cells (for example, heat shock, RUBISCO and storage protein genes) or from plant viruses (for example, viral promoters or leader sequences) may be cloned into the vector. In mammalian cell systems, promoters from mammalian genes or from mammalian viruses are preferable. If it is necessary to generate a cell line that contains multiple copies of the sequence, vectors based on SV40 or EBV may be used with an appropriate selectable marker.

An expression vector is constructed so that the particular nucleic acid coding sequence is located in the vector with the appropriate regulatory sequences, the positioning and orientation of the coding sequence with respect to the regulatory sequences being such that the coding sequence is transcribed under the "control" of the regulatory sequences, i.e., RNA polymerase which binds to the DNA molecule at the control sequences transcribes the coding sequence. In some cases it may be necessary to modify the sequence so that it may be attached to the control sequences with the appropriate orientation; i.e., to maintain the reading frame.

The control sequences and other regulatory sequences may be ligated to the nucleic acid coding sequence prior to insertion into a vector. Alternatively, the coding sequence can be cloned directly into an expression vector that already contains the control sequences and an appropriate restriction site.

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines.

In the baculovirus system, the materials for baculovirus/insect cell expression systems are commercially available in kit form from, inter alia, Invitrogen, San Diego Calif. (the "MaxBac" kit). These techniques are generally known to those skilled in the art and are described fully in Summers and Smith, Texas Agricultural Experiment Station Bulletin No. 1555 (1987). Particularly suitable host cells for use in this system include insect cells such as *Drosophila* S2 and *Spodoptera* Sf9 cells.

There are many plant cell culture and whole plant genetic expression systems known in the art. Examples of suitable plant cellular genetic expression systems include those described in U.S. Pat. Nos. 5,693,506; 5,659,122; and 5,608,143. Additional examples of genetic expression in plant cell culture has been described by Zenk, Phytochemistry 30, 3861-3863 (1991).

In particular, all plants from which protoplasts can be isolated and cultured to give whole regenerated plants can be utilised, so that whole plants are recovered which contain the transferred gene. Practically all plants can be regenerated from cultured cells or tissues, including but not limited to all major species of sugar cane, sugar beet, cotton, fruit and other trees, legumes and vegetables.

Examples of particularly preferred bacterial host cells include *streptococci, staphylococci, E. coli, Streptomyces* and *Bacillus subtilis* cells.

Examples of particularly suitable host cells for fungal expression include yeast cells (for example, *S. cerevisiae*) and *Aspergillus* cells.

Any number of selection systems are known in the art that may be used to recover transformed cell lines. Examples include the herpes simplex virus thymidine kinase (Wigler, M. et al. (1977) Cell 11:223-32) and adenine phosphoribosyltransferase (Lowy, I. et al. (1980) Cell 22:817-23) genes that can be employed in tk− or aprt± cells, respectively.

Also, antimetabolite, antibiotic or herbicide resistance can be used as the basis for selection; for example, dihydrofolate reductase (DHFR) that confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al (1981) J. Mol. Biol. 150:1-14) and als or pat, which confer resistance to chlorsulfuron and phosphinotricin acetyltransferase, respectively. Additional selectable genes have been described, examples of which will be clear to those of skill in the art.

Although the presence or absence of marker gene expression suggests that the gene of interest is also present, its presence and expression may need to be confirmed. For example, if the relevant sequence is inserted within a marker gene sequence, transformed cells containing the appropriate sequences can be identified by the absence of marker gene function. Alternatively, a marker gene can be placed in tandem with a sequence encoding a polypeptide of the invention under the control of a single promoter. Expression of the marker gene in response to induction or selection usually indicates expression of the tandem gene as well.

Alternatively, host cells that contain a nucleic acid sequence encoding a polypeptide of the invention and which express said polypeptide may be identified by a variety of procedures known to those of skill in the art. These procedures include, but are not limited to, DNA-DNA or DNA-RNA hybridizations and protein bioassays, for example, fluorescence activated cell sorting (FACS) or immunoassay techniques (such as the enzyme-linked immunosorbent assay [ELISA] and radioimmunoassay [RIA]), that include membrane, solution, or chip based technologies for the detection and/or quantification of nucleic acid or protein (see Hampton, R. et al. (1990) Serological Methods, a Laboratory Manual, APS Press, St Paul, Minn.) and Maddox, D. E. et al. (1983) J. Exp. Med, 158, 1211-1216).

A wide variety of labels and conjugation techniques are known by those skilled in the art and may be used in various nucleic acid and amino acid assays. Means for producing labelled hybridization or PCR probes for detecting sequences related to nucleic acid molecules encoding polypeptides of the present invention include oligolabelling, nick translation, end-labelling or PCR amplification using a labelled polynucleotide. Alternatively, the sequences encoding the polypeptide of the invention may be cloned into a vector for the production of an mRNA probe. Such vectors are known in the art, are commercially available, and may be used to synthesise RNA probes in vitro by addition of an appropriate RNA polymerase such as T7, T3 or SP6 and labelled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)).

Suitable reporter molecules or labels, which may be used for ease of detection, include radionuclides, enzymes and fluorescent, chemiluminescent or chromogenic agents as well as substrates, cofactors, inhibitors, magnetic particles, and the like.

Nucleic acid molecules according to the present invention may also be used to create transgenic animals, particularly rodent animals. Such transgenic animals form a further aspect of the present invention. This may be done locally by modification of somatic cells, or by germ line therapy to incorporate heritable modifications. Such transgenic animals may be particularly useful in the generation of animal models for drug molecules effective as modulators of the polypeptides of the present invention.

The polypeptide can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography is particularly useful for purification. Well known techniques for refolding proteins may be employed to regenerate an active conformation when the polypeptide is denatured during isolation and or purification.

Specialised vector constructions may also be used to facilitate purification of proteins, as desired, by joining sequences encoding the polypeptides of the invention to a nucleotide sequence encoding a polypeptide domain that will facilitate purification of soluble proteins. Examples of such purification-facilitating domains include metal chelating peptides such as histidine-tryptophan modules that allow purification on immobilised metals, protein A domains that allow purification on immobilised immunoglobulin, and the domain utilised in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the polypeptide of the invention may be used to facilitate purification. One such expression vector provides for expression of a fusion protein containing the polypeptide of the invention fused to several histidine residues preceding a thioredoxin or an enterokinase cleavage site. The histidine residues facilitate purification by IMAC (immobilised metal ion affinity chromatography as described in Porath, J. et al. (1992), Prot. Exp. Purif. 3: 263-281) while the thioredoxin or enterokinase cleavage site provides a means for purifying the polypeptide from the fusion protein. A discussion of vectors which contain fusion proteins is provided in Kroll, D. J. et al. (1993; DNA Cell Biol. 12:441-453).

If the polypeptide is to be expressed for use in screening assays, generally it is preferred that it be produced at the surface of the host cell in which it is expressed. In this event, the host cells may be harvested prior to use in the screening assay, for example using techniques such as fluorescence activated cell sorting (FACS) or immunoaffinity techniques. If the polypeptide is secreted into the medium, the medium can be recovered in order to recover and purify the expressed polypeptide. If polypeptide is produced intracellularly, the cells must first be lysed before the polypeptide is recovered.

The polypeptide of the invention can be used to screen libraries of compounds in any of a variety of drug screening techniques. Such compounds may activate (agonise) or inhibit (antagonise) the level of expression of the gene or the activity of the polypeptide of the invention and form a further aspect of the present invention. Preferred compounds are effective to alter the expression of a natural gene which encodes a polypeptide of the first aspect of the invention or to regulate the activity of a polypeptide of the first aspect of the invention.

Agonist or antagonist compounds may be isolated from, for example, cells, cell-free preparations, chemical libraries or natural product mixtures. These agonists or antagonists may be natural or modified substrates, ligands, enzymes, receptors or structural or functional mimetics. For a suitable review of such screening techniques, see Coligan et al., Current Protocols in Immunology 1(2): Chapter 5 (1991).

Compounds that are most likely to be good antagonists are molecules that bind to the polypeptide of the invention without inducing the biological effects of the polypeptide upon binding to it. Potential antagonists include small organic molecules, peptides, polypeptides and antibodies that bind to the polypeptide of the invention and thereby inhibit or extinguish its activity. In this fashion, binding of the polypeptide to normal cellular binding molecules may be inhibited, such that the normal biological activity of the polypeptide is prevented.

The polypeptide of the invention that is employed in such a screening technique may be free in solution, affixed to a solid support, borne on a cell surface or located intracellularly. In general, such screening procedures may involve using appropriate cells or cell membranes that express the polypeptide that are contacted with a test compound to observe binding, or stimulation or inhibition of a functional response. The functional response of the cells contacted with the test compound is then compared with control cells that were not contacted with the test compound. Such an assay may assess whether the test compound results in a signal generated by activation of the polypeptide, using an appropriate detection system. Inhibitors of activation are generally assayed in the presence of a known agonist and the effect on activation by the agonist in the presence of the test compound is observed.

The INSP005 polypeptides of the present invention may modulate a variety of physiological and pathological processes, including reproductive processes such as egg maturation or fertilisation. Thus, the biological activity of the INSP005 polypeptides can be examined in systems that allow the study of such modulatory activities, using a variety of suitable assays. For example, possible assays include the measurement of oocyte fertilisation and/or pregnancy rates after ovulation induction, the measurement of embryo implantation rates, or in the case of male infertility the measurement of sperm motility (Luo C. W. et al, J. Biol. Chem. 276 (10), 6913-6921 (2001)).

A preferred method for identifying an agonist or antagonist compound of a polypeptide of the present invention comprises:

(a) contacting a cell expressing on the surface thereof the polypeptide according to the first aspect of the invention, the polypeptide being associated with a second component capable of providing a detectable signal in response to the binding of a compound to the polypeptide, with a compound to be screened under conditions to permit binding to the polypeptide; and
(b) determining whether the compound binds to and activates or inhibits the polypeptide by measuring the level of a signal generated from the interaction of the compound with the polypeptide.

A further preferred method for identifying an agonist or antagonist of a polypeptide of the invention comprises:

(a) contacting a cell expressing on the surface thereof the polypeptide, the polypeptide being associated with a second component capable of providing a detectable signal in response to the binding of a compound to the polypeptide, with a compound to be screened under conditions to permit binding to the polypeptide; and
(b) determining whether the compound binds to and activates or inhibits the polypeptide by comparing the level of a signal generated from the interaction of the compound with the polypeptide with the level of a signal in the absence of the compound.

In further preferred embodiments, the general methods that are described above may further comprise conducting the identification of agonist or antagonist in the presence of labelled or unlabelled ligand for the polypeptide.

In another embodiment of the method for identifying agonist or antagonist of a polypeptide of the present invention comprises:

determining the inhibition of binding of a ligand to cells which have a polypeptide of the invention on the surface thereof, or to cell membranes containing such a polypeptide, in the presence of a candidate compound under conditions to permit binding to the polypeptide, and determining the amount of ligand bound to the polypeptide. A compound capable of causing reduction of binding of a ligand is considered to be an agonist or antagonist. Preferably the ligand is labelled.

More particularly, a method of screening for a polypeptide antagonist or agonist compound comprises the steps of:

(a) incubating a labelled ligand with a whole cell expressing a polypeptide according to the invention on the cell surface, or a cell membrane containing a polypeptide of the invention,
(b) measuring the amount of labelled ligand bound to the whole cell or the cell membrane;
(c) adding a candidate compound to a mixture of labelled ligand and the whole cell or the cell membrane of step (a) and allowing the mixture to attain equilibrium;
(d) measuring the amount of labelled ligand bound to the whole cell or the cell membrane after step (c); and
(e) comparing the difference in the labelled ligand bound in step (b) and (d), such that the compound which causes the reduction in binding in step (d) is considered to be an agonist or antagonist.

The polypeptides may be found to modulate a variety of physiological and pathological processes in a dose-dependent manner in the above-described assays. Thus, the "functional equivalents" of the polypeptides of the invention include polypeptides that exhibit any of the same modulatory activities in the above-described assays in a dose-dependent manner. Although the degree of dose-dependent activity need not be identical to that of the polypeptides of the invention, preferably the "functional equivalents" will exhibit substantially similar dose-dependence in a given activity assay compared to the polypeptides of the invention.

In certain of the embodiments described above, simple binding assays may be used, in which the adherence of a test compound to a surface bearing the polypeptide is detected by means of a label directly or indirectly associated with the test compound or in an assay involving competition with a labelled competitor. In another embodiment, competitive drug screening assays may be used, in which neutralising antibodies that are capable of binding the polypeptide specifically compete with a test compound for binding. In this manner, the antibodies can be used to detect the presence of any test compound that possesses specific binding affinity for the polypeptide.

Assays may also be designed to detect the effect of added test compounds on the production of mRNA encoding the polypeptide in cells. For example, an ELISA may be constructed that measures secreted or cell-associated levels of polypeptide using monoclonal or polyclonal antibodies by standard methods known in the art, and this can be used to search for compounds that may inhibit or enhance the production of the polypeptide from suitably manipulated cells or tissues. The formation of binding complexes between the polypeptide and the compound being tested may then be measured.

Assay methods that are also included within the terms of the present invention are those that involve the use of the genes and polypeptides of the invention in overexpression or ablation assays. Such assays involve the manipulation of levels of these genes/polypeptides in cells and assessment of the impact of this manipulation event on the physiology of the manipulated cells. For example, such experiments reveal details of signaling and metabolic pathways in which the particular genes/polypeptides are implicated, generate information regarding the identities of polypeptides with which the studied polypeptides interact and provide clues as to methods by which related genes and proteins are regulated.

Another technique for drug screening which may be used provides for high throughput screening of compounds having suitable binding affinity to the polypeptide of interest (see International patent application WO84/03564). In this method, large numbers of different small test compounds are synthesised on a solid substrate, which may then be reacted with the polypeptide of the invention and washed. One way of immobilising the polypeptide is to use non-neutralising antibodies. Bound polypeptide may then be detected using methods that are well known in the art. Purified polypeptide can also be coated directly onto plates for use in the aforementioned drug screening techniques.

The polypeptide of the invention may be used to identify membrane-bound or soluble receptors, through standard receptor binding techniques that are known in the art, such as ligand binding and crosslinking assays in which the polypeptide is labelled with a radioactive isotope, is chemically modified, or is fused to a peptide sequence that facilitates its detection or purification, and incubated with a source of the putative receptor (for example, a composition of cells, cell membranes, cell supernatants, tissue extracts, or bodily fluids). The efficacy of binding may be measured using biophysical techniques such as surface plasmon resonance (supplied by Biacore AB, Uppsala, Sweden) and spectroscopy. Binding assays may be used for the purification and cloning of the receptor, but may also identify agonists and antagonists of the polypeptide, that compete with the binding of the polypeptide to its receptor. Standard methods for conducting screening assays are well understood in the art.

The invention also includes a screening kit useful in the methods for identifying agonists, antagonists, ligands, receptors, substrates, enzymes, that are described above.

The invention includes the agonists, antagonists, ligands, receptors, substrates and enzymes, and other compounds which modulate the activity or antigenicity of the polypeptide of the invention discovered by the methods that are described above.

The invention also provides pharmaceutical compositions comprising a polypeptide, nucleic acid, ligand or compound of the invention in combination with a suitable pharmaceutical carrier. These compositions may be suitable as therapeutic or diagnostic reagents, as vaccines, or as other immunogenic compositions, as outlined in detail below.

According to the terminology used herein, a composition containing a polypeptide, nucleic acid, ligand or compound [X] is "substantially free of" impurities [herein, Y] when at least 85% by weight of the total X+Y in the composition is X. Preferably, X comprises at least about 90% by weight of the total of X+Y in the composition, more preferably at least about 95%, 98% or even 99% by weight.

The pharmaceutical compositions should preferably comprise a therapeutically effective amount of the polypeptide, nucleic acid molecule, ligand, or compound of the invention. The term "therapeutically effective amount" as used herein refers to an amount of a therapeutic agent needed to treat, ameliorate, or prevent a targeted disease or condition, or to exhibit a detectable therapeutic or preventative effect. For any compound, the therapeutically effective dose can be estimated initially either in cell culture assays, for example, of neoplastic cells, or in animal models, usually mice, rabbits, dogs, or pigs. The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective dose will be from 0.01 mg/kg to 50 mg/kg, preferably 0.05 mg/kg to 10 mg/kg. Compositions may be administered individually to a patient or may be administered in combination with other agents, drugs or hormones.

A pharmaceutical composition may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity. Suitable carriers may be large, slowly metabolised macromolecules such as proteins, polysaccharides, polylactic acids, polyglycolic acids, polymeric amino acids, amino acid copolymers and inactive virus particles.

Pharmaceutically acceptable salts can be used therein, for example, mineral acid salts such as hydrochlorides, hydrobromides, phosphates, sulphates, and the like; and the salts of organic acids such as acetates, propionates, malonates, benzoates, and the like. A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The pharmaceutical compositions utilised in this invention may be administered by any number of routes including, but not limited to, oral, intravenous, intramuscular, intra-arterial, intramedullary, intrathecal, intraventricular, transdermal or transcutaneous applications (for example, see WO98/20734), subcutaneous, intraperitoneal, intranasal, enteral, topical, sublingual, intravaginal or rectal means. Gene guns or hyposprays may also be used to administer the pharmaceutical compositions of the invention. Typically, the therapeutic compositions may be prepared as injectables, either as liquid solutions or suspensions; solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

If the activity of the polypeptide of the invention is in excess in a particular disease state, several approaches are available. One approach comprises administering to a subject an inhibitor compound (antagonist) as described above, along with a pharmaceutically acceptable carrier in an amount effective to inhibit the function of the polypeptide, such as by blocking the binding of ligands, substrates, enzymes, receptors, or by inhibiting a second signal, and thereby alleviating the abnormal condition. Preferably, such antagonists are antibodies. Most preferably, such antibodies are chimeric and/or humanised to minimise their immunogenicity, as described previously.

In another approach, soluble forms of the polypeptide that retain binding affinity for the ligand, substrate, enzyme, receptor, in question, may be administered. Typically, the polypeptide may be administered in the form of fragments that retain the relevant portions.

In an alternative approach, expression of the gene encoding the polypeptide can be inhibited using expression blocking techniques, such as the use of antisense nucleic acid molecules (as described above), either internally generated or separately administered. Modifications of gene expression can be obtained by designing complementary sequences or antisense molecules (DNA, RNA, or PNA) to the control, 5' or regulatory regions (signal sequence, promoters, enhancers and introns) of the gene encoding the polypeptide. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, Molecular and Immunologic Approaches, Futura Publishing Co., Mt. Kisco, N.Y.). The complementary sequence or antisense molecule may also be designed to block translation of mRNA by preventing the transcript from binding to ribosomes. Such oligonucleotides may be administered or may be generated in situ from expression in vivo.

In addition, expression of the polypeptide of the invention may be prevented by using ribozymes specific to its encoding mRNA sequence. Ribozymes are catalytically active RNAs that can be natural or synthetic (see for example Usman, N, et al., Curr. Opin. Struct. Biol (1996) 6 (4), 527-33). Synthetic ribozymes can be designed to specifically cleave mRNAs at selected positions thereby preventing translation of the mRNAs into functional polypeptide. Ribozymes may be synthesised with a natural ribose phosphate backbone and natural bases, as normally found in RNA molecules. Alternatively the ribozymes may be synthesised with non-natural backbones, for example, 2'-O-methyl RNA, to provide protection from ribonuclease degradation and may contain modified bases.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of non-traditional bases such as inosine, queosine and butosine, as well as acetyl-, methyl-, thio- and similarly modified forms of adenine, cytidine, guanine, thymine and uridine which are not as easily recognised by endogenous endonucleases.

For treating abnormal conditions related to an under-expression of the polypeptide of the invention and its activity, several approaches are also available. One approach comprises administering to a subject a therapeutically effective amount of a compound that activates the polypeptide, i.e., an agonist as described above, to alleviate the abnormal condition. Alternatively, a therapeutic amount of the polypeptide in combination with a suitable pharmaceutical carrier may be administered to restore the relevant physiological balance of polypeptide.

Gene therapy may be employed to effect the endogenous production of the polypeptide by the relevant cells in the subject. Gene therapy is used to treat permanently the inappropriate production of the polypeptide by replacing a defective gene with a corrected therapeutic gene.

Gene therapy of the present invention can occur in vivo or ex vivo. Ex vivo gene therapy requires the isolation and purification of patient cells, the introduction of a therapeutic gene and introduction of the genetically altered cells back into the patient. In contrast, in vivo gene therapy does not require isolation and purification of a patient's cells.

The therapeutic gene is typically "packaged" for administration to a patient. Gene delivery vehicles may be non-viral, such as liposomes, or replication-deficient viruses, such as adenovirus as described by Berkner, K. L., in Curr. Top. Microbiol. Immunol., 158, 39-66 (1992) or adeno-associated virus (AAV) vectors as described by Muzyczka, N., in Curr. Top. Microbiol. Immunol., 158, 97-129 (1992) and U.S. Pat. No. 5,252,479. For example, a nucleic acid molecule encoding a polypeptide of the invention may be engineered for expression in a replication-defective retroviral vector. This expression construct may then be isolated and introduced into a packaging cell transduced with a retroviral plasmid vector containing RNA encoding the polypeptide, such that the packaging cell now produces infectious viral particles containing the gene of interest. These producer cells may be administered to a subject for engineering cells in vivo and expression of the polypeptide in vivo (see Chapter 20, Gene Therapy and other Molecular Genetic-based Therapeutic Approaches, (and references cited therein) in Human Molecular Genetics (1996), T Strachan and A P Read, BIOS Scientific Publishers Ltd).

Another approach is the administration of "naked DNA" in which the therapeutic gene is directly injected into the bloodstream or muscle tissue.

In situations in which the polypeptides or nucleic acid molecules of the invention are disease-causing agents, the invention provides that they can be used in vaccines to raise antibodies against the disease causing agent. Where the aforementioned polypeptide or nucleic acid molecule is one that is up-regulated, vaccine development can involve the raising of antibodies or T cells against such agents (as described in WO00/29428).

Vaccines according to the invention may either be prophylactic (ie. to prevent infection) or therapeutic (ie. to treat disease after infection). Such vaccines comprise immunising antigen(s), immunogen(s), polypeptide(s), protein(s) or nucleic acid, usually in combination with pharmaceutically-acceptable carriers as described above, which include any carrier that does not itself induce the production of antibodies harmful to the individual receiving the composition. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, and other pathogens.

Since polypeptides may be broken down in the stomach, vaccines comprising polypeptides are preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient, and aqueous and non-aqueous sterile suspensions which may include suspending agents or thickening agents.

The vaccine formulations of the invention may be presented in unit-dose or multi-dose containers. For example, sealed ampoules and vials and may be stored in a freeze-dried condition requiring only the addition of the sterile liquid carrier immediately prior to use. The dosage will depend on the specific activity of the vaccine and can be readily determined by routine experimentation.

Genetic delivery of antibodies that bind to polypeptides according to the invention may also be effected, for example, as described in International patent application WO98/55607.

The technology referred to as jet injection (see, for example, www.powderject.com) may also be useful in the formulation of vaccine compositions.

A number of suitable methods for vaccination and vaccine delivery systems are described in International patent application WO00/29428.

This invention also relates to the use of nucleic acid molecules according to the present invention as diagnostic reagents. Detection of a mutated form of the gene characterised by the nucleic acid molecules of the invention which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acid molecules for diagnosis may be obtained from a subject's cells, such as from blood, urine, saliva, tissue biopsy or autopsy material. The genomic DNA may be used directly for detection or may be amplified enzymatically by using PCR, ligase chain reaction (LCR), strand displacement amplification (SDA), or other amplification techniques (see Saiki et al., Nature, 324, 163-166 (1986); Bej, et al., Crit. Rev. Biochem. Molec. Biol., 26, 301-334 (1991); Birkenmeyer et al., J. Virol. Meth., 35, 117-126 (1991); Van Brunt, J., Bio/Technology, 8, 291-294 (1990)) prior to analysis.

In one embodiment, this aspect of the invention provides a method of diagnosing a disease in a patient, comprising assessing the level of expression of a natural gene encoding a polypeptide according to the invention and comparing said level of expression to a control level, wherein a level that is different to said control level is indicative of disease. The method may comprise the steps of:

a) contacting a sample of tissue from the patient with a nucleic acid probe under stringent conditions that allow the formation of a hybrid complex between a nucleic acid molecule of the invention and the probe;
b) contacting a control sample with said probe under the same conditions used in step a);
c) and detecting the presence of hybrid complexes in said samples;

wherein detection of levels of the hybrid complex in the patient sample that differ from levels of the hybrid complex in the control sample is indicative of disease.

A further aspect of the invention comprises a diagnostic method comprising the steps of:

a) obtaining a tissue sample from a patient being tested for disease;
b) isolating a nucleic acid molecule according to the invention from said tissue sample; and
c) diagnosing the patient for disease by detecting the presence of a mutation in the nucleic acid molecule which is associated with disease.

To aid the detection of nucleic acid molecules in the above-described methods, an amplification step, for example using PCR, may be included.

Deletions and insertions can be detected by a change in the size of the amplified product in comparison to the normal genotype. Point mutations can be identified by hybridizing amplified DNA to labelled RNA of the invention or alternatively, labelled antisense DNA sequences of the invention. Perfectly-matched sequences can be distinguished from mismatched duplexes by RNase digestion or by assessing differences in melting temperatures. The presence or absence of the mutation in the patient may be detected by contacting DNA with a nucleic acid probe that hybridises to the DNA under stringent conditions to form a hybrid double-stranded molecule, the hybrid double-stranded molecule having an unhybridised portion of the nucleic acid probe strand at any portion corresponding to a mutation associated with disease; and detecting the presence or absence of an unhybridised portion of the probe strand as an indication of the presence or absence of a disease-associated mutation in the corresponding portion of the DNA strand.

Such diagnostics are particularly useful for prenatal and even neonatal testing.

Point mutations and other sequence differences between the reference gene and "mutant" genes can be identified by other well-known techniques, such as direct DNA sequencing or single-strand conformational polymorphism, (see Orita et al., Genomics, 5, 874-879 (1989)). For example, a sequencing primer may be used with double-stranded PCR product or a single-stranded template molecule generated by a modified PCR. The sequence determination is performed by conventional procedures with radiolabelled nucleotides or by automatic sequencing procedures with fluorescent-tags. Cloned DNA segments may also be used as probes to detect specific DNA segments. The sensitivity of this method is greatly enhanced when combined with PCR. Further, point mutations and other sequence variations, such as polymorphisms, can be detected as described above, for example, through the use of allele-specific oligonucleotides for PCR amplification of sequences that differ by single nucleotides.

DNA sequence differences may also be detected by alterations in the electrophoretic mobility of DNA fragments in gels, with or without denaturing agents, or by direct DNA sequencing (for example, Myers et al., Science (1985) 230:1242). Sequence changes at specific locations may also be revealed by nuclease protection assays, such as RNase and S1 protection or the chemical cleavage method (see Cotton et al., Proc. Natl. Acad. Sci. USA (1985) 85:4397-4401).

In addition to conventional gel electrophoresis and DNA sequencing, mutations such as microdeletions, aneuploidies, translocations, inversions, can also be detected by in situ analysis (see, for example, Keller et al., DNA Probes, 2nd Ed., Stockton Press, New York, N.Y., USA (1993)), that is, DNA or RNA sequences in cells can be analysed for mutations without need for their isolation and/or immobilisation onto a membrane. Fluorescence in situ hybridization (FISH) is presently the most commonly applied method and numerous reviews of FISH have appeared (see, for example, Trachuck et al., Science, 250, 559-562 (1990), and Trask et al., Trends, Genet., 7, 149-154 (1991)).

In another embodiment of the invention, an array of oligonucleotide probes comprising a nucleic acid molecule according to the invention can be constructed to conduct efficient screening of genetic variants, mutations and polymorphisms. Array technology methods are well known and have general applicability and can be used to address a variety of questions in molecular genetics including gene expression, genetic linkage, and genetic variability (see for example: M. Chee et al., Science (1996), Vol 274, pp 610-613).

In one embodiment, the array is prepared and used according to the methods described in PCT application WO95/11995 (Chee et al); Lockhart, D. J. et al. (1996) Nat. Biotech. 14: 1675-1680); and Schena, M. et al. (1996) Proc. Natl. Acad. Sci. 93: 10614-10619). Oligonucleotide pairs may range from two to over one million. The oligomers are synthesized at designated areas on a substrate using a light-directed chemical process. The substrate may be paper, nylon or other type of membrane, filter, chip, glass slide or any other suitable solid support. In another aspect, an oligonucleotide may be synthesized on the surface of the substrate by using a chemical coupling procedure and an ink jet application apparatus, as described in PCT application WO95/25116 (Baldeschweiler et al.). In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and over one million which lends itself to the efficient use of commercially-available instrumentation.

In addition to the methods discussed above, diseases may be diagnosed by methods comprising determining, from a sample derived from a subject, an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods.

Assay techniques that can be used to determine levels of a polypeptide of the present invention in a sample derived from a host are well-known to those of skill in the art and are discussed in some detail above (including radioimmunoassays, competitive-binding assays, Western Blot analysis and ELISA assays). This aspect of the invention provides a diagnostic method which comprises the steps of: (a) contacting a ligand as described above with a biological sample under conditions suitable for the formation of a ligand-polypeptide complex; and (b) detecting said complex.

Protocols such as ELISA, RIA, and FACS for measuring polypeptide levels may additionally provide a basis for diagnosing altered or abnormal levels of polypeptide expression. Normal or standard values for polypeptide expression are established by combining body fluids or cell extracts taken from normal mammalian subjects, preferably humans, with antibody to the polypeptide under conditions suitable for complex formation The amount of standard complex formation may be quantified by various methods, such as by photometric means.

Antibodies which specifically bind to a polypeptide of the invention may be used for the diagnosis of conditions or diseases characterised by expression of the polypeptide, or in assays to monitor patients being treated with the polypeptides, nucleic acid molecules, ligands and other compounds of the invention. Antibodies useful for diagnostic purposes may be prepared in the same manner as those described above for therapeutics. Diagnostic assays for the polypeptide include methods that utilise the antibody and a label to detect the polypeptide in human body fluids or extracts of cells or tissues. The antibodies may be used with or without modification, and may be labelled by joining them, either covalently or non-covalently, with a reporter molecule. A wide variety of reporter molecules known in the art may be used, several of which are described above.

Quantities of polypeptide expressed in subject, control and disease samples from biopsied tissues are compared with the standard values. Deviation between standard and subject values establishes the parameters for diagnosing disease. Diagnostic assays may be used to distinguish between absence, presence, and excess expression of polypeptide and to monitor regulation of polypeptide levels during therapeutic intervention. Such assays may also be used to evaluate the efficacy of a particular therapeutic treatment regimen in animal studies, in clinical trials or in monitoring the treatment of an individual patient.

A diagnostic kit of the present invention may comprise:

(a) a nucleic acid molecule of the present invention;

(b) a polypeptide of the present invention; or (c) a ligand of the present invention.

In one aspect of the invention, a diagnostic kit may comprise a first container containing a nucleic acid probe that hybridises under stringent conditions with a nucleic acid molecule according to the invention; a second container containing primers useful for amplifying the nucleic acid molecule; and instructions for using the probe and primers for facilitating the diagnosis of disease. The kit may further comprise a third container holding an agent for digesting unhybridised RNA.

In an alternative aspect of the invention, a diagnostic kit may comprise an array of nucleic acid molecules, at least one of which may be a nucleic acid molecule according to the invention.

To detect polypeptide according to the invention, a diagnostic kit may comprise one or more antibodies that bind to a polypeptide according to the invention; and a reagent useful for the detection of a binding reaction between the antibody and the polypeptide.

Such kits will be of use in diagnosing a disease or susceptibility to diseases in which metalloproteases are implicated, particularly respiratory disorders, including emphysema and cystic fibrosis, metabolic disorders, cardiovascular disorders, bacterial infections, hypertension, proliferative disorders, including cancer, autoimmune/inflammatory disorders, including rheumatoid arthritis, neurological disorders, developmental disorders and reproductive disorders.

Various aspects and embodiments of the present invention will now be described in more detail by way of example, with particular reference to INSP005 polypeptides.

It will be appreciated that modification of detail may be made without departing from the scope of the invention.

BRIEF DESCRIPTION OF THE FIGURES

FIG. 1: Summary of results of database searches using the INSP005 predicted polypeptide sequence as a query sequence (sequence alignments shown) (SEQ ID NO:52, identified as "Query" and SEQ ID NO:53, identified as "Sbjct" for Blastp vs. NCBI-nr; SEQ ID NO:54, identified as "Query" and SEQ ID NO:55, identified as "Sbjct" for Tblastn vs. NCBI-est).

FIG. 2: Table of human cDNA libraries used in the INSP005 cloning investigation.

FIG. 3: Nucleotide sequence of the INSP005 predicted polypeptide and predicted amino acid sequence (SEQ ID NO:56).

FIG. 4: Table of INSP005 cloning primers.

FIG. 5: 3'nucleotide and amino acid sequence of INSP005 identified by RACE PCR (SEQ ID NO:57).

FIG. 6: Table of primers used during INSP005 sequencing.

FIG. 7: Putative full-length INSP005a cloned from human uterus cDNA (SEQ ID NO:58).

FIG. 8: INSP005a blastp vs. NCBI-nr database (top ten hits and top related alignment shown) (SEQ ID NO:59, identified as "Query" and SEQ ID NO:60, identified as "Sbjct").

FIG. 9: Map of PCR4-TOPO-IPAAAIPAAA7883-1 INSP005a cloning plasmid.

FIG. 10: Putative full-length INSP005b (SEQ ID NO:61) cloned from a pool of cDNAs derived from human primary lung fibroblasts, keratinocytes and osteoarthritis synovium.

FIG. 11: INSP005b blastp vs. NCBI-nr database (top ten hits and top related alignment shown) (SEQ ID NO:62, identified as "Query" and SEQ ID NO:63, identified as "Sbjct").

FIG. 12: Map of PCR-TOPO-IPAAA78836-2 INSP005b cloning plasmid.

FIG. 13: Multiple alignment of the INSP005 predicted polypeptide sequence (SEQ ID NO:66), the INSP005a cloned polypeptide sequence (SEQ ID NO:14), the INSP005b cloned polypeptide sequence (SEQ ID NO:34) and certain prior art sequences of interest (SEQ ID NO:64, WO2002/16566-A2 and SEQ ID NO:65, AX526191).

FIG. 14: SignalP signal peptide prediction data for the INSP005b polypeptide.

EXAMPLES

Example 1

INSP005 Predicted Polypeptide

Figure 15A:
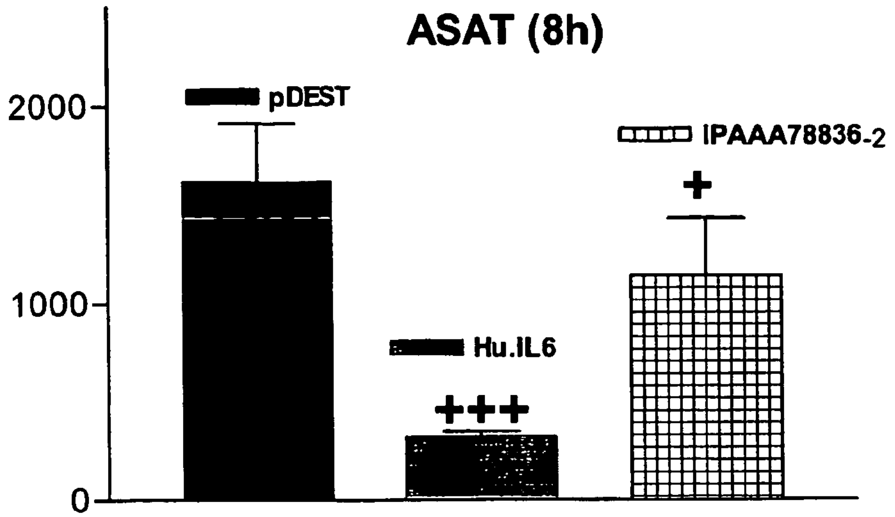
FIG. 15A: Effect of hIL-6 or INSP005b plasmid delivery on serum ASAT levels.

An INSP005 polypeptide sequence (SEQ ID NO:37) predicted by proprietary bioinformatics techniques was used as a query sequence for searches of the following databases:

| | | |
|---|---|---|
| NCBI-nr | NCBI-nt | NCBI-pat-aa |
| NCBI-pat-nt | NCBI-month-aa | NCBI-month-nt |
| NCBI-est | | |

The results of these searches are summarised in FIG. 1, which shows two relevant sequence alignments. The headings in FIG. 1 indicate which searching/alignment algorithms were used and which database was searched. These results show that the closest related match to the INSP005 predicted polypeptide sequence is the hatching enzyme EHE4 from *Anguilla japonica* (Japanese eel). These searches also identified three other prior art sequences of interest, which are discussed in more detail below.

Members of the choriolysin/astacin-like family of metalloproteases have been implicated in chorion hardening of oviparous fish eggs after fertilisation (for an example see Shibata et al. (2000) J. Biol. Chem vol. 275, No. 12 p 8349). This post-fertilisation change prevents polyspermy and corresponds to the formation of fertilisation membranes in sea urchin, amphibian and the zona reaction in mammals. They have also been implicated in the hydrolysis of the hardened chorion at the time of hatching and the hydrolysis of unfertilised egg chorions.

As described above, the identification of novel metalloproteases is of extreme importance in increasing understanding of the underlying pathways that lead to certain disease states in which these proteins are implicated, and in developing more effective gene or drug therapies to treat these disorders. Similarly, the identification of further members of the astacin/choriolysin-like family of metalloproteases is of extreme importance in increasing understanding of the underlying pathways that lead to certain disease states in which these proteins are implicated, and in developing more effective gene or drug therapies to treat these disorders.

Example 2

Summary of INSP005 Cloning 1.1 cDNA Libraries

Human cDNA libraries (in bacteriophage lambda (λ) vectors) were purchased from Stratagene or Clontech or prepared at the Serono Pharmaceutical Research Institute in λ ZAP or λ GT10 vectors according to the manufacturer's protocol (Stratagene). Bacteriophage λ DNA was prepared from small-scale cultures of infected *E. coli* host strain using the Wizard Lambda Preps DNA purification system according to the manufacturer's instructions (Promega, Corporation, Madison Wis.). The list of libraries and host strains used is shown in FIG. 2. Eight pools (A-H) of five different libraries (100 ng/μl phage DNA) were used in subsequent PCR reactions.

1.2 Generation of Reverse Transcribed cDNA Templates

Total RNA was isolated from primary human cells, human cell lines and human tissues using the Trizol™ reagent (Invitrogen) according to the manufacturer's instructions or purchased from Clontech, Invitrogen or Ambion. The quality and concentration of the RNA was analysed using an Agilent 2100 Bioanalyzer.

For cDNA synthesis the reaction mixture contained: 1 μl oligo $(dT)_{15}$ primer (500 μg/ml, Promega cat. no. C 1101), 2 μg total RNA, 1 μl 10 mM dNTPs in a volume of 12 μl. The mixture was heated to 65° C. for 5 min and then chilled on ice.

The following reagents were then added: 4 μl 5× first strand buffer, 2 μl DTT (0.1M), 1 μl RNAseOut recombinant ribonuclease inhibitor (40 units/μl, Promega, cat. no. N 2511) and incubated at 42° C. for 2 min before addition of 1 μl (200 units) of Superscript II (Invitrogen cat. no. 18064-014). The mixture was incubated at 42° C. for 50 min and then heated at 70° C. for 15 min. To remove the RNA template, 1 μl (2 units) of *E. coli* RNase H (Invitrogen cat. no. 18021-014) was added and the reaction mixture further incubated at 37° C. for 20 min. The final reaction mix was diluted to 200 μl with sterile water and stored at −80° C. cDNA pools were generated by mixing equal volumes of 5 different cDNA templates.

1.3 PCR of Virtual cDNAs from Phage Library DNA

A partial cDNA encoding INSP005 was obtained as a PCR amplification product of 248 bp using gene specific cloning primers (CP1 and CP2, FIG. 3 and FIG. 4). The PCR was performed in a final volume of 50 μl containing 1× AmpliTaq™ buffer, 200 μM dNTPs, 50 pmoles each of cloning primers, 2.5 units of AmpliTaq™ (Perkin Elmer) and 100 ng of each phage library pool DNA using an MJ Research DNA Engine, programmed as follows: 94° C., 1 min; 40 cycles of 94° C., 1 min, x° C., and y min and 72° C., (where x is the lowest Tm—5° C. and y=1 min per kb of product); followed by 1 cycle at 72° C. for 7 min and a holding cycle at 4° C.

The amplification products were visualized on 0.8 % agarose gels in 1× TAE buffer (Invitrogen) and PCR products migrating at the predicted molecular mass were purified from the gel using the Wizard PCR Preps DNA Purification System (Promega). PCR products eluted in 50 μl of sterile water were either subcloned directly or stored at −20° C.

1.4 Gene Specific Cloning Primers for PCR

Pairs of PCR primers having a length of between 18 and 25 bases were designed for amplifying the full length and partial sequence of the virtual cDNA using Primer Designer Software (Scientific & Educational Software, PO Box 72045, Durham, N.C. 27722-2045, USA). PCR primers were optimized to have a Tm close to 55±10° C. and a GC content of 40-60%. Primers were selected which had high selectivity for the target sequence INSP005 (little or no non-specific priming).

1.5 Subcloning of PCR Products

PCR products were subcloned into the topoisomerase I modified cloning vector (PCRII TOPO) using the TA cloning kit purchased from the Invitrogen Corporation using the conditions specified by the manufacturer. Briefly, 4 μl of gel purified PCR product from the human library pool N amplification was incubated for 15 min at room temperature with 1 μl of TOPO vector and 1 μl salt solution. The reaction mixture was then transformed into *E. coli* strain TOP10 (Invitrogen) as follows: a 50 μl aliquot of One Shot TOP10 cells was thawed on ice and 2 μl of TOPO reaction was added. The mixture was incubated for 15 min on ice and then heat shocked by incubation at 42° C. for exactly 30 s. Samples were returned to ice and 250 μl of warm SOC media (room temperature) was added. Samples were incubated with shaking (220 rpm) for 1 h at 37° C. The transformation mixture was then plated on L-broth (LB) plates containing ampicillin (100 μg/ml) and incubated overnight at 37° C. Ampicillin resistant colonies containing cDNA inserts were identified by colony PCR.

1.6 Colony PCR

Colonies were inoculated into 50 μl sterile water using a sterile toothpick. A 10 μl aliquot of the inoculum was then subjected to PCR in a total reaction volume of 20 μl as described above, except the primers used were SP6 and T7. The cycling conditions were as follows: 94° C., 2 min; 30 cycles of 94° C., 30 sec, 47° C., 30 sec and 72° C. for 1 cycle, 72° C., 7 min. Samples were then maintained at 4° C. (holding cycle) before further analysis.

PCR reaction products were analyzed on 1% agarose gels in 1× TAE buffer. Colonies which gave the expected PCR product size (248 bp cDNA+185 bp due to the multiple cloning site or MCS) were grown up overnight at 37° C. in 5 ml L-Broth (LB) containing ampicillin (100 μg/ml), with shaking at 220 rpm at 37° C.

1.7 Plasmid DNA Preparation and Sequencing

Miniprep plasmid DNA was prepared from 5 ml cultures using a Qiaprep Turbo 9600 robotic system (Qiagen) or Wizard Plus SV Minipreps kit (Promega cat. no. 1460) according to the manufacturer's instructions. Plasmid DNA was eluted in 100 μl of sterile water. The DNA concentration was measured using an Eppendorf BO photometer. Plasmid DNA (200-500 ng) was subjected to DNA sequencing with T7 primer and SP6 primer using the BigDyeTerminator system (Applied Biosystems cat. no. 4390246) according to the manufacturer's instructions. Sequencing reactions were purified using Dye-Ex columns (Qiagen) or Montage SEQ 96 cleanup plates (Millipore cat. no. LSKS09624) then analyzed on an Applied Biosystems 3700 sequencer.

1.8 Identification of the Full Length Sequence of INSP005 Using RACE PCR.

The predicted sequence of the INSP005 ORF is shown in FIG. 3. Attempts to isolate the full length coding sequence by PCR failed on the libraries tested, using primer pairs to amplify the full length prediction or a shorter version which uses a $2^{nd}$ predicted start site at M96 in the open reading frame. The closest related sequences to INSP005 are the astacin-like metallopeptidase in *Anguilla japonica* and choriolysin H in *Oryzias latipes*. INSP005 appears to be a human orthologue of choriolysin H. Choriolysins are implicated in chorion hardening of oviparous fish eggs after fertilization, suggesting that uterus may be a suitable source of the INSP005 mRNA. The choice of this tissue was further supported by the finding of a single EST, B1061462 derived from a human uterus tumour.

In order to identify the full coding sequence, RACE PCR was performed on cDNA prepared from uterus RNA (purchased from Clontech) using the GeneRacer kit (Invitrogen cat no. L1502-01) according to the manufacturer's instructions. For amplification of 3' ends, the first PCR was performed in a 50 μl reaction volume containing 1 μl RACE Ready cDNA, 5 μl of 10× High Fidelity buffer, 1 μl of dNTPs (10 mM), 2 μl of 50 mM $MgSO_4$, 3 μl of GeneRacer 3' primer (10 μM), 1 μl of gene specific primer (78836-GR1-3') (10 μM) and 2.5 units (0.5 μl) of Platinum Taq DNA polymerase Hi Fi (Invitrogen). The cycling conditions were as follows: 94° C., 2 min; 5 cycles of 94° C. 30 s and 72° C. 2 min; 5 cycles of 94° C., 30 s and 70° C., 5 min; 25 cycles of 94° C., 30 s, 65° C. 30 s and 68° C. 5 min; a final extension at 68° C. for 10 min and a holding cycle of 4° C. One μl of the amplification reaction was then used as a template for a nested PCR which was performed in a final reaction volume of 50 μl with the same reagents as above except for the primers. The primers for the nested PCR were 1 μl of GeneRacer 3' nested primer (10 μM) and 1 μl of nested gene specific primer (78836-GR1nest-3') (10 μM). The cycling conditions were 94° C., 2 min; 25 cycles of 94° C., 30 s, 65° C., 30 s and 68° C., 5 min; a final extension at 68° C. for 10 min and a holding cycle of 4° C. PCR products were gel purified, subcloned into pCR4-TOPO vector and sequenced as described above. All primers used are listed in FIG. 4. The nucleotide sequence and amino acid sequence of the 3' RACE product is shown in FIG. 5. The amino acid sequence encoded by the 3' RACE product has an extended C-terminal, diverging from the prediction after nucleotide position 85 which was suggestive of an alternatively spliced form.

1.9 Cloning of the Full Length Coding Sequence of INSP005 by PCR

The putative full length coding sequence of INSP005 was cloned from human uterus cDNA (prepared as described in section 1.2) by PCR in a 50 μl PCR reaction mixture as containing 2 μl uterus cDNA, 5 μl of 10× High Fidelity buffer, 1 μl of dNTPs (10 mM), 2 μl of 50 mM $MgSO_4$, 1 μl of gene specific primer 78836-FL-F (10 μM), 1 μl of reverse gene specific primer 78836-FL-R (10 μM) and 2.5 units (0.5 μl) of Platinum Taq DNA polymerase Hi Fi (Invitrogen). The cycling conditions were 94° C., 2 min; 40 cycles of 94° C., 30 s, 55° C., 30 s and 68° C., 1 min 30 s min; a final extension at 68° C. for 10 min and a holding cycle of 4° C. The amplification products were visualized on 0.8 % agarose gels in 1× TAE buffer (Invitrogen) and PCR products migrating at the predicted molecular mass (1048 bp) were purified from the gel using the Wizard PCR Preps DNA Purification System (Promega). PCR products were eluted in 50 μl of sterile water and subcloned into pCR4 TOPO vector as described in section 1.4. Several ampicillin resistant colonies were subjected to colony PCR as described in section 1.5 except that the extension time in the amplification reaction was 2 min. Colonies containing the correct size insert (1048 bp+99 bp due to the MCS) were grown up overnight at 37° C. in 5 ml L-Broth (LB) containing ampicillin (100 μg/ml), with shaking at 220 rpm at 37° C. Miniprep plasmid DNA was prepared from 5 ml cultures using a Qiaprep Turbo 9600 robotic system (Qiagen) or Wizard Plus SV Minipreps kit (Promega cat. no. 1460) according to the manufacturer's instructions and 200-500 ng of mini-prep DNA was sequenced as described in section 1.7 with T3 and T7 primers (FIG. 6). The cloned sequence is given in FIG. 7. The amino acid alignment of the cloned sequence (INSP005a) with the predicted sequence is shown in FIG. 13. The map of the resultant plasmid, pCR4-TOPO-IPAAA78836-1 (SEQ ID NO:38; plasmid ID. No. 13164) is shown in FIG. 9.

2.0 Identification of cDNA Libraries/Templates Containing INSP005

PCR products obtained with CP1 and CP2 and migrating at the correct size (248 bp) were identified in library pool N (libraries 18, 19, 20 and 21). A cDNA encoding a putative full length INSP005 (INSP005a) was isolated from uterus cDNA using 78836-FL-F and 78836-FL-R primers. Primer 78836-FL-F is located in exon 3 of the predicted sequence. No PCR products were obtained using the reverse primer (78836-FL-R) with primers located in exon 1 of the prediction.

A second putative full length version of INSP005 (INSP005b) containing an alternative 5' end was cloned from a pool of cDNAs derived from human primary lung fibroblasts, keratinocytes and osteoarthritis synovium using primers 78836-FL2-F and 78836-FL-R but was not detected in uterus. The resultant PCR product (1313 bp—FIG. 10) was subcloned into pCR4 TOPO vector using the TOPO-TA cloning kit and sequenced as described in sections 1.5-1.7. The map of the resultant plasmid, pCR4-TOPO-IPAAA78836-2 (SEQ ID NO:39; plasmid ID. No. 13296) is shown in FIG. 12.

2.1 Summary of Cloning Results

Attempts to clone the full-length INSP005 predicted polypeptide identified two variants of the INSP005 predicted polypeptide, herein referred to as INSP005a and INSP005b (FIG. 13; SEQ ID NO:14 and SEQ ID NO:34, respectively). As described above, the INSP005a and INSP005b polypeptides (and the INSP005b mature polypeptide) are herein referred to as the INSP005 polypeptides, as distinct from the INSP005 predicted polypeptide.

The nucleotide and amino acid sequences for the predicted exons within the INSP005a and INSP005b polypeptides are given in SEQ ID NOs 1-12 and SEQ ID NOs 15-32, respectively. As described above, the putative full-length nucleotide sequences of the INSP005a and INSP005b polypeptides are given in SEQ ID NOs 13 and 33, respectively. The amino acid sequences of the INSP005a and INSP005b polypeptides are given in SEQ ID NOs 14 and 34, respectively.

The relationships between the INSP005a and INSP005b polypeptides and the INSP005 predicted polypeptide and three prior art sequences of interest are shown in FIG. 13, which provides a sequence-level alignment of the sequences. These relationships will now be described in detail.

INSP005a is a putative full-length version of the INSP005 predicted polypeptide from a uterus cDNA library. This sequence differs from the original INSP005 prediction in that it has a truncated 5' end, starting at methionine 3 of the original INSP005 predicted polypeptide (see FIG. 13). INSP005a also has an extended 3' end that incorporates an extra exon relative to the INSP005 predicted polypeptide. INSP005a has six predicted exons in total. These differences were not predicted due to the low homology of those sequence elements to other metalloproteinases. In addition, there is an alternative amino acid used at position 22 of INSP005a compared to the INSP005 predicted polypeptide. INSP005a is not predicted to contain a signal peptide. INSP005a has no in frame alternative upstream start methionine before an upstream STOP codon.

The polypeptide sequence shown in SEQ ID NO:14 (INSP005a), was used as a BLAST query against the NCBI non-redundant sequence database. The top ten hits are all egg hatching-related enzymes from *Anguilla japonica* or choriolytic proteases and align to the query sequence with highly significant E-values (from $e^{-115}$ to $2e^{-41}$) (FIG. 8). FIG. 8 also shows the alignment of the INSP005a polypeptide query sequence to the sequence of the top biochemically annotated hit, the hatching enzyme HE13 from *Anguilla japonica*. These results provide strong evidence that the INSP005a polypeptide is a metalloprotease, more specifically that it is a choriolysin/astacin-like metalloprotease.

INSP005b is a putative full-length version of the INSP005 predicted polypeptide cloned from a pool of cDNAs derived from human primary lung fibroblasts, keratinocytes and osteoarthritis synovium. INSP005b subsumes the original INSP005 predicted polypeptide sequence, though two alternative amino acids are used at positions 117 and 222. It also contains three new upstream exons and one downstream exon, making INSP005b a nine exon polypeptide. The final exon is shared with INSP005a. INSP005b was not detected in uterus. These differences were not predicted due to the low homology of those sequence elements to other metalloproteinases. As described above, INSP005b is predicted to contain a signal peptide with a cleavage site between amino acids 23 and 24 (SEQ ID NOs 35 and 36; FIG. 14).

The polypeptide sequence shown in SEQ ID NO:34 (INSP005b), was used as a BLAST query against the NCBI non-redundant sequence database. The top ten hits are all egg hatching-related enzymes from *Anguilla japonica* or choriolytic proteases and align to the query sequence with highly significant E-values (from $e^{-152}$ to $4e^{-46}$) (FIG. 11). FIG. 11 also shows the alignment of the cloned polypeptide query sequence to the sequence of the top biochemically annotated hit, the hatching enzyme HE13 from *Anguilla japonica*. These results provide strong evidence that the INSP005b polypeptide is a metalloprotease, more specifically that it is a choriolysin/astacin-like metalloprotease.

The first 7 exons of INSP005b match a nucleotide sequence disclosed in WO200216566-A2, given accession number AX443328 (see FIG. 1 and FIG. 13), although the final 3' exon is not disclosed in WO200216566-A2 (Applera Corp). The nucleotide and polypeptide molecules of the present invention specifically exclude those disclosed in WO200216566-A2.

A further prior art sequence of interest is a spliced EST (BI061462.1; see FIG. 1) from uterus tumour covering exon 1 of INSP005a and exons 2, 3 and 4 of INSP005b. The direction of the EST is not given in the report and it is hard to come to a conclusion about the presence of a start methionine from the translation. However, the nucleotide and polypeptide molecules of the present invention specifically exclude the sequences disclosed in EST BI061462.1.

Another prior art sequence of interest, with accession number AX526191 (Lexicon) (FIGS. 1 and 13), is described as cDNA in the relevant database entry (disclosed in WO02/066624) and no reference is made to a possible reproductive role. It subsumes INSP005a and exons 2-8 of INSP005b. However, an alternative amino acid is used at position 127 in INSP005a compared to the corresponding amino acid in INSP005b and the AX526191 (Lexicon) sequence. The start methionine of AX526191 is covered by the uterus tumour EST described above. A signal peptide is predicted for AX526191with a probability of 0.875. The nucleotide and polypeptide molecules of the present invention do not include the sequences disclosed in WO02/066624, including that with accession number AX526191.

FIG. 13 also highlights the active site residues, which are identical in each of the polypeptides shown. This provides further compelling evidence that the INSP005a and INSP005b polypeptides are metalloproteases.

The INSP005a and INSP005b polypeptides therefore represent novel metalloproteases, and there is strong evidence that they are members of the choriolysin/astacin-like family of metalloproteases. The INSP005a and INSP005b polypeptides may therefore play important roles in physiological and pathological processes in humans, particularly in reproductive processes.

Example 3

Expression and Purification of the Cloned, His-tagged INSP005b

3.1 Expression

Human Embryonic Kidney 293 cells expressing the Epstein-Barr virus Nuclear Antigen (HEK293-EBNA, Invitrogen) were maintained in suspension in Ex-cell VPRO serum-free medium (seed stock, maintenance medium, JRH). Sixteen to 20 hours prior to transfection (Day-1), cells were seeded in 2× T225 flasks (50 ml per flask in DMEM/F12 (1:1) containing 2% FBS seeding medium (JRH) at a density of $2\times10^5$ cells/ml). The next day (transfection: day 0) the transfection took place by using the JetPEI™ reagent (2 μl/μg of plasmid DNA, PolyPlus-transfection). For each flask, 113 μg of cDNA (plasmid No. 13403) was co-transfected with 2.3 μg of GFP (fluorescent reporter gene). The transfection mix was then added to the 2× T225 flasks and incubated at 37° C. (5% $CO_2$) for 6 days. In order to increase the amount of material, this procedure was repeated with two extra flasks to generate 200 ml total. Confirmation of positive transfection was carried out by qualitative fluorescence examination at day 6 (Axiovert 10 Zeiss).

On day 6 (harvest day), supernatants (200 ml) from the four flasks were pooled and centrifuged (4° C., 400 g) and placed into a pot bearing a unique identifier.

One aliquot (500 ul) was kept for QC of the 6His-tagged protein (internal bioprocessing QC). The corresponding delivery sheet can be found in T. Battle's notebook 11140 p 28.

For extra production purposes, batch 2 was produced in 500 ml spinner transfection, as follows:

Human Embryonic Kidney 293 cells expressing the Epstein-Barr virus Nuclear Antigen (HEK293-EBNA, Invitrogen) were maintained in suspension in Ex-cell VPRO serum-free medium (seed stock, maintenance medium, JRH). On the day of transfection, cells were counted, centrifuged (low speed) and the pellet re-suspended into the desired volume of FEME medium (see below) supplemented with 1% FCS to yield a cell concentration of 1×E 6 viable cells/ml. The #13403 cDNA was diluted at 2 mg/liter volume (co-transfected with 2% eGFP) in FEME (200 ml/liter volume). PolyEthyleneImine transfection agent (4 mg/liter volume) was then added to the cDNA solution, vortexed and incubated at room temperature for 10 minutes (generating the transfection Mix).

This transfection mix was then added to the spinner and incubated for 90 minutes in a $CO_2$ incubator (5% $CO_2$ and 37° C.). Fresh FEME medium (1% FCS) was added after 90 minutes to double the initial spinner volume. The spinner was then incubated for 6 days. On day 6 (harvest day), spinner supernatant (500 ml) was centrifuged (4° C., 400 g) and placed into a pot bearing a unique identifier with plasmid number and fermentation number.

One aliquot (500 μl) was kept for QC of the 6His-tagged protein (internal bioprocessing QC).

3.2 Purification Process

The 200 ml culture medium sample containing the recombinant protein with a C-terminal 6His tag was diluted to a final volume of 400 ml with cold buffer A (50 mM $NaH_2PO_4$; 600 mM NaCl; 8.7% (w/v) glycerol, pH 7.5). The sample was filtered through a 0.22 um sterile filter (Millipore, 500 ml filter unit) and kept at 4° C. in a 500 ml sterile square media bottle (Nalgene).

The 500 ml culture medium sample was diluted to a final volume of 1000 ml with cold buffer A. The sample was filtered through a 0.22 um sterile filter (Millipore, 500 ml filter unit) and kept at 4° C. in a 1000 ml sterile square media bottle (Nalgene).

The purifications were performed at 4° C. on the VISION workstation (Applied Biosystems) connected to an automatic sample loader (Labomatic). The purification procedure was composed of two sequential steps, metal affinity chromatography on a Poros 20 MC (Applied Biosystems) column charged with Ni ions (4.6×50 mm, 0.83 ml), followed by a buffer exchange on a Sephadex G-25 medium (Amersham Pharmacia) gel filtration column (1.0×15 cm).

For the first chromatography step the metal affinity column was regenerated with 30 column volumes of EDTA solution (100 mM EDTA; 1 M NaCl; pH 8.0), recharged with Ni ions through washing with 15 column volumes of a 100 mM $NiSO_4$ solution, washed with 10 column volumes of buffer A, followed by 7 column volumes of buffer B (50 mM $NaH_2PO_4$; 600 mM NaCl; 8.7% (w/v) glycerol, 400 mM; imidazole, pH 7.5), and finally equilibrated with 15 column volumes of buffer A containing 15 mM imidazole. The sample was transferred, by the Labomatic sample loader, into a 200 ml sample loop and subsequently charged onto the Ni metal affinity column at a flow rate of 10 ml/min. The charging procedure was repeated 2 and 5 times, respectively in order to transfer the entire sample volume (400 or 1000 ml) onto the Ni column. The column was subsequently washed with 12 column volumes of buffer A, followed by 28 column volumes of buffer A containing 20 mM imidazole. During the 20 mM imidazole wash loosely attached contaminating proteins were elution of the column. The recombinant His-tagged protein was finally eluted with 10 column volumes of buffer B at a flow rate of 2 ml/min, and the eluted protein was collected in a 1.6 ml fraction.

For the second chromatography step, the Sephadex G-25 gel-filtration column was regenerated with 2 ml of buffer D (1.137 M NaCl; 2.7 mM KCl; 1.5 mM $KH_2PO_4$; 8 mM $Na_2HPO_4$; pH 7.2), and subsequently equilibrated with 4 column volumes of buffer C (137 mM NaCl; 2.7 mM KCl; 1.5 mM $KH_2PO_4$; 8 mM $Na_2HPO_4$; 20% (w/v) glycerol; pH 7.4). The peak fraction eluted from the Ni-column was automatically through the integrated sample loader on the VISION loaded onto the Sephadex G-25 column and the protein was eluted with buffer C at a flow rate of 2 ml/min. The protein sample from the Sephadex G-25 column was recovered in a 2.2 ml fraction. The fraction was filtered through a 0.22 um sterile centrifugation filter (Millipore), frozen and stored at −80C. An aliquot of the sample was analyzed on SDS-PAGE (4-12% NuPAGE gel; Novex) by coomassie staining and Western blot with anti-His antibodies.

Coomassie staining. The NuPAGE gel was stained in a 0.1% coomassie blue R250 staining solution (30% methanol, 10% acetic acid) at room temperature for 1 h and subsequently destained in 20% methanol, 7.5% acetic acid until the background was clear and the protein bands clearly visible.

Western blot. Following the electrophoresis the proteins were electrotransferred from the gel to a nitrocellulose membrane at 290 mA for 1 hour at 4° C. The membrane was blocked with 5% milk powder in buffer E (137 mM NaCl; 2.7 mM KCl; 1.5 mM $KH_2PO_4$; 8 mM $Na_2HPO_4$; 0.1% Tween 20, pH 7.4) for 1 h at room temperature, and subsequently incubated with a mixture of 2 rabbit polyclonal anti-His antibodies (G-18 and H-15, 0.2 ug/ml each; Santa Cruz) in 2.5% milk powder in buffer E overnight at 4° C. After further 1 hour incubation at room temperature, the membrane was washed with buffer E (3×10 min), and then incubated with a secondary HRP-conjugated anti-rabbit antibody (DAKO, HRP 0399) diluted 1/3000 in buffer E containing 2.5% milk powder for 2 hours at room temperature. After washing with buffer E (3×10 minutes), the membrane was developed with the ECL kit (Amersham Pharmacia) for 1 min. The membrane was subsequently exposed to a Hyperfilm (Amersham Pharmacia), the film developed and the western blot image visually analyzed.

Protein assay. The protein concentration was determined using the BCA protein assay kit (Pierce) with bovine serum albumin as standard. 78 and 90 μg purified protein was recovered from the 200 ml and 500 ml culture medium samples, respectively.

Example 4

INSP005b in Mouse Model of Fulminant Liver Hepatitis

4.1 Introduction

In order to characterise INSP005b in vivo, the muscle electrotransfer technique was used to express INSP005b protein in the circulation of WT and ConA treated animals. No significant changes in serum transaminase levels or TNF-alpha, IFN-gamma, IL-6, IL-4 or MCP-1 cytokine levels were observed after electrotransfer of INSP005b in WT animals. Electroporated animals were then challenged with ConA in order to determine INSP005b effects on serum cytokine levels and transaminase levels.

4.2 Background—Concanavalin A (ConA)-induced Liver Hepatitis

Toxic liver disease represents a worldwide health problem in humans for which pharmacological treatments have yet to be discovered. For instance active chronic hepatitis leading to liver cirrhosis is a disease state, in which liver parenchymal cells are progressively destroyed by activated T cells. ConA-induced liver toxicity is one of three experimental models of T-cell dependent apoptotic and necrotic liver injury described in mice. Gal N (D-Galactosamine) sensitized mice challenged with either activating anti-CD3 monoclonal AB or with superantigen SEB develop severe apoptotic and secondary necrotic liver injury (Kusters S, Gastroenterology. 1996 August; 111(2):462-71). Injection of the T-cell mitogenic plant lectin ConA to non-sensitized mice results also in hepatic apoptosis that precedes necrosis. ConA induces the release of systemic TNF-alpha and IFN-gamma and various other cytokines. Both TNF-alpha and IFN-gamma are critical mediators of liver injury. Transaminase release 8 hours after the insult indicates severe liver destruction. Several cell types have been shown to be involved in liver damage, CD4 T cells, macrophages and natural killer cells (Kaneko J Exp Med 2000, 191, 105-114). Anti-CD4 antibodies block activation of T cells and consequently liver damage (Tiegs et al. 1992, J Clin Invest 90, 196-203). Pre-treatment of mice with monoclonal antibodies against CD8 failed to protect, whereas deletion of macrophages prevented the induction of hepatitis.

The present study was undertaken to investigate the role of INSP005b, a choriolysin like protein, in ConA-induced liver hepatitis. Several cytokines have been shown either to be critical in inducing or in conferring protection from ConA-induced liver damage. TNF-alpha for example is one of the first cytokines produced after ConA injection and anti-TNF-alpha antibodies confer protection against disease (Seino et al. 2001, Annals of surgery 234, 681). IFN-gamma appears also to be a critical mediator of liver injury, since anti-IFN-gamma antiserum significantly protect mice, as measured by decreased levels of transaminases in the blood of ConA-treated animals (see Kusters et al., above). In liver injury, increased production of IFN-gamma was observed in patients with autoimmune or viral hepatitis. In addition transgenic mice expressing IFN-gamma in the liver develop liver injury resembling chronic active hepatitis (Toyonaga et al. 1994, PNAS 91, 614-618). IFN-gamma may also be cytotoxic to hepatocytes, since in vitro IFN-gamma induces cell death in mouse hepatocytes that was accelerated by TNF (Morita et al. 1995, Hepatology 21, 1585-1593).

Other molecules have been described to be protective in the ConA model. A single administration of rhIL-6 completely inhibited the release of transaminases (Mizuhara et al. 1994, J. Exp. Med. 179, 1529-1537).

4.3 cDNA Electrotransfer into Muscle Fibers in Order to Achieve Systemic Expression of a Protein of Interest Among the non-viral techniques for gene transfer in vivo, the direct injection of plasmid DNA into the muscle and subsequent electroporation is simple, inexpensive and safe. The post-mitotic nature and longevity of myofibers permits stable expression of transfected genes, although the transfected DNA does not usually undergo chromosomal integration (Somiari et al. 2000, Molecular Therapy 2, 178). Several reports have demonstrated that secretion of muscle-produced proteins into the blood stream can be achieved after electroporation of corresponding cDNAs (Rizzuto et al. PNAS, 1996, 6417; Aihara H et al., 1998, Nature Biotech 16, 867). In addition in vivo efficacy of muscle expressed Epo and IL-18BP in disease models has been shown (Rizzuto, 2000, Human Gene Therapy 41, 1891; Mallat, 2001, Circulation research 89, 41).

4.4 Materials and Methods 4.4.1 Animals

In all of the studies male C57/BL6 male (8 weeks of age) were used. In general, 10 animals per experimental group are used. Mice were maintained in standard conditions under a 12-hour light-dark cycle, provided irradiated food and water ad libitum.

4.4.2 Muscle Electrotransfer 4.4.2.1 Choice of Vector

His or StrepII tagged IL6 and INSP005b (IPAAA78836-2) genes were cloned in the Gateway compatible pDEST12.2 vector containing the CMV promoter.

4.4.2.2 Electroporation Protocol

Mice were anaesthetised with gas (isofluran Baxter, Ref: ZDG9623). Hindlimbs were shaved and an echo graphic gel was applied. Hyaluronidase was injected in the posterior tibialis muscle with (20 U in 50 µl sterile NaCl 0.9%, Sigma Ref. H3631). After 10 min, 100 µg of plasmid (50 µg per leg in 25 µl of sterile NaCl 0.9%) was injected in the same muscle. The DNA was prepared in the Buffer PBS-L-Glutamate (6 mg/ml; L-Glutamate Sigma P4761) before intramuscular injection. For electrotransfer, the electric field was applied for each leg with the ElectroSquarePorator BTX ref ECM830 at 75 Volts during 20 ms for each pulse, 10 pulses with an interval of 1 second in a unipolar way with 2 round electrodes (size 0.5 mm diameter).

4.4.3 The ConA Model 4.4.3.1 ConA I.V. Injection and Blood Sampling 8 weeks old Female Mice C57/B16 were purchased from IFFA CREDO. ConA (Sigma ref. C7275) was injected at 18 mg/kg i.v. and blood samples were taken at 1.30 and 8 hours post injection. At the time of sacrifice, blood was taken from the heart.

4.4.3.2 Detection of Cytokines and Transaminases in Blood Samples

IL2, IL5, IL4, TNF-alpha and IFN-gamma cytokine levels were measured using the TH1/TH2 CBA assay. TNF-alpha, IL-6, MCP1, IFN-alpha, IL-10 and IL-12 were detected using the Inflammation CBA assay. Transaminase blood parameters were determined using the COBAS instrument (Hitachi).

4.4.3.3 INSP0005b and IL-6 Electrotransfer

At day 0 electrotransfer of pDEST12.2.INSP005b, pDEST12.2-hIL-6 as well as and the empty vector control (electrotransfer protocol see above) was performed. At day 5 after electrotransfer, ConA (18 mg/kg) was injected i.v. and blood sampled at 2 time points (1.30, 8 hours). Cytokine and ASAT ALAT measurements were performed like described above.

4.5 Results

Figure 15B:
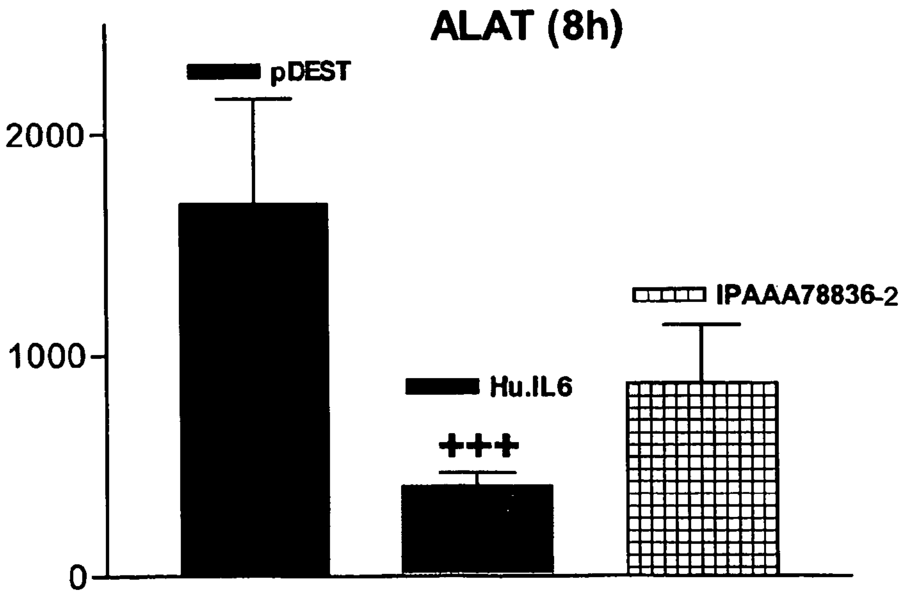
FIG. 15B: Effect of hIL-6 or INSP005b plasmid delivery on serum ALAT levels.
Figure 16A:
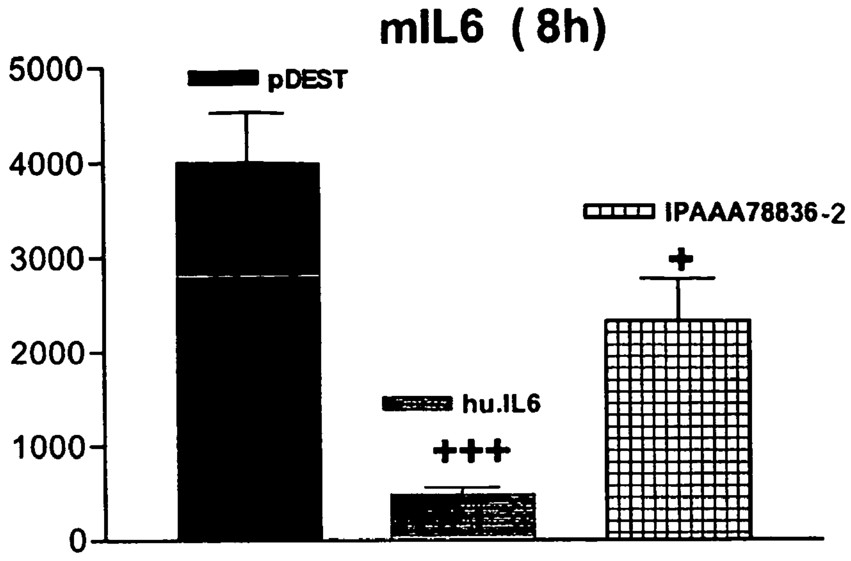
FIG. 16A: Effect of hIL-6 or INSP005b plasmid delivery on serum mIL-6 levels.
Figure 16B:
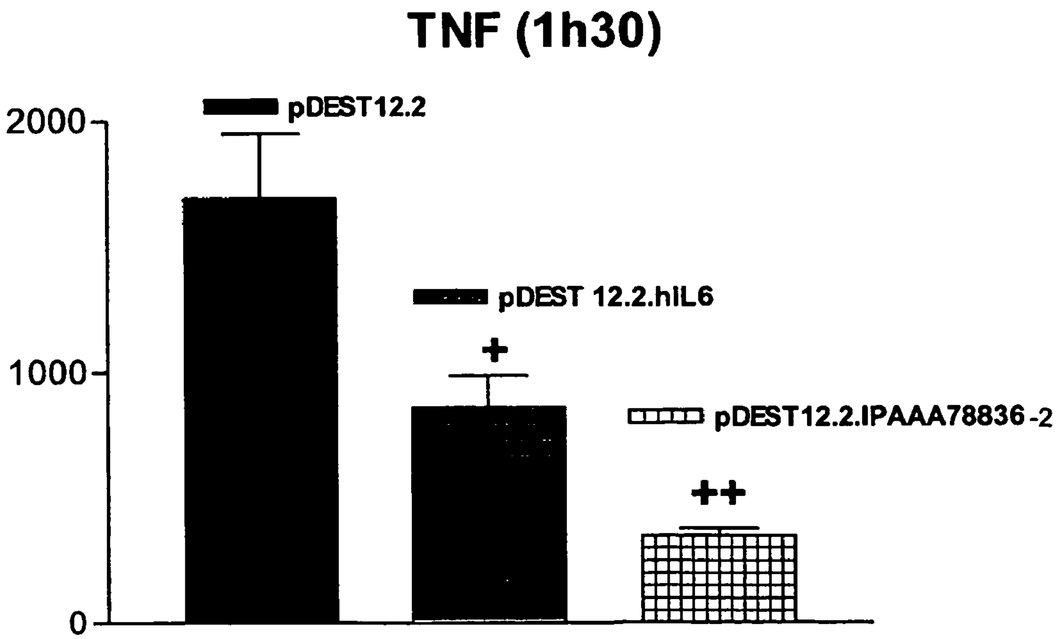
FIG. 16B: Effect of hIL-6 or INSP005b plasmid delivery on serum TNF-alpha levels.

We have found that INSP005b protects from liver injury in a mouse model mimicking fulminant hepatitis after systemic delivery of the protein using electrotransfer. FIGS. 15A and 15B show that INSP005b-eletrotransferred animals show a decrease in transaminases levels as compared to empty vector control animals 8 hours after the ConA challenge. In addition both TNF-alpha and IL-6 cytokine levels are significantly reduced in these animals (FIGS. 16A and 16B). The effect is similar to that obtained with the positive control vector pDEST12.2hIL-6-SII.

4.6 Conclusion

These results show that delivery of INSP005b cDNA in an in vivo model of fulminant hepatitis decreases TNF-alpha and m-IL-6 levels in serum and had a significant effect on the reduction of ASAT and ALAT levels measured in serum.

The decrease in ASAT and ALAT levels might be due to the decreased TNF-alpha and IL-6 levels. TNF-alpha is an important cytokine involved in the liver damage after ConA injection. In this mouse model of liver hepatitis TNF-alpha is mainly produced by hepatic macrophages, the so-called Kupfer cells. Anti TNF-alpha antibodies confer protection against disease (Seino et al. 2001, Annals of surgery 234, 681).

---

The invention claimed is:

1. An isolated polypeptide selected from the group consisting of:

a) a polypeptide comprising SEQ ID NO: 34;

b) a polypeptide consisting of SEQ ID NO: 34;

c) a polypeptide having at least 97% sequence identity to SEQ ID NO: 34 and having metalloprotease activity; and d) a fusion protein comprising a heterologous sequence fused to: SEQ ID NO: 34; or a polypeptide having at least 97% sequence identity to SEQ ID NO: 34 and having metalloprotease activity.

2. The isolated polypeptide according to claim 1, wherein said polypeptide comprises SEQ ID NO: 34.

3. The isolated polypeptide according to claim 1, wherein said polypeptide consists of SEQ ID NO: 34.

4. The isolated polypeptide according to claim 1, wherein said polypeptide has at least 97% sequence identity to SEQ ID NO: 34 and has metalloprotease activity.

5. The isolated polypeptide according to claim 1, wherein said polypeptide is a fusion protein comprising a heterologous sequence fused to: SEQ ID NO: 34; or a polypeptide having at least 97% sequence identity to SEQ ID NO: 34 and having metalloprotease activity.

6. The isolated polypeptide according to claim 5, wherein said polypeptide is a fusion protein comprising a heterologous sequence fused to SEQ ID NO: 34.

7. The isolated polypeptide according to claim 5, wherein said polypeptide is a fusion protein comprising a heterologous sequence fused to a polypeptide having at least 97% sequence identity to SEQ ID NO: 34 and having metalloprotease activity.

8. The isolated polypeptide according to claim 1, wherein said polypeptide has at least 98% sequence identity to SEQ ID NO: 34 and has metalloprotease activity.

9. The isolated polypeptide according to claim 1, wherein said polypeptide is a fusion protein comprising a heterologous sequence fused to a polypeptide having at least 98% sequence identity to SEQ ID NO: 34 and having metalloprotease activity.

10. The isolated polypeptide according to claim 1, wherein said polypeptide has at least 99% sequence identity to SEQ ID NO: 34 and has metalloprotease activity.

11. The isolated polypeptide according to claim 1, wherein said polypeptide is a fusion protein comprising a heterologous sequence fused to a polypeptide having at least 99% sequence identity to SEQ ID NO: 34 and having metalloprotease activity.

12. A pharmaceutical composition comprising a pharmaceutically acceptable carrier and a polypeptide selected from the group consisting of:

a) a polypeptide comprising SEQ ID NO: 34;

b) a polypeptide consisting of SEQ ID NO: 34;

c) a polypeptide having at least 97% sequence identity to SEQ ID NO: 34 and having metalloprotease activity; and d) a fusion protein comprising a heterologous sequence fused to: SEQ ID NO: 34; or a polypeptide having at least 97% sequence identity to SEQ ID NO: 34 and having metalloprotease activity.

13. The pharmaceutical composition according to claim 12, wherein said polypeptide comprises SEQ ID NO: 34.

14. The pharmaceutical composition according to claim 12, wherein said polypeptide consists of SEQ ID NO: 34.

15. The pharmaceutical composition according to claim 12, wherein said polypeptide has at least 97% sequence identity to SEQ ID NO: 34 and has metalloprotease activity.

16. The pharmaceutical composition according to claim 12, wherein said polypeptide is a fusion protein comprising a heterologous sequence fused to: SEQ ID NO: 34; or a polypeptide having at least 97% sequence identity to SEQ ID NO: 34 and having metalloprotease activity.

17. The pharmaceutical composition according to claim 16, wherein said polypeptide is a fusion protein comprising a heterologous sequence fused to SEQ ID NO: 34.

18. The pharmaceutical composition according to claim 16, wherein said polypeptide is a fusion protein comprising a heterologous sequence fused to a polypeptide having at least 97% sequence identity to SEQ ID NO: 34 and having metalloprotease activity.

19. The pharmaceutical composition according to claim 12, wherein said polypeptide has at least 98% sequence identity to SEQ ID NO: 34 and has metalloprotease activity.

20. The pharmaceutical composition according to claim 12, wherein said polypeptide is a fusion protein comprising a heterologous sequence fused to a polypeptide having at least 98 % sequence identity to SEQ ID NO: 34 and having metalloprotease activity.

21. The pharmaceutical composition according to claim 12, wherein said polypeptide has at least 99% sequence identity to SEQ ID NO: 34 and has metalloprotease activity.

22. The pharmaceutical composition according to claim 12, wherein said polypeptide is a fusion protein comprising a heterologous sequence fused to a polypeptide having at least 99% sequence identity to SEQ ID NO: 34 and having metalloprotease activity.

23. An immunogenic composition comprising an adjuvant and a polypeptide selected from the group consisting of:

a) a polypeptide comprising SEQ ID NO: 34;

b) a polypeptide consisting of SEQ ID NO: 34;

c) a polypeptide having at least 97% sequence identity to SEQ ID NO: 34 and having metalloprotease activity; and d) a fusion protein comprising a heterologous sequence fused to: SEQ ID NO: 34; or a polypeptide having at least 97% sequence identity to SEQ ID NO: 34 and having metalloprotease activity.

24. The immunogenic composition according to claim 23, wherein said polypeptide comprises SEQ ID NO: 34.

25. The immunogenic composition according to claim 23, wherein said polypeptide consists of SEQ ID NO: 34.

26. The immunogenic composition according to claim 23, wherein said polypeptide has at least 97% sequence identity to SEQ ID NO: 34 and has metalloprotease activity.

27. The immunogenic composition according to claim 23, wherein said polypeptide is a fusion protein comprising a heterologous sequence fused to: SEQ ID NO: 34; or a polypeptide having at least 97% sequence identity to SEQ ID NO: 34 and having metalloprotease activity.

28. The immunogenic composition according to claim 27, wherein said polypeptide is a fusion protein comprising a heterologous sequence fused to SEQ ID NO: 34.

29. The immunogenic composition according to claim 27, wherein said polypeptide is a fusion protein comprising a heterologous sequence fused to a polypeptide having at least 97% sequence identity to SEQ ID NO: 34 and having metalloprotease activity.

30. The immunogenic composition according to claim 23, wherein said polypeptide has at least 98% sequence identity to SEQ ID NO: 34 and has metalloprotease activity.

31. The immunogenic composition according to claim 23, wherein said polypeptide is a fusion protein comprising a heterologous sequence fused to a polypeptide having at least 98% sequence identity to SEQ ID NO: 34 and having metalloprotease activity.

32. The immunogenic composition according to claim 23, wherein said polypeptide has at least 99% sequence identity to SEQ ID NO: 34 and has metalloprotease activity.

33. The immunogenic composition according to claim 23, wherein said polypeptide is a fusion protein comprising a heterologous sequence fused to a polypeptide having at least 99% sequence identity to SEQ ID NO: 34 and having metalloprotease activity.

34. A method of treating viral or acute liver disease comprising administering, to an individual having viral or acute liver disease, a pharmaceutical composition comprising a carrier and a polypeptide selected from the group consisting of:

a) a polypeptide comprising SEQ ID NO: 34;

b) a polypeptide consisting of SEQ ID NO: 34;

c) a polypeptide having at least 97% sequence identity to SEQ ID NO: 34 and having metalloprotease activity; and d) a fusion protein comprising a heterologous sequence fused to: SEQ ID NO: 34; or a polypeptide having at least 97% sequence identity to SEQ ID NO: 34 and having metalloprotease activity;

wherein said pharmaceutical composition is administered in an amount effective to treat said viral or acute liver disease.

35. The method according to claim 34, wherein said polypeptide comprises SEQ ID NO: 34.

36. The method according to claim 34, wherein said polypeptide consists of SEQ ID NO: 34.

37. The method according to claim 34, wherein said polypeptide has at least 97% sequence identity to SEQ ID NO: 34 and has metalloprotease activity.

38. The method according to claim 34, wherein said polypeptide is a fusion protein comprising a heterologous sequence fused to: SEQ ID NO: 34; or a polypeptide having at least 97% sequence identity to SEQ ID NO: 34 and having metalloprotease activity.

39. The method according to claim 38, wherein said polypeptide is a fusion protein comprising a heterologous sequence fused to SEQ ID NO: 34.

40. The method according to claim 38, wherein said polypeptide is a fusion protein comprising a heterologous sequence fused to a polypeptide having at least 97% sequence identity to SEQ ID NO: 34 and having metalloprotease activity.

41. The method according to claim 34, wherein said acute liver disease is alcoholic liver failure.

42. The method according to claim 34, wherein said polypeptide has at least 98% sequence identity to SEQ ID NO: 34 and has metalloprotease activity.

43. The method according to claim 34, wherein said polypeptide is a fusion protein comprising a heterologous sequence fused to a polypeptide having at least 98% sequence identity to SEQ ID NO: 34 and having metalloprotease activity.

44. The method according to claim 34, wherein said polypeptide has at least 99% sequence identity to SEQ ID NO: 34 and has metalloprotease activity.

45. The method according to claim 34, wherein said polypeptide is a fusion protein comprising a heterologous sequence fused to a polypeptide having at least 99% sequence identity to SEQ ID NO: 34 and having metalloprotease activity.

* * * * *

UNITED STATES PATENT AND TRADEMARK OFFICE

CERTIFICATE OF CORRECTION

PATENT NO. : 7,557,079 B2 Page 1 of 1
APPLICATION NO. : 10/539847
DATED : July 7, 2009
INVENTOR(S) : Richard Joseph Fagan et al.

It is certified that error appears in the above-identified patent and that said Letters Patent is hereby corrected as shown below:

<u>Column 35,</u>
Line 45, "(PCRII TOPO)" should read --(pCRII TOPO)--.

<u>Column 36,</u>
Line 2, "and 72° C, for 1 cycle" should read --and 72° C for 1 min); 1 cycle--.

Signed and Sealed this

Eighth Day of September, 2009

David J. Kappos

David J. Kappos
*Director of the United States Patent and Trademark Office*

SEQUENCE LISTING

<160> NUMBER OF SEQ ID NOS: 51

<210> SEQ ID NO 1
<211> LENGTH: 52
<212> TYPE: DNA
<213> ORGANISM: Homo sapiens

<400> SEQUENCE: 1
atgggtggta gtggtgtcgt ggaggtcccc ttcctgctct ccagcaagta cg 52

<210> SEQ ID NO 2
<211> LENGTH: 18
<212> TYPE: PRT
<213> ORGANISM: Homo sapiens

<400> SEQUENCE: 2

Met Gly Gly Ser Gly Val Val Glu Val Pro Phe Leu Leu Ser Ser Lys

-continued 1 5 10 15

Tyr Asp

<210> SEQ ID NO 3
<211> LENGTH: 118
<212> TYPE: DNA
<213> ORGANISM: Homo sapiens

<400> SEQUENCE: 3
atgagcccag ccgccaggtc atcctggagg ctcttgcgga gtttgaacgt tccacgtgca 60
tcaggtttgt cacctatcag gaccagagag acttcatttc catcatcccc atgtatgg 118

<210> SEQ ID NO 4
<211> LENGTH: 39
<212> TYPE: PRT
<213> ORGANISM: Homo sapiens

<400> SEQUENCE: 4

Glu Pro Ser Arg Gln Val Ile Leu Glu Ala Leu Ala Glu Phe Glu Arg
1 5 10 15

Ser Thr Cys Ile Arg Phe Val Thr Tyr Gln Asp Gln Arg Asp Phe Ile
20 25 30

Ser Ile Ile Pro Met Tyr Gly
35

<210> SEQ ID NO 5
<211> LENGTH: 182
<212> TYPE: DNA
<213> ORGANISM: Homo sapiens

<400> SEQUENCE: 5
gtgcttctcg agtgtggggc gcagtggagg gatgcaggtg gtctccctgg cgcccacgtg 60
tctccagaag ggccggggca ttgtccttca tgagctcatg catgtgctgg gcttctggca 120
cgagcacacg cgggccgacc gggaccgcta tatccgtgtc aactggaacg agatcctgcc 180
ag 182

<210> SEQ ID NO 6
<211> LENGTH: 61
<212> TYPE: PRT
<213> ORGANISM: Homo sapiens

<400> SEQUENCE: 6

Cys Phe Ser Ser Val Gly Arg Ser Gly Gly Met Gln Val Val Ser Leu
1 5 10 15

Ala Pro Thr Cys Leu Gln Lys Gly Arg Gly Ile Val Leu His Glu Leu
20 25 30

Met His Val Leu Gly Phe Trp His Glu His Thr Arg Ala Asp Arg Asp
35 40 45

Arg Tyr Ile Arg Val Asn Trp Asn Glu Ile Leu Pro Gly
50 55 60

<210> SEQ ID NO 7
<211> LENGTH: 82
<212> TYPE: DNA
<213> ORGANISM: Homo sapiens

<400> SEQUENCE: 7
gctttgaaat caacttcatc aagtctcaga gcagcaacat gctgacgccc tatgactact 60
cctctgtgat gcactatggg ag 82

<210> SEQ ID NO 8
<211> LENGTH: 27
<212> TYPE: PRT
<213> ORGANISM: Homo sapiens

<400> SEQUENCE: 8

Phe Glu Ile Asn Phe Ile Lys Ser Gln Ser Ser Asn Met Leu Thr Pro
1 5 10 15

Tyr Asp Tyr Ser Ser Val Met His Tyr Gly Arg
20 25

<210> SEQ ID NO 9
<211> LENGTH: 155
<212> TYPE: DNA
<213> ORGANISM: Homo sapiens

<400> SEQUENCE: 9
gctcgccttc agccggcgtg ggctgcccac catcacacca ctttgggccc ccagtgtcca 60
catcggccag cgatggaacc tgagtgcctc ggacatcacc cgggtcctca aactctacgg 120
ctgcagccca agtggcccca ggccccgtgg gagag 155

<210> SEQ ID NO 10
<211> LENGTH: 52
<212> TYPE: PRT
<213> ORGANISM: Homo sapiens

<400> SEQUENCE: 10

Leu Ala Phe Ser Arg Arg Gly Leu Pro Thr Ile Thr Pro Leu Trp Ala
1 5 10 15

Pro Ser Val His Ile Gly Gln Arg Trp Asn Leu Ser Ala Ser Asp Ile
20 25 30

Thr Arg Val Leu Lys Leu Tyr Gly Cys Ser Pro Ser Gly Pro Arg Pro
35 40 45

Arg Gly Arg Gly
50

<210> SEQ ID NO 11
<211> LENGTH: 419
<212> TYPE: DNA
<213> ORGANISM: Homo sapiens

<400> SEQUENCE: 11
ggtcccatgc ccacagcact ggtaggagcc ccgccccggc ctccctatct ctgcagcggc 60
ttttggaggc actgtcggcg gaatccagga gccccgaccc cagtggttcc agtgcgggag 120
gccagcccgt tcctgcaggg cctggggaga gcccacatgg gtgggagtcc cctgccctga 180
aaaagctcag tgcagaggcc tcggcaaggc agcctcagac cctagcttcc tccccaagat 240
caaggcctgg agcaggtgcc cccggtgttg ctcaggagca gtcctggctg gccggagtgt 300
ccaccaagcc cacagtccca tcttcagaag caggaatcca gccagtccct gtccagggaa 360
gcccagctct gccagggggc tgtgtaccta gaaatcattt caaggggatg tccgaagat 419

<210> SEQ ID NO 12
<211> LENGTH: 139
<212> TYPE: PRT
<213> ORGANISM: Homo sapiens

<400> SEQUENCE: 12

-continued

Ser His Ala His Ser Thr Gly Arg Ser Pro Ala Pro Ala Ser Leu Ser
1 5 10 15

Leu Gln Arg Leu Leu Glu Ala Leu Ser Ala Glu Ser Arg Ser Pro Asp
20 25 30

Pro Ser Gly Ser Ser Ala Gly Gly Gln Pro Val Pro Ala Gly Pro Gly
35 40 45

Glu Ser Pro His Gly Trp Glu Ser Pro Ala Leu Lys Lys Leu Ser Ala
50 55 60

Glu Ala Ser Ala Arg Gln Pro Gln Thr Leu Ala Ser Ser Pro Arg Ser
65 70 75 80

Arg Pro Gly Ala Gly Ala Pro Gly Val Ala Gln Glu Gln Ser Trp Leu
85 90 95

Ala Gly Val Ser Thr Lys Pro Thr Val Pro Ser Ser Glu Ala Gly Ile
100 105 110

Gln Pro Val Pro Val Gln Gly Ser Pro Ala Leu Pro Gly Gly Cys Val
115 120 125

Pro Arg Asn His Phe Lys Gly Met Ser Glu Asp
130 135

<210> SEQ ID NO 13
<211> LENGTH: 1008
<212> TYPE: DNA
<213> ORGANISM: Homo sapiens

<400> SEQUENCE: 13
atgggtggta gtggtgtcgt ggaggtcccc ttcctgctct ccagcaagta cgatgagccc 60
agccgccagg tcatcctgga ggctcttgcg gagtttgaac gttccacgtg catcaggttt 120
gtcacctatc aggaccagag agacttcatt tccatcatcc ccatgtatgg gtgcttctcg 180
agtgtggggc gcagtggagg gatgcaggtg gtctccctgg cgcccacgtg tctccagaag 240
ggccggggca ttgtccttca tgagctcatg catgtgctgg gcttctggca cgagcacacg 300
cgggccgacc gggaccgcta tatccgtgtc aactggaacg agatcctgcc aggctttgaa 360
atcaacttca tcaagtctca gagcagcaac atgctgacgc cctatgacta ctcctctgtg 420
atgcactatg ggaggctcgc cttcagccgg cgtgggctgc ccaccatcac accactttgg 480
gcccccagtg tccacatcgg ccagcgatgg aacctgagtg cctcggacat cacccgggtc 540
ctcaaactct acggctgcag cccaagtggc cccaggcccc gtgggagagg gtcccatgcc 600
cacagcactg gtaggagccc cgccccggcc tccctatctc tgcagcggct tttggaggca 660
ctgtcggcgg aatccaggag ccccgacccc agtggttcca gtgcgggagg ccagcccgtt 720
cctgcagggc ctggggagag cccacatggg tgggagtccc ctgccctgaa aaagctcagt 780
gcagaggcct cggcaaggca gcctcagacc ctagcttcct ccccaagatc aaggcctgga 840
gcaggtgccc ccggtgttgc tcaggagcag tcctggctgg ccggagtgtc caccaagccc 900
acagtcccat cttcagaagc aggaatccag ccagtccctg tccagggaag cccagctctg 960 ccaggggggct gtgtacctag aaatcatttc aaggggatgt ccgaagat 1008

<210> SEQ ID NO 14
<211> LENGTH: 336
<212> TYPE: PRT
<213> ORGANISM: Homo sapiens

<400> SEQUENCE: 14

Met Gly Gly Ser Gly Val Val Glu Val Pro Phe Leu Leu Ser Ser Lys

-continued

```
1               5                   10                  15

Tyr Asp Glu Pro Ser Arg Gln Val Ile Leu Glu Ala Leu Ala Glu Phe
            20                  25                  30

Glu Arg Ser Thr Cys Ile Arg Phe Val Thr Tyr Gln Asp Gln Arg Asp
        35                  40                  45

Phe Ile Ser Ile Ile Pro Met Tyr Gly Cys Phe Ser Ser Val Gly Arg
    50                  55                  60

Ser Gly Gly Met Gln Val Val Ser Leu Ala Pro Thr Cys Leu Gln Lys
65                  70                  75                  80

Gly Arg Gly Ile Val Leu His Glu Leu Met His Val Leu Gly Phe Trp
                85                  90                  95

His Glu His Thr Arg Ala Asp Arg Asp Arg Tyr Ile Arg Val Asn Trp
            100                 105                 110

Asn Glu Ile Leu Pro Gly Phe Glu Ile Asn Phe Ile Lys Ser Gln Ser
        115                 120                 125

Ser Asn Met Leu Thr Pro Tyr Asp Tyr Ser Ser Val Met His Tyr Gly
    130                 135                 140

Arg Leu Ala Phe Ser Arg Arg Gly Leu Pro Thr Ile Thr Pro Leu Trp
145                 150                 155                 160

Ala Pro Ser Val His Ile Gly Gln Arg Trp Asn Leu Ser Ala Ser Asp
                165                 170                 175

Ile Thr Arg Val Leu Lys Leu Tyr Gly Cys Ser Pro Ser Gly Pro Arg
            180                 185                 190

Pro Arg Gly Arg Gly Ser His Ala His Ser Thr Gly Arg Ser Pro Ala
        195                 200                 205

Pro Ala Ser Leu Ser Leu Gln Arg Leu Leu Glu Ala Leu Ser Ala Glu
    210                 215                 220

Ser Arg Ser Pro Asp Pro Ser Gly Ser Ser Ala Gly Gly Gln Pro Val
225                 230                 235                 240

Pro Ala Gly Pro Gly Glu Ser Pro His Gly Trp Glu Ser Pro Ala Leu
                245                 250                 255

Lys Lys Leu Ser Ala Glu Ala Ser Ala Arg Gln Pro Gln Thr Leu Ala
            260                 265                 270

Ser Ser Pro Arg Ser Arg Pro Gly Ala Gly Ala Pro Gly Val Ala Gln
        275                 280                 285

Glu Gln Ser Trp Leu Ala Gly Val Ser Thr Lys Pro Thr Val Pro Ser
    290                 295                 300

Ser Glu Ala Gly Ile Gln Pro Val Pro Val Gln Gly Ser Pro Ala Leu
305                 310                 315                 320

Pro Gly Gly Cys Val Pro Arg Asn His Phe Lys Gly Met Ser Glu Asp
                325                 330                 335
```

<210> SEQ ID NO 15
<211> LENGTH: 55
<212> TYPE: DNA
<213> ORGANISM: Homo sapiens

<400> SEQUENCE: 15
atggagggtg tagggggtct ctggccttgg gtgctgggtc tgctctcctt gccag          55

<210> SEQ ID NO 16
<211> LENGTH: 19
<212> TYPE: PRT
<213> ORGANISM: Homo sapiens

<400> SEQUENCE: 16

-continued

```
Met Glu Gly Val Gly Gly Leu Trp Pro Trp Val Leu Gly Leu Leu Ser
1               5                   10                  15

Leu Pro Gly


<210> SEQ ID NO 17
<211> LENGTH: 126
<212> TYPE: DNA
<213> ORGANISM: Homo sapiens

<400> SEQUENCE: 17

gtgtgatcct aggagcgccc ctggcctcca gctgcgcagg agcctgtggt accagcttcc      60

cagatggcct cacccctgag ggaacccagg cctccgggga caaggacatt cctgcaatta     120

accaag                                                                126


<210> SEQ ID NO 18
<211> LENGTH: 42
<212> TYPE: PRT
<213> ORGANISM: Homo sapiens

<400> SEQUENCE: 18

Val Ile Leu Gly Ala Pro Leu Ala Ser Ser Cys Ala Gly Ala Cys Gly
1               5                   10                  15

Thr Ser Phe Pro Asp Gly Leu Thr Pro Glu Gly Thr Gln Ala Ser Gly
            20                  25                  30

Asp Lys Asp Ile Pro Ala Ile Asn Gln Gly
        35                  40


<210> SEQ ID NO 19
<211> LENGTH: 62
<212> TYPE: DNA
<213> ORGANISM: Homo sapiens

<400> SEQUENCE: 19

ggctcatcct ggaagaaacc ccagagagca gcttcctcat cgagggggac atcatccggc      60

cg                                                                     62


<210> SEQ ID NO 20
<211> LENGTH: 20
<212> TYPE: PRT
<213> ORGANISM: Homo sapiens

<400> SEQUENCE: 20

Leu Ile Leu Glu Glu Thr Pro Glu Ser Ser Phe Leu Ile Glu Gly Asp
1               5                   10                  15

Ile Ile Arg Pro
            20


<210> SEQ ID NO 21
<211> LENGTH: 94
<212> TYPE: DNA
<213> ORGANISM: Homo sapiens

<400> SEQUENCE: 21

agtcccttcc gactgctgtc agcaaccagc aacaaatggc ccatgggtgg tagtggtgtc      60

gtggaggtcc ccttcctgct ctccagcaag tacg                                  94


<210> SEQ ID NO 22
<211> LENGTH: 32
<212> TYPE: PRT
```

-continued

<213> ORGANISM: Homo sapiens

<400> SEQUENCE: 22

Ser Pro Phe Arg Leu Leu Ser Ala Thr Ser Asn Lys Trp Pro Met Gly
1 5 10 15

Gly Ser Gly Val Val Glu Val Pro Phe Leu Leu Ser Ser Lys Tyr Asp
20 25 30

<210> SEQ ID NO 23
<211> LENGTH: 118
<212> TYPE: DNA
<213> ORGANISM: Homo sapiens

<400> SEQUENCE: 23
atgagcccag ccgccaggtc atcctggagg ctcttgcgga gtttgaacgt tccacgtgca 60
tcaggtttgt cacctatcag gaccagagag acttcatttc catcatcccc atgtatgg 118

<210> SEQ ID NO 24
<211> LENGTH: 39
<212> TYPE: PRT
<213> ORGANISM: Homo sapiens

<400> SEQUENCE: 24

Glu Pro Ser Arg Gln Val Ile Leu Glu Ala Leu Ala Glu Phe Glu Arg
1 5 10 15

Ser Thr Cys Ile Arg Phe Val Thr Tyr Gln Asp Gln Arg Asp Phe Ile
20 25 30

Ser Ile Ile Pro Met Tyr Gly
35

<210> SEQ ID NO 25
<211> LENGTH: 182
<212> TYPE: DNA
<213> ORGANISM: Homo sapiens

<400> SEQUENCE: 25
gtgcttctcg agtgtggggc gcagtggagg gatgcaggtg gtctccctgg cgcccacgtg 60
tctccagaag ggccggggca ttgtccttca tgagctcatg catgtgctgg gcttctggca 120
cgagcacacg cgggccgacc gggaccgcta tatccgtgtc aactggaacg agatcctgcc 180
ag 182

<210> SEQ ID NO 26
<211> LENGTH: 61
<212> TYPE: PRT
<213> ORGANISM: Homo sapiens

<400> SEQUENCE: 26

Cys Phe Ser Ser Val Gly Arg Ser Gly Gly Met Gln Val Val Ser Leu
1 5 10 15

Ala Pro Thr Cys Leu Gln Lys Gly Arg Gly Ile Val Leu His Glu Leu
20 25 30

Met His Val Leu Gly Phe Trp His Glu His Thr Arg Ala Asp Arg Asp
35 40 45

Arg Tyr Ile Arg Val Asn Trp Asn Glu Ile Leu Pro Gly
50 55 60

<210> SEQ ID NO 27
<211> LENGTH: 82
<212> TYPE: DNA

-continued

<213> ORGANISM: Homo sapiens

<400> SEQUENCE: 27
gctttgaaat caacttcatc aagtctcgga gcagcaacat gctgacgccc tatgactact 60
cctctgtgat gcactatggg ag 82

<210> SEQ ID NO 28
<211> LENGTH: 27
<212> TYPE: PRT
<213> ORGANISM: Homo sapiens

<400> SEQUENCE: 28

Phe Glu Ile Asn Phe Ile Lys Ser Arg Ser Ser Asn Met Leu Thr Pro
1 5 10 15

Tyr Asp Tyr Ser Ser Val Met His Tyr Gly Arg
20 25

<210> SEQ ID NO 29
<211> LENGTH: 155
<212> TYPE: DNA
<213> ORGANISM: Homo sapiens

<400> SEQUENCE: 29
gctcgccttc agccggcgtg ggctgcccac catcacacca ctttgggccc ccagtgtcca 60
catcggccag cgatggaacc tgagtgcctc ggacatcacc cgggtcctca aactctacgg 120
ctgcagccca agtggcccca ggccccgtgg gagag 155

<210> SEQ ID NO 30
<211> LENGTH: 52
<212> TYPE: PRT
<213> ORGANISM: Homo sapiens

<400> SEQUENCE: 30

Leu Ala Phe Ser Arg Arg Gly Leu Pro Thr Ile Thr Pro Leu Trp Ala
1 5 10 15

Pro Ser Val His Ile Gly Gln Arg Trp Asn Leu Ser Ala Ser Asp Ile
20 25 30

Thr Arg Val Leu Lys Leu Tyr Gly Cys Ser Pro Ser Gly Pro Arg Pro
35 40 45

Arg Gly Arg Gly
50

<210> SEQ ID NO 31
<211> LENGTH: 419
<212> TYPE: DNA
<213> ORGANISM: Homo sapiens

<400> SEQUENCE: 31
ggtcccatgc ccacagcact ggtaggagcc ccgctccggc ctccctatct ctgcagcggc 60
ttttggaggc actgtcggcg gaatccagga gccccgaccc cagtggttcc agtgcgggag 120
gccagcccgt tcctgcaggg cctggggaga gcccacatgg gtgggagtcc cctgccctga 180
aaaagctcag tgcagaggcc tcggcaaggc agcctcagac cctagcttcc tccccaagat 240
caaggcctgg agcaggtgcc cccggtgttg ctcaggagca gtcctggctg gccggagtgt 300
ccaccaagcc cacagtccca tcttcagaag caggaatcca gccagtccct gtccagggaa 360
gcccagctct gccagggggc tgtgtaccta gaaatcattt caaggggatg tccgaagat 419

-continued

<210> SEQ ID NO 32
<211> LENGTH: 139
<212> TYPE: PRT
<213> ORGANISM: Homo sapiens

<400> SEQUENCE: 32

```
Ser His Ala His Ser Thr Gly Arg Ser Pro Ala Pro Ala Ser Leu Ser
1               5                   10                  15

Leu Gln Arg Leu Leu Glu Ala Leu Ser Ala Glu Ser Arg Ser Pro Asp
            20                  25                  30

Pro Ser Gly Ser Ser Ala Gly Gly Gln Pro Val Pro Ala Gly Pro Gly
        35                  40                  45

Glu Ser Pro His Gly Trp Glu Ser Pro Ala Leu Lys Lys Leu Ser Ala
    50                  55                  60

Glu Ala Ser Ala Arg Gln Pro Gln Thr Leu Ala Ser Ser Pro Arg Ser
65                  70                  75                  80

Arg Pro Gly Ala Gly Ala Pro Gly Val Ala Gln Glu Gln Ser Trp Leu
                85                  90                  95

Ala Gly Val Ser Thr Lys Pro Thr Val Pro Ser Ser Glu Ala Gly Ile
            100                 105                 110

Gln Pro Val Pro Val Gln Gly Ser Pro Ala Leu Pro Gly Gly Cys Val
        115                 120                 125

Pro Arg Asn His Phe Lys Gly Met Ser Glu Asp
    130                 135
```

<210> SEQ ID NO 33
<211> LENGTH: 1293
<212> TYPE: DNA
<213> ORGANISM: Homo sapiens

<400> SEQUENCE: 33

```
atggagggtg tagggggtct ctggccttgg gtgctgggtc tgctctcctt gccaggtgtg      60

atcctaggag cgcccctggc ctccagctgc gcaggagcct gtggtaccag cttcccagat     120

ggcctcaccc ctgagggaac ccaggcctcc ggggacaagg acattcctgc aattaaccaa     180

gggctcatcc tggaagaaac cccagagagc agcttcctca tcgagggggga catcatccgg     240

ccgagtccct tccgactgct gtcagcaacc agcaacaaat ggcccatggg tggtagtggt     300

gtcgtggagg tcccccttcct gctctccagc aagtacgatg agcccagccg ccaggtcatc     360

ctggaggctc ttgcggagtt tgaacgttcc acgtgcatca ggtttgtcac ctatcaggac     420

cagagagact tcatttccat catccccatg tatgggtgct tctcgagtgt ggggcgcagt     480

ggagggatgc aggtggtctc cctggcgccc acgtgtctcc agaagggccg gggcattgtc     540

cttcatgagc tcatgcatgt gctgggcttc tggcacgagc acacgcgggc cgaccgggac     600

cgctatatcc gtgtcaactg gaacgagatc ctgccaggct ttgaaatcaa cttcatcaag     660

tctcggagca gcaacatgct gacgccctat gactactcct ctgtgatgca ctatgggagg     720

ctcgccttca gccggcgtgg gctgcccacc atcacaccac tttgggcccc cagtgtccac     780

atcggccagc gatggaacct gagtgcctcg gacatcaccc gggtcctcaa actctacggc     840

tgcagcccaa gtggccccag gccccgtggg agagggtccc atgcccacag cactggtagg     900

agccccgctc cggcctccct atctctgcag cggcttttgg aggcactgtc ggcggaatcc     960

aggagccccg accccagtgg ttccagtgcg ggaggccagc ccgttcctgc agggcctggg    1020

gagagcccac atgggtggga gtcccctgcc ctgaaaaagc tcagtgcaga ggcctcggca    1080

aggcagcctc agaccctagc ttcctcccca agatcaaggc ctggagcagg tgcccccggt    1140
```

-continued

```
gttgctcagg agcagtcctg gctggccgga gtgtccacca agcccacagt cccatcttca   1200

gaagcaggaa tccagccagt ccctgtccag ggaagcccag ctctgccagg gggctgtgta   1260

cctagaaatc atttcaaggg gatgtccgaa gat                                1293


<210> SEQ ID NO 34
<211> LENGTH: 431
<212> TYPE: PRT
<213> ORGANISM: Homo sapiens

<400> SEQUENCE: 34

Met Glu Gly Val Gly Gly Leu Trp Pro Trp Val Leu Gly Leu Leu Ser
1               5                   10                  15

Leu Pro Gly Val Ile Leu Gly Ala Pro Leu Ala Ser Ser Cys Ala Gly
            20                  25                  30

Ala Cys Gly Thr Ser Phe Pro Asp Gly Leu Thr Pro Glu Gly Thr Gln
        35                  40                  45

Ala Ser Gly Asp Lys Asp Ile Pro Ala Ile Asn Gln Gly Leu Ile Leu
    50                  55                  60

Glu Glu Thr Pro Glu Ser Ser Phe Leu Ile Glu Gly Asp Ile Ile Arg
65                  70                  75                  80

Pro Ser Pro Phe Arg Leu Leu Ser Ala Thr Ser Asn Lys Trp Pro Met
                85                  90                  95

Gly Gly Ser Gly Val Val Glu Val Pro Phe Leu Leu Ser Ser Lys Tyr
            100                 105                 110

Asp Glu Pro Ser Arg Gln Val Ile Leu Glu Ala Leu Ala Glu Phe Glu
        115                 120                 125

Arg Ser Thr Cys Ile Arg Phe Val Thr Tyr Gln Asp Gln Arg Asp Phe
    130                 135                 140

Ile Ser Ile Ile Pro Met Tyr Gly Cys Phe Ser Ser Val Gly Arg Ser
145                 150                 155                 160

Gly Gly Met Gln Val Val Ser Leu Ala Pro Thr Cys Leu Gln Lys Gly
                165                 170                 175

Arg Gly Ile Val Leu His Glu Leu Met His Val Leu Gly Phe Trp His
            180                 185                 190

Glu His Thr Arg Ala Asp Arg Asp Arg Tyr Ile Arg Val Asn Trp Asn
        195                 200                 205

Glu Ile Leu Pro Gly Phe Glu Ile Asn Phe Ile Lys Ser Arg Ser Ser
    210                 215                 220

Asn Met Leu Thr Pro Tyr Asp Tyr Ser Ser Val Met His Tyr Gly Arg
225                 230                 235                 240

Leu Ala Phe Ser Arg Arg Gly Leu Pro Thr Ile Thr Pro Leu Trp Ala
                245                 250                 255

Pro Ser Val His Ile Gly Gln Arg Trp Asn Leu Ser Ala Ser Asp Ile
            260                 265                 270

Thr Arg Val Leu Lys Leu Tyr Gly Cys Ser Pro Ser Gly Pro Arg Pro
        275                 280                 285

Arg Gly Arg Gly Ser His Ala His Ser Thr Gly Arg Ser Pro Ala Pro
    290                 295                 300

Ala Ser Leu Ser Leu Gln Arg Leu Leu Glu Ala Leu Ser Ala Glu Ser
305                 310                 315                 320

Arg Ser Pro Asp Pro Ser Gly Ser Ser Ala Gly Gly Gln Pro Val Pro
                325                 330                 335

Ala Gly Pro Gly Glu Ser Pro His Gly Trp Glu Ser Pro Ala Leu Lys
```

-continued

```
            340                 345                 350

Lys Leu Ser Ala Glu Ala Ser Ala Arg Gln Pro Gln Thr Leu Ala Ser
        355                 360                 365

Ser Pro Arg Ser Arg Pro Gly Ala Gly Ala Pro Gly Val Ala Gln Glu
    370                 375                 380

Gln Ser Trp Leu Ala Gly Val Ser Thr Lys Pro Thr Val Pro Ser Ser
385                 390                 395                 400

Glu Ala Gly Ile Gln Pro Val Pro Val Gln Gly Ser Pro Ala Leu Pro
                405                 410                 415

Gly Gly Cys Val Pro Arg Asn His Phe Lys Gly Met Ser Glu Asp
            420                 425                 430


<210> SEQ ID NO 35
<211> LENGTH: 1224
<212> TYPE: DNA
<213> ORGANISM: Homo sapiens

<400> SEQUENCE: 35

gcgcccctgg cctccagctg cgcaggagcc tgtggtacca gcttcccaga tggcctcacc      60

cctgagggaa cccaggcctc cggggacaag gacattcctg caattaacca agggctcatc     120

ctggaagaaa ccccagagag cagcttcctc atcgaggggg acatcatccg gccgagtccc     180

ttccgactgc tgtcagcaac cagcaacaaa tggcccatgg gtggtagtgg tgtcgtggag     240

gtccccttcc tgctctccag caagtacgat gagcccagcc gccaggtcat cctggaggct     300

cttgcggagt ttgaacgttc cacgtgcatc aggtttgtca cctatcagga ccagagagac     360

ttcatttcca tcatccccat gtatgggtgc ttctcgagtg tggggcgcag tggagggatg     420

caggtggtct ccctggcgcc cacgtgtctc cagaagggcc ggggcattgt ccttcatgag     480

ctcatgcatg tgctgggctt ctggcacgag cacacgcggg ccgaccggga ccgctatatc     540

cgtgtcaact ggaacgagat cctgccaggc tttgaaatca acttcatcaa gtctcggagc     600

agcaacatgc tgacgcccta tgactactcc tctgtgatgc actatgggag gctcgccttc     660

agccggcgtg ggctgcccac catcacacca ctttgggccc ccagtgtcca catcggccag     720

cgatggaacc tgagtgcctc ggacatcacc cgggtcctca aactctacgg ctgcagccca     780

agtggcccca ggccccgtgg gagagggtcc catgcccaca gcactggtag gagccccgct     840

ccggcctccc tatctctgca gcggcttttg gaggcactgt cggcggaatc caggagcccc     900

gaccccagtg gttccagtgc gggaggccag cccgttcctg cagggcctgg ggagagccca     960

catgggtggg agtcccctgc cctgaaaaag ctcagtgcag aggcctcggc aaggcagcct    1020

cagaccctag cttcctcccc aagatcaagg cctggagcag gtgcccccgg tgttgctcag    1080

gagcagtcct ggctggccgg agtgtccacc aagcccacag tcccatcttc agaagcagga    1140

atccagccag tccctgtcca gggaagccca gctctgccag gggctgtgt acctagaaat     1200

catttcaagg ggatgtccga agat                                            1224


<210> SEQ ID NO 36
<211> LENGTH: 408
<212> TYPE: PRT
<213> ORGANISM: Homo sapiens

<400> SEQUENCE: 36

Ala Pro Leu Ala Ser Ser Cys Ala Gly Ala Cys Gly Thr Ser Phe Pro
1               5                   10                  15

Asp Gly Leu Thr Pro Glu Gly Thr Gln Ala Ser Gly Asp Lys Asp Ile
```

-continued

```
            20                  25                  30

Pro Ala Ile Asn Gln Gly Leu Ile Leu Glu Glu Thr Pro Glu Ser Ser
        35                  40                  45

Phe Leu Ile Glu Gly Asp Ile Ile Arg Pro Ser Pro Phe Arg Leu Leu
    50                  55                  60

Ser Ala Thr Ser Asn Lys Trp Pro Met Gly Gly Ser Gly Val Val Glu
65                  70                  75                  80

Val Pro Phe Leu Leu Ser Ser Lys Tyr Asp Glu Pro Ser Arg Gln Val
                85                  90                  95

Ile Leu Glu Ala Leu Ala Glu Phe Glu Arg Ser Thr Cys Ile Arg Phe
            100                 105                 110

Val Thr Tyr Gln Asp Gln Arg Asp Phe Ile Ser Ile Ile Pro Met Tyr
        115                 120                 125

Gly Cys Phe Ser Ser Val Gly Arg Ser Gly Gly Met Gln Val Val Ser
    130                 135                 140

Leu Ala Pro Thr Cys Leu Gln Lys Gly Arg Gly Ile Val Leu His Glu
145                 150                 155                 160

Leu Met His Val Leu Gly Phe Trp His Glu His Thr Arg Ala Asp Arg
                165                 170                 175

Asp Arg Tyr Ile Arg Val Asn Trp Asn Glu Ile Leu Pro Gly Phe Glu
            180                 185                 190

Ile Asn Phe Ile Lys Ser Arg Ser Ser Asn Met Leu Thr Pro Tyr Asp
        195                 200                 205

Tyr Ser Ser Val Met His Tyr Gly Arg Leu Ala Phe Ser Arg Arg Gly
    210                 215                 220

Leu Pro Thr Ile Thr Pro Leu Trp Ala Pro Ser Val His Ile Gly Gln
225                 230                 235                 240

Arg Trp Asn Leu Ser Ala Ser Asp Ile Thr Arg Val Leu Lys Leu Tyr
                245                 250                 255

Gly Cys Ser Pro Ser Gly Pro Arg Pro Arg Gly Arg Gly Ser His Ala
            260                 265                 270

His Ser Thr Gly Arg Ser Pro Ala Pro Ala Ser Leu Ser Leu Gln Arg
        275                 280                 285

Leu Leu Glu Ala Leu Ser Ala Glu Ser Arg Ser Pro Asp Pro Ser Gly
    290                 295                 300

Ser Ser Ala Gly Gly Gln Pro Val Pro Ala Gly Pro Gly Glu Ser Pro
305                 310                 315                 320

His Gly Trp Glu Ser Pro Ala Leu Lys Lys Leu Ser Ala Glu Ala Ser
                325                 330                 335

Ala Arg Gln Pro Gln Thr Leu Ala Ser Ser Pro Arg Ser Arg Pro Gly
            340                 345                 350

Ala Gly Ala Pro Gly Val Ala Gln Glu Gln Ser Trp Leu Ala Gly Val
        355                 360                 365

Ser Thr Lys Pro Thr Val Pro Ser Ser Glu Ala Gly Ile Gln Pro Val
    370                 375                 380

Pro Val Gln Gly Ser Pro Ala Leu Pro Gly Gly Cys Val Pro Arg Asn
385                 390                 395                 400

His Phe Lys Gly Met Ser Glu Asp
                405
```

<210> SEQ ID NO 37
<211> LENGTH: 300
<212> TYPE: PRT
<213> ORGANISM: Homo sapiens -continued

<400> SEQUENCE: 37

```
Met Leu Arg Leu Trp Asp Phe Asn Pro Gly Gly Ala Leu Ser Asp Leu
1               5                   10                  15

Ala Leu Gly Leu Arg Gly Met Glu Glu Gly Gly Tyr Ser Cys Ala Gly
            20                  25                  30

Ala Cys Gly Thr Ser Phe Pro Asp Gly Leu Thr Pro Glu Gly Thr Gln
        35                  40                  45

Ala Ser Gly Asp Lys Asp Ile Pro Ala Ile Asn Gln Gly Leu Ile Leu
    50                  55                  60

Glu Glu Thr Pro Glu Ser Ser Phe Leu Ile Glu Gly Asp Ile Ile Arg
65                  70                  75                  80

Pro Ser Pro Phe Arg Leu Leu Ser Ala Thr Ser Asn Lys Trp Pro Met
                85                  90                  95

Gly Gly Ser Gly Val Val Glu Val Pro Phe Leu Leu Ser Ser Lys Tyr
            100                 105                 110

Asp Glu Pro Ser His Gln Val Ile Leu Glu Ala Leu Ala Glu Phe Glu
        115                 120                 125

Arg Ser Thr Cys Ile Arg Phe Val Thr Tyr Gln Asp Gln Arg Asp Phe
    130                 135                 140

Ile Ser Ile Ile Pro Met Tyr Gly Cys Phe Ser Ser Val Gly Arg Ser
145                 150                 155                 160

Gly Gly Met Gln Val Val Ser Leu Ala Pro Thr Cys Leu Gln Lys Gly
                165                 170                 175

Arg Gly Ile Val Leu His Glu Leu Met His Val Leu Gly Phe Trp His
            180                 185                 190

Glu His Thr Arg Ala Asp Arg Asp Arg Tyr Ile Arg Val Asn Trp Asn
        195                 200                 205

Glu Ile Leu Pro Gly Phe Glu Ile Asn Phe Ile Lys Ser Gln Ser Ser
    210                 215                 220

Asn Met Leu Thr Pro Tyr Asp Tyr Ser Ser Val Met His Tyr Gly Arg
225                 230                 235                 240

Leu Ala Phe Ser Arg Arg Gly Leu Pro Thr Ile Thr Pro Leu Trp Ala
                245                 250                 255

Pro Ser Val His Ile Gly Gln Arg Trp Asn Leu Ser Ala Ser Asp Ile
            260                 265                 270

Thr Arg Val Leu Lys Leu Tyr Gly Cys Ser Pro Ser Gly Pro Arg Pro
        275                 280                 285

Arg Gly Arg Gly Glu Trp His Gly Arg Lys Val Thr
    290                 295                 300
```

<210> SEQ ID NO 38
<211> LENGTH: 5005
<212> TYPE: DNA
<213> ORGANISM: Artificial Sequence
<220> FEATURE:
<223> OTHER INFORMATION: pCR4 TOPO IPAAA78836-1 plasmid sequence

<400> SEQUENCE: 38

```
agcgcccaat acgcaaaccg cctctccccg cgcgttggcc gattcattaa tgcagctggc      60

acgacaggtt tcccgactgg aaagcgggca gtgagcgcaa cgcaattaat gtgagttagc     120

tcactcatta ggcaccccag gctttacact ttatgcttcc ggctcgtatg ttgtgtggaa     180

ttgtgagcgg ataacaattt cacacaggaa acagctatga ccatgattac gccaagctca     240

gaattaaccc tcactaaagg gactagtcct gcaggtttaa acgaattcgc ccttagccac     300
```

-continued

```
aggcttaatc ttcggacatc cccttgaaat gatttctagg tacacagccc cctggcagag    360
ctgggcttcc ctggacaggg actggctgga ttcctgcttc tgaagatggg actgtgggct    420
tggtggacac tccggccagc caggactgct cctgagcaac accgggggca cctgctccag    480
gccttgatct tggggaggaa gctagggtct gaggctgcct tgccgaggcc tctgcactga    540
gctttttcag ggcaggggac tcccacccat gtgggctctc cccaggccct gcaggaacgg    600
gctggcctcc cgcactggaa ccactggggt cggggctcct ggattccgcc gacagtgcct    660
ccaaaagccg ctgcagagat agggaggccg gggcggggct cctaccagtg ctgtgggcat    720
gggaccctct cccacggggc ctggggccac ttgggctgca gccgtagagt ttgaggaccc    780
gggtgatgtc cgaggcactc aggttccatc gctggccgat gtggacactg ggggcccaaa    840
gtggtgtgat ggtgggcagc ccacgccggc tgaaggcgag cctcccatag tgcatcacag    900
aggagtagtc atagggcgtc agcatgttgc tgctctgaga cttgatgaag ttgatttcaa    960
agcctggcag gatctcgttc cagttgacac ggatatagcg gtcccggtcg gcccgcgtgt   1020
gctcgtgcca gaagcccagc acatgcatga gctcatgaag gacaatgccc cggcccttct   1080
ggagacacgt gggcgccagg gagaccacct gcatccctcc actgcgcccc acactcgaga   1140
agcacccata catggggatg atggaaatga agtctctctg gtcctgatag gtgacaaacc   1200
tgatgcacgt ggaacgttca aactccgcaa gagcctccag gatgacctgg cggctgggct   1260
catcgtactt gctggagagc aggaagggga cctccacgac accactacca cccatgggcc   1320
atttgttgct ggttgctgac agaagggcga attcgcggcc gctaaattca attcgcccta   1380
tagtgagtcg tattacaatt cactggccgt cgttttacaa cgtcgtgact gggaaaaccc   1440
tggcgttacc caacttaatc gccttgcagc acatccccct ttcgccagct ggcgtaatag   1500
cgaagaggcc cgcaccgatc gcccttccca acagttgcgc agcctatacg tacggcagtt   1560
taaggtttac acctataaaa gagagagccg ttatcgtctg tttgtggatg tacagagtga   1620
tattattgac acgccggggc gacggatggt gatccccctg gccagtgcac gtctgctgtc   1680
agataaagtc tcccgtgaac tttacccggt ggtgcatatc ggggatgaaa gctggcgcat   1740
gatgaccacc gatatggcca gtgtgccggt ctccgttatc ggggaagaag tggctgatct   1800
cagccaccgc gaaaatgaca tcaaaaacgc cattaacctg atgttctggg gaatataaat   1860
gtcaggcatg agattatcaa aaaggatctt cacctagatc cttttcacgt agaaagccag   1920
tccgcagaaa cggtgctgac cccggatgaa tgtcagctac tgggctatct ggacaaggga   1980
aaacgcaagc gcaaagagaa agcaggtagc ttgcagtggg cttacatggc gatagctaga   2040
ctgggcggtt ttatggacag caagcgaacc ggaattgcca gctggggcgc cctctggtaa   2100
ggttgggaag ccctgcaaag taaactggat ggctttctcg ccgccaagga tctgatggcg   2160
caggggatca agctctgatc aagagacagg atgaggatcg tttcgcatga ttgaacaaga   2220
tggattgcac gcaggttctc cggccgcttg ggtggagagg ctattcggct atgactgggc   2280
acaacagaca atcggctgct ctgatgccgc cgtgttccgg ctgtcagcgc aggggcgccc   2340
ggttcttttt gtcaagaccg acctgtccgg tgccctgaat gaactgcaag acgaggcagc   2400
gcggctatcg tggctggcca cgacgggcgt tccttgcgca gctgtgctcg acgttgtcac   2460
tgaagcggga agggactggc tgctattggg cgaagtgccg gggcaggatc tcctgtcatc   2520
tcaccttgct cctgccgaga aagtatccat catggctgat gcaatgcggc ggctgcatac   2580
gcttgatccg gctacctgcc cattcgacca ccaagcgaaa catcgcatcg agcgagcacg   2640
```

-continued

```
tactcggatg gaagccggtc ttgtcgatca ggatgatctg gacgaagagc atcaggggct   2700
cgcgccagcc gaactgttcg ccaggctcaa ggcgagcatg cccgacggcg aggatctcgt   2760
cgtgacccat ggcgatgcct gcttgccgaa tatcatggtg gaaaatggcc gcttttctgg   2820
attcatcgac tgtggccggc tgggtgtggc ggaccgctat caggacatag cgttggctac   2880
ccgtgatatt gctgaagagc ttggcggcga atgggctgac cgcttcctcg tgctttacgg   2940
tatcgccgct cccgattcgc agcgcatcgc cttctatcgc cttcttgacg agttcttctg   3000
aattattaac gcttacaatt tcctgatgcg gtattttctc cttacgcatc tgtgcggtat   3060
ttcacaccgc atacaggtgg cacttttcgg ggaaatgtgc gcggaacccc tatttgttta   3120
tttttctaaa tacattcaaa tatgtatccg ctcatgagac aataaccctg ataaatgctt   3180
caataatatt gaaaaaggaa gagtatgagt attcaacatt tccgtgtcgc ccttattccc   3240
ttttttgcgg cattttgcct tcctgttttt gctcacccag aaacgctggt gaaagtaaaa   3300
gatgctgaag atcagttggg tgcacgagtg ggttacatcg aactggatct caacagcggt   3360
aagatccttg agagttttcg ccccgaagaa cgttttccaa tgatgagcac ttttaaagtt   3420
ctgctatgtg gcgcggtatt atcccgtatt gacgccgggc aagagcaact cggtcgccgc   3480
atacactatt ctcagaatga cttggttgag tactcaccag tcacagaaaa gcatcttacg   3540
gatggcatga cagtaagaga attatgcagt gctgccataa ccatgagtga taacactgcg   3600
gccaacttac ttctgacaac gatcggagga ccgaaggagc taaccgcttt tttgcacaac   3660
atgggggatc atgtaactcg ccttgatcgt tgggaaccgg agctgaatga agccatacca   3720
aacgacgagc gtgacaccac gatgcctgta gcaatggcaa caacgttgcg caaactatta   3780
actggcgaac tacttactct agcttcccgg caacaattaa tagactggat ggaggcggat   3840
aaagttgcag gaccacttct gcgctcggcc cttccggctg gctggtttat tgctgataaa   3900
tctggagccg gtgagcgtgg gtctcgcggt atcattgcag cactggggcc agatggtaag   3960
ccctcccgta tcgtagttat ctacacgacg gggagtcagg caactatgga tgaacgaaat   4020
agacagatcg ctgagatagg tgcctcactg attaagcatt ggtaactgtc agaccaagtt   4080
tactcatata tactttagat tgatttaaaa cttcattttt aatttaaaag gatctaggtg   4140
aagatccttt ttgataatct catgaccaaa atcccttaac gtgagttttc gttccactga   4200
gcgtcagacc ccgtagaaaa gatcaaagga tcttcttgag atcctttttt tctgcgcgta   4260
atctgctgct tgcaaacaaa aaaaccaccg ctaccagcgg tggtttgttt gccggatcaa   4320
gagctaccaa ctctttttcc gaaggtaact ggcttcagca gagcgcagat accaaatact   4380
gtccttctag tgtagccgta gttaggccac cacttcaaga actctgtagc accgcctaca   4440
tacctcgctc tgctaatcct gttaccagtg gctgctgcca gtggcgataa gtcgtgtctt   4500
accgggttgg actcaagacg atagttaccg gataaggcgc agcggtcggg ctgaacgggg   4560
ggttcgtgca cacagcccag cttggagcga acgacctaca ccgaactgag atacctacag   4620
cgtgagctat gagaaagcgc cacgcttccc gaagggagaa aggcggacag gtatccggta   4680
agcggcaggg tcggaacagg agagcgcacg agggagcttc caggggggaaa cgcctggtat  4740
ctttatagtc ctgtcgggtt tcgccacctc tgacttgagc gtcgattttt gtgatgctcg   4800
tcaggggggc ggagcctatg gaaaaacgcc agcaacgcgg cctttttacg gttcctgggc   4860
ttttgctggc cttttgctca catgttcttt cctgcgttat cccctgattc tgtggataac   4920
cgtattaccg cctttgagtg agctgatacc gctcgccgca gccgaacgac cgagcgcagc   4980
gagtcagtga gcgaggaagc ggaag                                         5005
```

-continued

<210> SEQ ID NO 39
<211> LENGTH: 5269
<212> TYPE: DNA
<213> ORGANISM: Artificial Sequence
<220> FEATURE:
<223> OTHER INFORMATION: XpCR4TOPO IPAAA78836-2 plasmid sequence

<400> SEQUENCE: 39

```
agcgcccaat acgcaaaccg cctctccccg cgcgttggcc gattcattaa tgcagctggc     60

acgacaggtt tcccgactgg aaagcgggca gtgagcgcaa cgcaattaat gtgagttagc    120

tcactcatta ggcaccccag gctttacact ttatgcttcc ggctcgtatg ttgtgtggaa    180

ttgtgagcgg ataacaattt cacacaggaa acagctatga ccatgattac gccaagctca    240

gaattaaccc tcactaaagg gactagtcct gcaggtttaa acgaattcgc ccttagccac    300

aggcttaatc ttcggacatc cccttgaaat gatttctagg tacacagccc cctggcagag    360

ctgggcttcc ctggacaggg actggctgga ttcctgcttc tgaagatggg actgtgggct    420

tggtggacac tccggccagc caggactgct cctgagcaac accgggggca cctgctccag    480

gccttgatct tggggaggaa gctagggtct gaggctgcct tgccgaggcc tctgcactga    540

gctttttcag ggcaggggac tcccacccat gtgggctctc cccaggccct gcaggaacgg    600

gctggcctcc cgcactggaa ccactggggt cggggctcct ggattccgcc gacagtgcct    660

ccaaaagccg ctgcagagat agggaggccg gagcggggct cctaccagtg ctgtgggcat    720

gggaccctct cccacggggc ctggggccac ttgggctgca gccgtagagt ttgaggaccc    780

gggtgatgtc cgaggcactc aggttccatc gctggccgat gtggacactg ggggcccaaa    840

gtggtgtgat ggtgggcagc ccacgccggc tgaaggcgag cctcccatag tgcatcacag    900

aggagtagtc atagggcgtc agcatgttgc tgctccgaga cttgatgaag ttgatttcaa    960

agcctggcag gatctcgttc cagttgacac ggatatagcg gtcccggtcg gcccgcgtgt   1020

gctcgtgcca gaagcccagc acatgcatga gctcatgaag gacaatgccc cggcccttct   1080

ggagacacgt gggcgccagg gagaccacct gcatccctcc actgcgcccc acactcgaga   1140

agcacccata catggggatg atggaaatga agtctctctg gtcctgatag gtgacaaacc   1200

tgatgcacgt ggaacgttca aactccgcaa gagcctccag gatgacctgg cggctgggct   1260

catcgtactt gctggagagc aggaagggga cctccacgac accactacca cccatgggcc   1320

atttgttgct ggttgctgac agcagtcgga agggactcgg ccggatgatg tccccctcga   1380

tgaggaagct gctctctggg gtttcttcca ggatgagccc ttggttaatt gcaggaatgt   1440

ccttgtcccc ggaggcctgg gttccctcag ggtgaggcc atctgggaag ctggtaccac   1500

aggctcctgc gcagctggag gccaggggcg ctcctaggat cacacctggc aaggagagca   1560

gacccagcac ccaaggccag agaccccta caccctccat ggtagaaagg gcgaattcgc   1620

ggccgctaaa ttcaattcgc cctatagtga gtcgtattac aattcactgg ccgtcgtttt   1680

acaacgtcgt gactgggaaa accctggcgt tacccaactt aatcgccttg cagcacatcc   1740

ccctttcgcc agctggcgta atagcgaaga ggcccgcacc gatcgccctt cccaacagtt   1800

gcgcagccta tacgtacggc agtttaaggt ttacacctat aaaagagaga gccgttatcg   1860

tctgtttgtg gatgtacaga gtgatattat tgacacgccg gggcgacgga tggtgatccc   1920

cctggccagt gcacgtctgc tgtcagataa agtctcccgt gaactttacc cggtggtgca   1980

tatcggggat gaaagctggc gcatgatgac caccgatatg gccagtgtgc cggtctccgt   2040
```

-continued

```
tatcggggaa gaagtggctg atctcagcca ccgcgaaaat gacatcaaaa acgccattaa   2100
cctgatgttc tggggaatat aaatgtcagg catgagatta tcaaaaagga tcttcaccta   2160
gatccttttc acgtagaaag ccagtccgca gaaacggtgc tgaccccgga tgaatgtcag   2220
ctactgggct atctggacaa gggaaaacgc aagcgcaaag agaaagcagg tagcttgcag   2280
tgggcttaca tggcgatagc tagactgggc ggttttatgg acagcaagcg aaccggaatt   2340
gccagctggg gcgccctctg gtaaggttgg gaagccctgc aaagtaaact ggatggcttt   2400
ctcgccgcca aggatctgat ggcgcagggg atcaagctct gatcaagaga caggatgagg   2460
atcgtttcgc atgattgaac aagatggatt gcacgcaggt tctccggccg cttgggtgga   2520
gaggctattc ggctatgact gggcacaaca gacaatcggc tgctctgatg ccgccgtgtt   2580
ccggctgtca gcgcaggggc gcccggttct ttttgtcaag accgacctgt ccggtgccct   2640
gaatgaactg caagacgagg cagcgcggct atcgtggctg gccacgacgg gcgttccttg   2700
cgcagctgtg ctcgacgttg tcactgaagc gggaagggac tggctgctat tgggcgaagt   2760
gccggggcag gatctcctgt catctcacct tgctcctgcc gagaaagtat ccatcatggc   2820
tgatgcaatg cggcggctgc atacgcttga tccggctacc tgcccattcg accaccaagc   2880
gaaacatcgc atcgagcgag cacgtactcg gatggaagcc ggtcttgtcg atcaggatga   2940
tctggacgaa gagcatcagg ggctcgcgcc agccgaactg ttcgccaggc tcaaggcgag   3000
catgcccgac ggcgaggatc tcgtcgtgac ccatggcgat gcctgcttgc cgaatatcat   3060
ggtggaaaat ggccgctttt ctggattcat cgactgtggc cggctgggtg tggcggaccg   3120
ctatcaggac atagcgttgg ctacccgtga tattgctgaa gagcttggcg gcgaatgggc   3180
tgaccgcttc ctcgtgcttt acggtatcgc cgctcccgat tcgcagcgca tcgccttcta   3240
tcgccttctt gacgagttct tctgaattat taacgcttac aatttcctga tgcggtattt   3300
tctccttacg catctgtgcg gtatttcaca ccgcatacag gtggcacttt tcggggaaat   3360
gtgcgcggaa cccctatttg tttatttttc taaatacatt caaatatgta tccgctcatg   3420
agacaataac cctgataaat gcttcaataa tattgaaaaa ggaagagtat gagtattcaa   3480
catttccgtg tcgcccttat tccctttttt gcggcatttt gccttcctgt ttttgctcac   3540
ccagaaacgc tggtgaaagt aaaagatgct gaagatcagt tgggtgcacg agtgggttac   3600
atcgaactgg atctcaacag cggtaagatc cttgagagtt ttcgccccga agaacgtttt   3660
ccaatgatga gcacttttaa agttctgcta tgtggcgcgg tattatcccg tattgacgcc   3720
gggcaagagc aactcggtcg ccgcatacac tattctcaga atgacttggt tgagtactca   3780
ccagtcacag aaaagcatct tacggatggc atgacagtaa gagaattatg cagtgctgcc   3840
ataaccatga gtgataacac tgcggccaac ttacttctga caacgatcgg aggaccgaag   3900
gagctaaccg cttttttgca caacatgggg gatcatgtaa ctcgccttga tcgttgggaa   3960
ccggagctga atgaagccat accaaacgac gagcgtgaca ccacgatgcc tgtagcaatg   4020
gcaacaacgt tgcgcaaact attaactggc gaactactta ctctagcttc ccggcaacaa   4080
ttaatagact ggatggaggc ggataaagtt gcaggaccac ttctgcgctc ggcccttccg   4140
gctggctggt ttattgctga taaatctgga gccggtgagc gtgggtctcg cggtatcatt   4200
gcagcactgg ggccagatgg taagccctcc cgtatcgtag ttatctacac gacggggagt   4260
caggcaacta tggatgaacg aaatagacag atcgctgaga taggtgcctc actgattaag   4320
cattggtaac tgtcagacca agtttactca tatatacttt agattgattt aaaacttcat   4380
ttttaattta aaaggatcta ggtgaagatc ctttttgata atctcatgac caaaatccct   4440
```

-continued

```
taacgtgagt tttcgttcca ctgagcgtca gaccccgtag aaaagatcaa aggatcttct   4500

tgagatcctt tttttctgcg cgtaatctgc tgcttgcaaa caaaaaaacc accgctacca   4560

gcggtggttt gtttgccgga tcaagagcta ccaactcttt ttccgaaggt aactggcttc   4620

agcagagcgc agataccaaa tactgtcctt ctagtgtagc cgtagttagg ccaccacttc   4680

aagaactctg tagcaccgcc tacatacctc gctctgctaa tcctgttacc agtggctgct   4740

gccagtggcg ataagtcgtg tcttaccggg ttggactcaa gacgatagtt accggataag   4800

gcgcagcggt cgggctgaac ggggggttcg tgcacacagc ccagcttgga gcgaacgacc   4860

tacaccgaac tgagatacct acagcgtgag ctatgagaaa gcgccacgct tcccgaaggg   4920

agaaaggcgg acaggtatcc ggtaagcggc agggtcggaa caggagagcg cacgagggag   4980

cttccagggg gaaacgcctg gtatctttat agtcctgtcg ggtttcgcca cctctgactt   5040

gagcgtcgat ttttgtgatg ctcgtcaggg gggcggagcc tatggaaaaa cgccagcaac   5100

gcggcctttt tacggttcct gggcttttgc tggccttttg ctcacatgtt ctttcctgcg   5160

ttatcccctg attctgtgga taaccgtatt accgcctttg agtgagctga taccgctcgc   5220

cgcagccgaa cgaccgagcg cagcgagtca gtgagcgagg aagcggaag               5269


<210> SEQ ID NO 40
<211> LENGTH: 19
<212> TYPE: DNA
<213> ORGANISM: Artificial Sequence
<220> FEATURE:
<223> OTHER INFORMATION: Primer CP1

<400> SEQUENCE: 40

accgctatat ccgtgtcaa                                                  19


<210> SEQ ID NO 41
<211> LENGTH: 18
<212> TYPE: DNA
<213> ORGANISM: Artificial Sequence
<220> FEATURE:
<223> OTHER INFORMATION: Primer CP2

<400> SEQUENCE: 41

gctgcagccg tagagttt                                                   18


<210> SEQ ID NO 42
<211> LENGTH: 25
<212> TYPE: DNA
<213> ORGANISM: Artificial Sequence
<220> FEATURE:
<223> OTHER INFORMATION: GeneRacer 3' Primer

<400> SEQUENCE: 42

gctgtcaacg atacgctacg taacg                                           25


<210> SEQ ID NO 43
<211> LENGTH: 26
<212> TYPE: DNA
<213> ORGANISM: Artificial Sequence
<220> FEATURE:
<223> OTHER INFORMATION: 78836-GR1-3' Primer

<400> SEQUENCE: 43

agtgtccaca tcggccagcg atggaa                                          26


<210> SEQ ID NO 44
```

-continued

<211> LENGTH: 23
<212> TYPE: DNA
<213> ORGANISM: Artificial Sequence
<220> FEATURE:
<223> OTHER INFORMATION: GeneRacer 3' nested primer

<400> SEQUENCE: 44
cgctacgtaa cggcatgaca gtg 23

<210> SEQ ID NO 45
<211> LENGTH: 25
<212> TYPE: DNA
<213> ORGANISM: Artificial Sequence
<220> FEATURE:
<223> OTHER INFORMATION: 78836-GR1nest-3' primer

<400> SEQUENCE: 45
atggaacctg agtgcctcgg acatc 25

<210> SEQ ID NO 46
<211> LENGTH: 20
<212> TYPE: DNA
<213> ORGANISM: Artificial Sequence
<220> FEATURE:
<223> OTHER INFORMATION: 78836-FL-F primer

<400> SEQUENCE: 46
ctgtcagcaa ccagcaacaa 20

<210> SEQ ID NO 47
<211> LENGTH: 20
<212> TYPE: DNA
<213> ORGANISM: Artificial Sequence
<220> FEATURE:
<223> OTHER INFORMATION: 78836-FL-R primer

<400> SEQUENCE: 47
agccacaggc ttaatcttcg 20

<210> SEQ ID NO 48
<211> LENGTH: 20
<212> TYPE: DNA
<213> ORGANISM: Artificial Sequence
<220> FEATURE:
<223> OTHER INFORMATION: 78836-FL2-F primer

<400> SEQUENCE: 48
tctaccatgg agggtgtagg 20

<210> SEQ ID NO 49
<211> LENGTH: 20
<212> TYPE: DNA
<213> ORGANISM: Artificial Sequence
<220> FEATURE:
<223> OTHER INFORMATION: T3 primer

<400> SEQUENCE: 49
attaaccctc actaaaggga 20

<210> SEQ ID NO 50
<211> LENGTH: 20
<212> TYPE: DNA
<213> ORGANISM: Artificial Sequence
<220> FEATURE:
<223> OTHER INFORMATION: T7 primer

<400> SEQUENCE: 50

-continued

```
taatacgact cactataggg                                          20


<210> SEQ ID NO 51
<211> LENGTH: 18
<212> TYPE: DNA
<213> ORGANISM: Artificial Sequence
<220> FEATURE:
<223> OTHER INFORMATION: SP6 primer

<400> SEQUENCE: 51

atttaggtga cactatag                                            18
```